United States Patent
Taylor

(10) Patent No.: US 9,839,484 B2
(45) Date of Patent: Dec. 12, 2017

(54) METHOD AND SYSTEM FOR IMAGE PROCESSING AND PATIENT-SPECIFIC MODELING OF BLOOD FLOW

(71) Applicant: HeartFlow, Inc., Redwood City, CA (US)

(72) Inventor: Charles A. Taylor, Menlo Park, CA (US)

(73) Assignee: HeartFlow, Inc., Redwood City, CA (US)

(*) Notice: Subject to any disclaimer, the term of this patent is extended or adjusted under 35 U.S.C. 154(b) by 0 days.

(21) Appl. No.: 15/248,632

(22) Filed: Aug. 26, 2016

(65) Prior Publication Data

US 2016/0371455 A1    Dec. 22, 2016

Related U.S. Application Data

(60) Continuation of application No. 14/866,098, filed on Sep. 25, 2015, which is a continuation of application
(Continued)

(51) Int. Cl.
*G06K 9/00* (2006.01)
*A61B 34/10* (2016.01)
(Continued)

(52) U.S. Cl.
CPC .............. *A61B 34/10* (2016.02); *A61B 5/004* (2013.01); *A61B 5/0035* (2013.01);
(Continued)

(58) Field of Classification Search
CPC ........ A61B 2034/104; A61B 2034/105; A61B 2034/107; A61B 2034/108;
(Continued)

(56) References Cited

U.S. PATENT DOCUMENTS 4,821,735 A    4/1989 Goor et al.
5,119,816 A    6/1992 Gevins
(Continued)

FOREIGN PATENT DOCUMENTS

CN    201015590 Y    2/2008
EP    0 559 919 A1    9/1993
(Continued)

OTHER PUBLICATIONS de Bruyne et al. Simultaneous Coronary Pressure and Flow Velocity Measurements in Humans, 1996, American Heart Association, Circulation, vol. 94, pp. 1842-1849.*
(Continued)

*Primary Examiner* — Manuchehr Rahmjoo
(74) *Attorney, Agent, or Firm* — Bookoff McAndrews, PLLC

(57) ABSTRACT

Embodiments include a system for determining cardiovascular information for a patient. The system may include at least one computer system configured to receive patient-specific data regarding a geometry of the patient's heart, and create a three-dimensional model representing at least a portion of the patient's heart based on the patient-specific data. The at least one computer system may be further configured to create a physics-based model relating to a blood flow characteristic of the patient's heart and determine a fractional flow reserve within the patient's heart based on the three-dimensional model and the physics-based model.

18 Claims, 30 Drawing Sheets

Related U.S. Application Data

No. 14/276,442, filed on May 13, 2014, now Pat. No. 9,226,672, which is a continuation of application No. 13/658,739, filed on Oct. 23, 2012, which is a continuation of application No. 13/014,835, filed on Jan. 27, 2011, now Pat. No. 8,311,747, which is a division of application No. 13/013,561, filed on Jan. 25, 2011, now Pat. No. 8,315,812.

(60) Provisional application No. 61/404,429, filed on Oct. 1, 2010, provisional application No. 61/402,345, filed on Aug. 27, 2010, provisional application No. 61/402,308, filed on Aug. 26, 2010, provisional application No. 61/401,915, filed on Aug. 20, 2010, provisional application No. 61/401,462, filed on Aug. 12, 2010.

(51) Int. Cl.

| | | |
|---|---|---|
| *G06F 17/10* | (2006.01) | |
| *A61B 34/00* | (2016.01) | |
| *A61B 5/02* | (2006.01) | |
| *A61B 5/026* | (2006.01) | |
| *G06F 19/00* | (2011.01) | |
| *G06G 7/60* | (2006.01) | |
| *G06F 19/26* | (2011.01) | |
| *A61B 5/00* | (2006.01) | |
| *A61B 5/029* | (2006.01) | |
| *A61B 6/03* | (2006.01) | |
| *A61B 6/00* | (2006.01) | |
| *A61B 8/06* | (2006.01) | |
| *A61B 8/08* | (2006.01) | |
| *G01R 33/563* | (2006.01) | |
| *A61B 5/107* | (2006.01) | |
| *G06T 7/00* | (2017.01) | |
| *G06T 17/00* | (2006.01) | |
| *G06K 9/62* | (2006.01) | |
| *A61B 5/021* | (2006.01) | |
| *G06F 17/50* | (2006.01) | |
| *G06F 19/12* | (2011.01) | |
| *A61B 5/024* | (2006.01) | |
| *A61B 5/22* | (2006.01) | |
| *G06K 9/46* | (2006.01) | |
| *G06T 7/20* | (2017.01) | |
| *G06T 11/00* | (2006.01) | |
| *G06T 11/20* | (2006.01) | |
| *A61M 5/00* | (2006.01) | |
| *G06K 9/52* | (2006.01) | |
| *A61B 5/055* | (2006.01) | |
| *A61B 5/11* | (2006.01) | |
| *G06T 17/20* | (2006.01) | |
| *G06T 15/10* | (2011.01) | |
| *G06T 11/60* | (2006.01) | |
| *G06T 7/60* | (2017.01) | |
| *A61B 8/02* | (2006.01) | |
| *A61B 8/04* | (2006.01) | |
| *G06T 7/70* | (2017.01) | |
| *G06T 7/73* | (2017.01) | |
| *G06T 7/11* | (2017.01) | |
| *G06T 7/12* | (2017.01) | |
| *G06T 7/13* | (2017.01) | |
| *G06T 7/149* | (2017.01) | |
| *G06T 7/62* | (2017.01) | |
| *G01R 33/56* | (2006.01) | |
| *A61B 90/00* | (2016.01) | |

(52) U.S. Cl.
CPC .............. *A61B 5/0044* (2013.01); *A61B 5/02* (2013.01); *A61B 5/021* (2013.01); *A61B 5/024* (2013.01); *A61B 5/026* (2013.01); *A61B 5/02007* (2013.01); *A61B 5/029* (2013.01); *A61B 5/02028* (2013.01); *A61B 5/0263* (2013.01); *A61B 5/055* (2013.01); *A61B 5/1075* (2013.01); *A61B 5/1118* (2013.01); *A61B 5/22* (2013.01); *A61B 5/4848* (2013.01); *A61B 5/6852* (2013.01); *A61B 5/7246* (2013.01); *A61B 5/7275* (2013.01); *A61B 5/7278* (2013.01); *A61B 5/745* (2013.01); *A61B 6/03* (2013.01); *A61B 6/032* (2013.01); *A61B 6/481* (2013.01); *A61B 6/503* (2013.01); *A61B 6/504* (2013.01); *A61B 6/507* (2013.01); *A61B 6/5205* (2013.01); *A61B 6/5217* (2013.01); *A61B 6/5229* (2013.01); *A61B 8/02* (2013.01); *A61B 8/04* (2013.01); *A61B 8/06* (2013.01); *A61B 8/065* (2013.01); *A61B 8/481* (2013.01); *A61B 8/5223* (2013.01); *A61B 8/5261* (2013.01); *A61B 34/25* (2016.02); *A61M 5/007* (2013.01); *G01R 33/5601* (2013.01); *G01R 33/5635* (2013.01); *G01R 33/56366* (2013.01); *G06F 17/10* (2013.01); *G06F 17/5009* (2013.01); *G06F 17/5018* (2013.01); *G06F 19/12* (2013.01); *G06F 19/26* (2013.01); *G06F 19/321* (2013.01); *G06F 19/322* (2013.01); *G06F 19/324* (2013.01); *G06F 19/3431* (2013.01); *G06F 19/3437* (2013.01); *G06G 7/60* (2013.01); *G06K 9/00147* (2013.01); *G06K 9/46* (2013.01); *G06K 9/4604* (2013.01); *G06K 9/52* (2013.01); *G06K 9/6215* (2013.01); *G06K 9/6267* (2013.01); *G06K 9/6298* (2013.01); *G06T 7/0012* (2013.01); *G06T 7/0014* (2013.01); *G06T 7/11* (2017.01); *G06T 7/12* (2017.01); *G06T 7/13* (2017.01); *G06T 7/149* (2017.01); *G06T 7/20* (2013.01); *G06T 7/60* (2013.01); *G06T 7/62* (2017.01); *G06T 7/70* (2017.01); *G06T 7/73* (2017.01); *G06T 7/74* (2017.01); *G06T 11/00* (2013.01); *G06T 11/001* (2013.01); *G06T 11/008* (2013.01); *G06T 11/20* (2013.01); *G06T 11/60* (2013.01); *G06T 15/10* (2013.01); *G06T 17/00* (2013.01); *G06T 17/005* (2013.01); *G06T 17/20* (2013.01); *A61B 2034/104* (2016.02); *A61B 2034/105* (2016.02); *A61B 2034/107* (2016.02); *A61B 2034/108* (2016.02); *A61B 2090/374* (2016.02); *A61B 2090/3762* (2016.02); *A61B 2090/3764* (2016.02); *A61B 2576/00* (2013.01); *A61B 2576/023* (2013.01); *G06K 2009/4666* (2013.01); *G06T 2200/04* (2013.01); *G06T 2207/10012* (2013.01); *G06T 2207/10072* (2013.01); *G06T 2207/10081* (2013.01); *G06T 2207/10088* (2013.01); *G06T 2207/10104* (2013.01); *G06T 2207/10108* (2013.01); *G06T 2207/20036* (2013.01); *G06T 2207/20124* (2013.01); *G06T 2207/30048* (2013.01); *G06T 2207/30104* (2013.01); *G06T 2210/41* (2013.01); *G06T 2211/404* (2013.01)

(58) Field of Classification Search
CPC ...... A61B 2090/374; A61B 2090/3762; A61B 2090/3764; A61B 2576/00; A61B 2576/023; A61B 34/10; A61B 34/25; A61B 5/0035; A61B 5/004
See application file for complete search history.

(56) References Cited

U.S. PATENT DOCUMENTS

| | | |
|---|---|---|
| 5,151,856 A | 9/1992 | Halmann et al. |
| 5,205,289 A | 4/1993 | Hardy et al. |
| 5,235,510 A | 8/1993 | Yamada et al. |
| 5,582,173 A | 12/1996 | Li |
| 5,682,886 A | 11/1997 | Delp et al. |
| 5,687,208 A | 11/1997 | Bae et al. |
| 5,687,737 A | 11/1997 | Branham et al. |
| 5,729,670 A | 3/1998 | Strumolo et al. |
| 5,740,802 A | 4/1998 | Nafis et al. |
| 5,782,762 A | 7/1998 | Vining |
| 5,825,908 A | 10/1998 | Pieper et al. |
| 5,871,018 A | 2/1999 | Delp et al. |
| 5,920,319 A | 7/1999 | Vining et al. |
| 5,947,899 A | 9/1999 | Winslow et al. |
| 6,026,173 A | 2/2000 | Svenson et al. |
| 6,047,080 A | 4/2000 | Chen et al. |
| 6,083,162 A | 7/2000 | Vining |
| 6,117,087 A | 9/2000 | Kamm et al. |
| 6,169,917 B1 | 1/2001 | Masotti et al. |
| 6,176,838 B1 | 1/2001 | Sase |
| 6,236,878 B1 | 5/2001 | Taylor et al. |
| 6,272,366 B1 | 8/2001 | Vining |
| 6,278,460 B1 | 8/2001 | Myers et al. |
| 6,352,509 B1 | 3/2002 | Kawagishi et al. |
| 6,366,800 B1 | 4/2002 | Vining et al. |
| 6,379,041 B1 | 4/2002 | Schuetz et al. |
| 6,381,562 B2 | 4/2002 | Keane |
| 6,442,235 B2 | 8/2002 | Koppe et al. |
| 6,466,205 B2 | 10/2002 | Simpson et al. |
| 6,471,656 B1 | 10/2002 | Shalman |
| 6,487,432 B2 | 11/2002 | Slack |
| 6,501,848 B1 | 12/2002 | Carroll et al. |
| 6,503,202 B1 | 1/2003 | Hossack et al. |
| 6,507,753 B1 | 1/2003 | Xue et al. |
| 6,606,091 B2 | 8/2003 | Liang et al. |
| 6,628,743 B1 | 9/2003 | Drummond et al. |
| 6,650,724 B2 | 11/2003 | Strobel |
| 6,666,820 B1 | 12/2003 | Poole |
| 6,694,163 B1 | 2/2004 | Vining |
| 6,711,433 B1 | 3/2004 | Geiger et al. |
| 6,718,004 B2 | 4/2004 | Cesmeli |
| 6,720,966 B2 | 4/2004 | Barth et al. |
| 6,793,496 B2 | 9/2004 | Edic et al. |
| 6,801,643 B2 | 10/2004 | Pieper |
| 6,887,207 B2 | 5/2005 | Hettrick |
| 6,898,453 B2 | 5/2005 | Lee |
| 6,909,913 B2 | 6/2005 | Vining |
| 6,932,842 B1 | 8/2005 | Litschko et al. |
| 6,950,689 B1 | 9/2005 | Willis et al. |
| 6,996,262 B2 | 2/2006 | Li |
| 7,006,955 B2 | 2/2006 | Daft et al. |
| 7,121,832 B2 | 10/2006 | Hsieh et al. |
| 7,149,333 B2 | 12/2006 | Pieper et al. |
| 7,149,564 B2 | 12/2006 | Vining et al. |
| 7,182,602 B2 | 2/2007 | Lakin et al. |
| 7,191,110 B1 | 3/2007 | Charbel et al. |
| 7,229,412 B2 | 6/2007 | Jacob et al. |
| 7,286,866 B2 | 10/2007 | Okerlund et al. |
| 7,302,286 B2 | 11/2007 | Camus et al. |
| 7,321,677 B2 | 1/2008 | Evron et al. |
| 7,327,862 B2 | 2/2008 | Murphy et al. |
| 7,333,643 B2 | 2/2008 | Murphy et al. |
| 7,333,648 B2 | 2/2008 | Edic et al. |
| 7,343,196 B2 | 3/2008 | Okerlund et al. |
| 7,356,367 B2 | 4/2008 | Liang et al. |
| 7,369,691 B2 | 5/2008 | Kondo et al. |
| 7,371,067 B2 | 5/2008 | Anderson et al. |
| 7,462,153 B2 | 12/2008 | Bostian et al. |
| 7,474,776 B2 | 1/2009 | Kaufman et al. |
| 7,505,551 B2 | 3/2009 | Grass et al. |
| 7,526,112 B2 | 4/2009 | Murphy et al. |
| 7,536,042 B2 | 5/2009 | Murphy et al. |
| 7,539,529 B2 | 5/2009 | Schmitt et al. |
| 7,542,595 B2 | 6/2009 | Moreau-Gobard |
| 7,574,026 B2 | 8/2009 | Rasche et al. |
| 7,646,900 B2 | 1/2010 | Movassaghi et al. |
| 7,646,901 B2 | 1/2010 | Murphy et al. |
| 7,650,179 B2 | 1/2010 | Redel et al. |
| 7,693,563 B2 | 4/2010 | Suresh et al. |
| 7,725,164 B2 | 5/2010 | Suurmond et al. |
| 7,725,165 B2 | 5/2010 | Chen et al. |
| 7,738,626 B2 | 6/2010 | Weese et al. |
| 7,739,090 B2 | 6/2010 | Charbel et al. |
| 7,742,629 B2 | 6/2010 | Zarkh et al. |
| 7,747,055 B1 | 6/2010 | Vining et al. |
| 7,751,984 B2 | 7/2010 | Tang |
| 7,773,719 B2 | 8/2010 | Galant et al. |
| 7,773,785 B2 | 8/2010 | Murphy et al. |
| 7,792,565 B2 | 9/2010 | Vining |
| 7,792,593 B2 | 9/2010 | Rahn et al. |
| 7,805,177 B2 | 9/2010 | Chen et al. |
| 7,813,785 B2 | 10/2010 | Okerlund et al. |
| 7,853,310 B2 | 12/2010 | Vining et al. |
| 8,157,742 B2 | 4/2012 | Taylor |
| 8,315,812 B2 | 11/2012 | Taylor |
| 8,321,150 B2 | 11/2012 | Taylor |
| 8,831,320 B2 | 9/2014 | Bernhardt |
| 9,405,996 B2 | 8/2016 | Ionasec et al. |
| 2002/0002447 A1 | 1/2002 | Keane |
| 2002/0035458 A1 | 3/2002 | Kim et al. |
| 2002/0052553 A1 | 5/2002 | Shalman et al. |
| 2002/0118869 A1 | 8/2002 | Knoplioch |
| 2002/0120431 A1 | 8/2002 | Keane |
| 2003/0023266 A1 | 1/2003 | Borillo et al. |
| 2003/0123606 A1 | 7/2003 | Mollus et al. |
| 2004/0034309 A1 | 2/2004 | Pullan et al. |
| 2004/0044282 A1 | 3/2004 | Mixon et al. |
| 2004/0049115 A1 | 3/2004 | Murphy et al. |
| 2004/0064298 A1 | 4/2004 | Levine |
| 2004/0153128 A1 | 8/2004 | Suresh et al. |
| 2005/0010105 A1 | 1/2005 | Sra |
| 2005/0018885 A1 | 1/2005 | Chen et al. |
| 2005/0043609 A1 | 2/2005 | Murphy et al. |
| 2005/0059876 A1 | 3/2005 | Krishnan et al. |
| 2005/0064416 A1 | 3/2005 | Fishman et al. |
| 2005/0131663 A1 | 6/2005 | Bangs et al. |
| 2005/0272992 A1 | 12/2005 | O'Donnell et al. |
| 2006/0069318 A1 | 3/2006 | Keaveny et al. |
| 2006/0142984 A1 | 6/2006 | Weese et al. |
| 2006/0149522 A1 | 7/2006 | Tang |
| 2006/0166176 A1 | 7/2006 | Lakin et al. |
| 2006/0171585 A1 | 8/2006 | Rinck et al. |
| 2006/0235669 A1 | 10/2006 | Charbel et al. |
| 2006/0239528 A1 | 10/2006 | Camus et al. |
| 2006/0241445 A1 | 10/2006 | Altmann et al. |
| 2006/0241461 A1 | 10/2006 | White et al. |
| 2006/0253024 A1 | 11/2006 | Altmann et al. |
| 2006/0278245 A1 | 12/2006 | Gan |
| 2007/0014452 A1 | 1/2007 | Suresh et al. |
| 2007/0015996 A1 | 1/2007 | Camus et al. |
| 2007/0078325 A1 | 4/2007 | Fuimaono et al. |
| 2007/0078352 A1 | 4/2007 | Pijls |
| 2007/0135707 A1 | 6/2007 | Redel et al. |
| 2007/0163353 A1 | 7/2007 | Lec et al. |
| 2007/0219448 A1 | 9/2007 | Seip et al. |
| 2007/0231779 A1 | 10/2007 | Santhanam et al. |
| 2007/0232883 A1 | 10/2007 | Illegbusi |
| 2007/0238999 A1 | 10/2007 | Specht |
| 2007/0276214 A1 | 11/2007 | Dachille et al. |
| 2007/0293936 A1 | 12/2007 | Dobak, III |
| 2008/0004508 A1 | 1/2008 | Sun et al. |
| 2008/0020362 A1 | 1/2008 | Cotin et al. |
| 2008/0040087 A1 | 2/2008 | Watrous |
| 2008/0051660 A1 | 2/2008 | Kakadaris et al. |
| 2008/0058642 A1 | 3/2008 | Gould |
| 2008/0069419 A1 | 3/2008 | Farag |
| 2008/0097210 A1 | 4/2008 | Salgo et al. |
| 2008/0118121 A1 | 5/2008 | Skinner et al. |
| 2008/0118122 A1 | 5/2008 | Sirohey et al. |

(56) References Cited

U.S. PATENT DOCUMENTS

| | | |
|---|---|---|
| 2008/0177172 A1 | 7/2008 | John et al. |
| 2008/0205722 A1 | 8/2008 | Schaefer et al. |
| 2008/0208068 A1 | 8/2008 | Robertson et al. |
| 2008/0212857 A1 | 9/2008 | Pfister |
| 2008/0221442 A1 | 9/2008 | Tolkowsky et al. |
| 2008/0228086 A1 | 9/2008 | Ilegbusi et al. |
| 2008/0262346 A1 | 10/2008 | Assis et al. |
| 2008/0262814 A1 | 10/2008 | Zheng et al. |
| 2008/0269611 A1 | 10/2008 | Pedrizzetti et al. |
| 2008/0270095 A1 | 10/2008 | Lombaert et al. |
| 2008/0275336 A1 | 11/2008 | Deschamps et al. |
| 2008/0278492 A1 | 11/2008 | Ruijters et al. |
| 2008/0287812 A1 | 11/2008 | Parlikar et al. |
| 2008/0294038 A1 | 11/2008 | Weese et al. |
| 2008/0317310 A1 | 12/2008 | Suresh et al. |
| 2008/0319308 A1 | 12/2008 | Tang |
| 2009/0005672 A1 | 1/2009 | Sugiura |
| 2009/0008830 A1 | 1/2009 | Okazaki et al. |
| 2009/0012382 A1 | 1/2009 | Dutta |
| 2009/0016483 A1 | 1/2009 | Kawasaki et al. |
| 2009/0028289 A1 | 1/2009 | Tsuyuki et al. |
| 2009/0054774 A1 | 2/2009 | Njemanze |
| 2009/0074267 A1 | 3/2009 | Pedrizzetti et al. |
| 2009/0077681 A1 | 3/2009 | Fishman et al. |
| 2009/0088830 A1 | 4/2009 | Mohamed |
| 2009/0097731 A1 | 4/2009 | Sanada et al. |
| 2009/0156933 A1 | 6/2009 | Gerard et al. |
| 2009/0161938 A1 | 6/2009 | Shekhar et al. |
| 2009/0177454 A1 | 7/2009 | Bronstein et al. |
| 2009/0221907 A1 | 9/2009 | Bar-Tal |
| 2009/0244061 A1 | 10/2009 | De Putter et al. |
| 2009/0281423 A1 | 11/2009 | Sirohey et al. |
| 2009/0281434 A1 | 11/2009 | Messerges |
| 2009/0287135 A1 | 11/2009 | Michishita et al. |
| 2009/0292206 A1 | 11/2009 | Sato |
| 2009/0292349 A1 | 11/2009 | Golesworthy |
| 2009/0292557 A1 | 11/2009 | Sirohey |
| 2009/0310840 A1 | 12/2009 | Mohamed et al. |
| 2009/0322749 A1 | 12/2009 | Kassab et al. |
| 2009/0324052 A1 | 12/2009 | Nowinski |
| 2010/0002925 A1 | 1/2010 | Kiraly et al. |
| 2010/0017171 A1 | 1/2010 | Spilker et al. |
| 2010/0041981 A1 | 2/2010 | Kassab |
| 2010/0053209 A1 | 3/2010 | Rauch et al. |
| 2010/0067760 A1 | 3/2010 | Zhang et al. |
| 2010/0070249 A1 | 3/2010 | Ionasec et al. |
| 2010/0081917 A1 | 4/2010 | Zhang et al. |
| 2010/0086099 A1 | 4/2010 | Kuzmanovic |
| 2010/0125197 A1 | 5/2010 | Fishel |
| 2010/0130878 A1 | 5/2010 | Lasso et al. |
| 2010/0152570 A1 | 6/2010 | Navab |
| 2010/0156898 A1 | 6/2010 | Voros et al. |
| 2010/0172554 A1 | 7/2010 | Kassab et al. |
| 2010/0183206 A1 | 7/2010 | Carlsen et al. |
| 2010/0189337 A1 | 7/2010 | Jandt et al. |
| 2010/0241404 A1 | 9/2010 | Taylor et al. |
| 2010/0265251 A1 | 10/2010 | Vining et al. |
| 2010/0266176 A1 | 10/2010 | Masumoto et al. |
| 2010/0272315 A1 | 10/2010 | Tsin et al. |
| 2010/0278405 A1 | 11/2010 | Kakadiaris et al. |
| 2010/0280352 A1 | 11/2010 | Ionasec et al. |
| 2010/0298719 A1 | 11/2010 | Kock et al. |
| 2010/0299077 A1 | 11/2010 | Kassab et al. |
| 2010/0328305 A1 | 12/2010 | Vining |
| 2011/0060576 A1 | 3/2011 | Sharma et al. |
| 2011/0071404 A1 | 3/2011 | Schmitt et al. |
| 2011/0085977 A1 | 4/2011 | Rosenmeire |
| 2011/0131167 A1 | 6/2011 | Achterberg |
| 2011/0152599 A1 | 6/2011 | Bokeriya et al. |
| 2011/0178383 A1 | 7/2011 | Kassab |
| 2011/0178417 A1 | 7/2011 | Kassab |
| 2011/0275934 A1 | 11/2011 | Kassab |
| 2011/0275936 A1 | 11/2011 | Cho et al. |
| 2011/0282586 A1 | 11/2011 | Kassab et al. |
| 2012/0022843 A1 | 1/2012 | Ionasec et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt et al. |
| 2012/0122777 A1 | 5/2012 | Daimon et al. |
| 2012/0150516 A1 | 6/2012 | Taylor et al. |
| 2012/0243761 A1 | 9/2012 | Senzig et al. |
| 2013/0060133 A1 | 3/2013 | Kassab et al. |
| 2013/0090555 A1 | 4/2013 | Kassab |
| 2013/0132054 A1 | 5/2013 | Sharma et al. |
| 2013/0197884 A1 | 8/2013 | Mansi et al. |
| 2013/0226003 A1 | 8/2013 | Edic et al. |
| 2013/0246034 A1 | 9/2013 | Sharma et al. |
| 2013/0324842 A1 | 12/2013 | Mittal et al. |
| 2014/0029835 A1 | 1/2014 | Kim et al. |
| 2014/0073976 A1 | 3/2014 | Fonte et al. |
| 2014/0148693 A1 | 5/2014 | Taylor |
| 2014/0200867 A1 | 7/2014 | Lavi et al. |
| 2014/0243663 A1 | 8/2014 | Taylor |
| 2014/0249399 A1 | 9/2014 | Sharma et al. |
| 2015/0065864 A1 | 3/2015 | Sharma et al. |
| 2015/0112191 A1 | 4/2015 | Gilboa et al. |
| 2015/0265162 A1 | 9/2015 | Lavi |
| 2015/0297161 A1 | 10/2015 | Grass |
| 2015/0342551 A1 | 12/2015 | Lavi |
| 2015/0356734 A1 | 12/2015 | Ooga |
| 2016/0022371 A1 | 1/2016 | Sauer |

FOREIGN PATENT DOCUMENTS

| | | |
|---|---|---|
| EP | 1125548 A1 | 8/2001 |
| EP | 1 182 619 A2 | 2/2002 |
| EP | 1 225 541 A2 | 7/2002 |
| EP | 1 482 470 A2 | 12/2004 |
| EP | 1 492 071 A1 | 12/2004 |
| EP | 0 961 993 B1 | 2/2005 |
| EP | 1 717 758 A2 | 11/2006 |
| EP | 1 717 759 A1 | 11/2006 |
| EP | 1 961 384 A1 | 8/2008 |
| EP | 1 967 140 A1 | 9/2008 |
| EP | 2 028 608 A2 | 2/2009 |
| EP | 2028606 A1 | 2/2009 |
| EP | 2 138 091 A1 | 12/2009 |
| EP | 2278597 | 1/2011 |
| EP | 2 302 594 A2 | 3/2011 |
| EP | 2 302 595 A2 | 3/2011 |
| EP | 2 302 596 A1 | 3/2011 |
| JP | 2000515789 A | 11/2000 |
| JP | 2002/501774 | 1/2002 |
| JP | 2002-513601 | 5/2002 |
| JP | 2003508152 A | 3/2003 |
| JP | 2003525067 A | 8/2003 |
| JP | 2006230482 A | 9/2006 |
| JP | 2007135894 | 6/2007 |
| JP | 2007517633 A | 7/2007 |
| JP | 2008-126077 | 5/2008 |
| JP | 2004-528858 A | 9/2008 |
| JP | 2009-515584 | 4/2009 |
| JP | 2009540767 A | 11/2009 |
| JP | 2011-40055 A | 2/2011 |
| JP | 2012501218 A | 1/2012 |
| JP | 2013-505782 A | 2/2013 |
| KR | 1020070026135 | 3/2007 |
| KR | 1020070120957 | 12/2007 |
| KR | 10-2009-0093877 | 9/2009 |
| KR | 10200900988839 | 9/2009 |
| WO | WO 94/08315 A1 | 4/1994 |
| WO | WO 95/26682 A1 | 10/1995 |
| WO | WO 96/38815 A1 | 12/1996 |

(56) References Cited

FOREIGN PATENT DOCUMENTS

| | | |
|---|---|---|
| WO | WO 96/41567 A2 | 12/1996 |
| WO | WO 97/17894 A1 | 5/1997 |
| WO | WO 97/49065 A1 | 12/1997 |
| WO | 9804182 A2 | 2/1998 |
| WO | WO 98/11524 A1 | 3/1998 |
| WO | WO 98/32371 A1 | 7/1998 |
| WO | WO 98/43201 A1 | 10/1998 |
| WO | WO 99/38433 A1 | 8/1999 |
| WO | WO 99/42977 A1 | 8/1999 |
| WO | WO 99/56612 | 11/1999 |
| WO | WO 99/63887 A1 | 12/1999 |
| WO | WO 00/07501 A1 | 2/2000 |
| WO | WO 00/32106 A1 | 6/2000 |
| WO | 0053081 A1 | 9/2000 |
| WO | WO 00/55812 A1 | 9/2000 |
| WO | WO 00/55814 A2 | 9/2000 |
| WO | WO 00/68749 A1 | 11/2000 |
| WO | WO 00/72272 A1 | 11/2000 |
| WO | 0117456 A1 | 3/2001 |
| WO | WO 01/22362 A1 | 3/2001 |
| WO | WO 01/85030 A1 | 11/2001 |
| WO | WO 02/29758 A2 | 4/2002 |
| WO | WO 02/29764 A1 | 4/2002 |
| WO | WO 02/095686 A1 | 11/2002 |
| WO | WO 03/034336 A2 | 4/2003 |
| WO | WO 03/060553 A2 | 7/2003 |
| WO | WO 03/081529 A1 | 10/2003 |
| WO | WO 2004/010374 A2 | 1/2004 |
| WO | WO 2004/012152 A2 | 2/2004 |
| WO | WO 2004/066807 A2 | 8/2004 |
| WO | WO 2004/068406 A2 | 8/2004 |
| WO | WO 2004/072903 A2 | 8/2004 |
| WO | WO 2005/004038 A1 | 1/2005 |
| WO | WO 2005/004721 A1 | 1/2005 |
| WO | WO 2005/027765 A1 | 3/2005 |
| WO | WO 2005/031635 A1 | 4/2005 |
| WO | WO 2005/083633 A2 | 9/2005 |
| WO | WO 2005/119578 A2 | 12/2005 |
| WO | WO 2006/002353 A2 | 1/2006 |
| WO | WO 2006/020920 A2 | 2/2006 |
| WO | WO 2006/061815 A1 | 6/2006 |
| WO | WO 2006/066122 A2 | 6/2006 |
| WO | WO 2006/079042 A2 | 7/2006 |
| WO | WO 2006/082558 A2 | 8/2006 |
| WO | WO 2007/020555 A2 | 2/2007 |
| WO | WO 2007/066249 A2 | 6/2007 |
| WO | WO 2007/102858 A1 | 9/2007 |
| WO | 2007146930 A2 | 12/2007 |
| WO | WO 2008/030192 A1 | 3/2008 |
| WO | WO 2009/007910 A2 | 1/2009 |
| WO | WO 2009/056147 A1 | 5/2009 |
| WO | 2010020933 A2 | 2/2010 |
| WO | WO 2010/033971 | 3/2010 |
| WO | 2010061335 A1 | 6/2010 |
| WO | 2011015822 A1 | 2/2011 |
| WO | WO 2011/038044 A2 | 3/2011 |
| WO | 2012021307 A2 | 2/2012 |

OTHER PUBLICATIONS

Ellwein, Laura M., et al., "Sensitivity Analysis and Model Assessment: Mathematical Models for Arterial Blood Flow and Blood Pressure," Cardiovasc Eng. Jun. 2008;8(2):94-108.
Spilker, Ryan L., et al., "Morphometry-Based Impedance Boundary Conditions for Patient-Specific Modeling of Blood Flow in Pulmonary Arteries," Annals of Biomedical Engineering, 2007, 35:546-559.
Santamarina, Aland, et al., "Computational Analysis of Flow in a Curved Tube Model of the Coronary Arteries: Effects of Time-Varying Curvature," Annals of Biomedical Engineering, 1998, 26:944-954.
Boutsianis, Evangelos, et al., "Computational Simulation of Intracoronary Flow Based on Real Coronary Geometry," European Journal of Cardio-thoracic Surgery, 2004, 26:248-256.
Quarteroni, Alfio, et al., "Coupling Between Lumped and Distributed Models for Blood Flow Problems," Comput Visual Sci, 2001, 4:111-124.
Berry, Joel L., et al., "Experimental and Computational Flow Evaluation of Coronary Stents," Annals of Biomedical Engineering, 2000, 28:386-398.
Myers, J.G., et al., "Factors Influencing Blood Flow Patterns in the Human Right Coronary Artery," Annals of Biomedical Engineering, 2001, 29:109-120.
Lagana, Katia, et al., "Multiscale Modeling of the Cardiovascular System: Application to the Study of Pulmonary and Coronary Perfusions in the Univentricular Circulation," Journal of Biomechanics, 2005, 38:1129-1141.
Qiu, Yuchen, et al., "Numerical Simulation of Pulsatile Flow in a Compliant Curved Tube Model of a Coronary Artery," Journal of Biomechanical Engineering, 2000, 122:77-85.
Formaggia, L., et al., "Numerical Treatment of Defective Boundary Conditions for the Navier-Stokes Equations," SIAM J. Numer. Anal., 2002, 40(1):376-401.
Gijsen, Frank J.H., et al., "Strain Distribution Over Plaques in Human Coronary Arteries Relates to Shear Stress," Am J Physiol Heart Circ Physiol, 2008, 295:H1608-H1614.
Perktold, K., et al., "Validated Computation of Physiologic Flow in a Realistic Coronary Artery Branch," Journal of Biomechanics, 1998, 31:217-228.
Taylor, Charles A., et al., "Open Problems in Computational Vascular Biomechanics: Hemodynamics and Arterial Wall Mechanics," Comput. Methods Appl. Mech. Engrg., 2009, 198:3514-3523.
Taylor, Charles A., et al., "Patient-Specific Modeling of Cardiovascular Mechanics," Annu. Rev. Biomed. Eng., 2009, 11:109-134.
Taylor, Charles A., et al., "Image-Based Modeling of Blood Flow and Vessel Wall Dynamics: Applications, Methods and Future Directions," Annals of Biomedical Engineering, Mar. 2010, vol. 38, No. 3, pp. 1188-1203.
Spilker, Ryan L., et al., "Tuning Multidomain Hemodynamic Simulations to Match Physiological Measurements," Annals of Biomedical Engineering, Aug. 2010, vol. 38, No. 8, pp. 2635-2648.
U.S. Appl. No. 61/210,401 to Charles A. Taylor et al. titled "Patient-Specific Hemodynamics of the Cardiovascular System," filed Mar. 17, 2009.
Spilker, Ryan L., et al., "Models and Methods in Computational Vascular and Cardiovascular Mechanics," 9th U.S. National Congress on Computational Mechanics, 2007, 1 page.
Spilker, Ryan L., et al., "Tuning Hemodynamic Simulations With Three-Element Windkessel Outlet Boundary Conditions," Jul. 24, 2007, 32 pages.
Taylor, Charles A., "The HeartFlow Concept Combining Angiographic Imaging and Non-invasive Hemodynamic Lesion Assessment: Technology Description," Transcatheter Cardiovascular Therapeutics (TCT) Conference 2010, Sep. 21, 2010, 12 pages.
Erglis, Andrejs, et al., "Non-invasive FFR Using Coronary CT Angiography and Computational Fluid Dynamics Predicts the Hemodynamic Significance of Coronary Lesions," Aug. 29, 2010, 19 pages.
Taylor, Charles A., et al., "Predictive Medicine: Computational Techniques in Therapeutic Decision-Making," Computer Aided Surgery, 1999, 4:231-247.
Taylor, Charles A., et al., "Computational Investigations in Vascular Disease," Computers in Physics, vol. 10, No. 3, May/Jun. 1996, pp. 224-232.
Taylor, Charles A., "A Computational Framework for Investigating Hemodynamic Factors in Vascular Adaptation and Disease," Aug. 1996, 118 pages.
Wang, Kenneth C., "Improving Geometric Model Construction for Blood Flow Modeling," IEEE Engineering in Medicine and Biology, Nov./Dec. 1999, pp. 33-39.
Pijls, N., et al., "Measurement of Fractional Flow Reserve to Assess the Functional Severity of Coronary-Artery Stenoses," The New England Journal of Medicine, Jun. 27, 1996, pp. 1703-1708, vol. 334, No. 26.
Kim, H.J., et al., "Patient-Specific Modeling of Blood Flow and Pressure in Human Coronary Arteries," Annals of Biomedical Engineering, pp. 3195-3209, vol. 38, No. 10, Oct. 2010.

(56) References Cited

OTHER PUBLICATIONS

Kim, H.J., et al., "Coronary Outflow Boundary Condition Coupling Lumped Parameter Coronary Vascular Bed and Heart Models for Three-Dimensional Simulations of Blood Flow," Presented at the Fifth International Biofluids Symposium and Workshop, Pasadena, CA, Mar. 28-30, 2008.

Fischer, A., et al., "Predicting plaque rupture: enhancing diagnosis and clinical decision-making in coronary artery disease," Vascular Medicine 2000, 5:163-172.

Malek, A. M., et al., "Hemodynamic Shear Stress and Its Role in Atherosclerosis," JAMA, Dec. 1, 1999, vol. 282, No. 21, pp. 2035-2042.

Bekkers, E. J., et al., "Multiscale Vascular Surface Model Generation From Medical Imaging Data Using Hierarchical Features," IEEE Transactions on Medical Imaging, vol. 27, No. 3, Mar. 2008, pp. 331-341.

Ku, J. P., et al., "In Vivo Validation of Numerical Prediction of Blood Flow in Arterial Bypass Grafts," Annals of Biomedical Engineering, vol. 30, pp. 743-752, 2002.

Marshall et al., "Use of a Secure Internet Web Site for Collaborative Medical Research," JAMA, Oct. 11, 2000, vol. 284, No. 14, pp. 1843-1849.

Kim, H.J. et al. "On Coupling a Lumped Parameter Heart Model and a Three-Dimensional Finite Element Aorta Model," Annals of Biomedical Engineering, vol. 37, No. 11, Nov. 2009, pp. 2153-2169.

Steinman, D. A., "Image-Based Computational Fluid Dynamics Modeling in Realistic Arterial Geometries," Annals of Biomedical Engineering, vol. 30, pp. 483-497, 2002.

Vignon-Clementel, I. E., et al., "Outflow boundary conditions for three-dimensional finite element modeling of blood flow and pressure in arteries," Comput. Methods Appl. Mech. Engrg. 195, 2006, pp. 3776-3796.

Office Action dated Apr. 11, 2012, for U.S. Appl. No. 13/014,835, (24 pages).

Office Action dated Apr. 16, 2012, for U.S. Appl. No. 13/014,841, (26 pages).

Office Action dated Apr. 18, 2012, for U.S. Appl. No. 13/014,845, (27 pages).

Office Action dated Apr. 19, 2012, for U.S. Appl. No. 13/014,850, (28 pages).

Office Action dated Apr. 12, 2012, for U.S. Appl. No. 13/014,857, (24 pages).

Office Action dated Mar. 13, 2012, for U.S. Appl. No. 13/290,641, (30 pages).

Office Action dated Feb. 3, 2012, for U.S. Appl. No. 13/290,476, (15 pages).

Office Action dated Jan. 26, 2012, for U.S. Appl. No. 13/290,842, (22 pages).

Office Action dated Feb. 23, 2012, for U.S. Appl. No. 13/013,561, (26 pages).

Office Action dated Apr. 4, 2012, for U.S. Appl. No. 12/661,491, (15 pages).

Office Action dated May 1, 2012, for U.S. Appl. No. 13/290,842, (18 pages).

Office Action dated May 11, 2012, for U.S. Appl. No. 13/291,089, (26 pages).

Office Action dated May 25, 2012, for U.S. Appl. No. 13/291,077, (19 pages).

Office Action dated Jun. 22, 2012, for U.S. Appl. No. 13/014,829, (21 pages).

Office Action dated Jun. 29, 2012, for U.S. Appl. No. 13/013,561, (15 pages).

Office Action dated Jul. 3, 2012, for U.S. Appl. No. 13/290,641, (13 pages).

Office Action dated Apr. 8, 2013, for U.S. Appl. No. 13/014,809, (18 pages).

Office Action dated Apr. 22, 2013, for U.S. Appl. No. 13/014,821, (28 pages).

Hamada, M. et al., "Shinkakudai no hasseikijo (mechanism of development of heart enlargement)," Modern Physician, Shinkoh-IgakuShuppan Co., Ltd, 1997, vol. 17, No. 8, pp. 967-970.

Arkilic et al., "Mass Flow and Tangential Momentum Accommodation in Silicon Micromachined Channels," J. Fluid Mech., 2001, vol. 437, pp. 29-43.

Shalman, E. et al., "Pressure-based Simultaneous CFR and FFR Measurements: Understanding the Physiology of a Stenosed Vessel," Computers in Biology and Medicine, 2001, vol. 31, pp. 353-363.

Lim, C.Y. et al., "Application of Lattice Boltzmann Method to Simulate Microchannel Flows," Physics of Fluids, 2002, vol. 14, No. 7, pp. 2299-2308.

Ryuu, H., Multi-scale Simulation of Circulatory System, Journal of the Japan Society of Precision Engineering, 2005, vol. 71, No. 12, pp. 1492-1497.

Frauenfelder, T., et al., "In-vivo Flow Simulation in Coronary Arteries Based on Computed Tomograpy Data Sets; Feasibility and Initial Results," European Radiology, Springer-Verlag, vol. 17, Issue 5, 2007, pp. 1291-130.

Yin W., et al., "3D numerical simulation of coronary blood flow and its effect on endothelial cell activation," Engineering in Medicine and Biology Society, 2009, $31^{st}$ Annual International Conference of the IEEE EMBS, pp. 4003-4006.

Wong, J.T. et al., "Determination of fractional flow reserve (FFR) based on scaling laws: a simulation study," 2008, Phys. Med. Biol. 53, pp. 3995-4011.

Shalman, E. et al., "Numerical modeling of the flow in stenosed coronary artery. The relationship between main hemodynamic parameters," 2002, Computers in Biology and Medicine 32, pp. 329-344.

Benson et al., "Percutaneous Implantation of a Balloon-Expandable Endoprosthesis for Pulmonary Artery Stenosis: An Experimental Study," Nov. 1, 1991, JACC, vol. 18, No. 5, pp. 1303-1308.

Chambers et al., "The Peak to Mean Pressure Decrease Ratio: A New Method of Assessing Aortic Stenosis," Jun. 2005, Journal of the American Society of Echocardiography, vol. 18, No. 6, pp. 674-678.

Nagai, Hiroyuki et al., "Advance in Imaging-Technology for Cardiac Area Analysis", The Institute of Electronics Information and Communication Engineers Technical Report, Iryogazo, 2007, vol. 106, No. 510, pp. 147-149.

Yokoi, Hiroyoshi et al., Teiryoteki Kandomyaku Zoei (QCA) no Genjo to Shorai: translated as Current state and future of Quantitative Coronary Angiography), Journal of a Measurement Subcommittee, Japanese Society of Radiological Technology, 2001, vol. 9, No. 1, pp. 14-20.

Ohashi, Tsuyoshi et al., Computational analysis of the Stress and Strains with in an Atherosclerotic Plaque Exerted by Interaction Between the Blood Flow and the Vessel Wall Structure, Proceedings of the JSME Bioengineering Conference and Seminar, The Japan Society of Mechanical Engineers, 2000, No. 11, pp. 103-104.

Alfio, Quarteroni, "On the Mathematical Modeling of the Cardiovascular System" ("Invited Lectures" in the $12^{th}$ JSIAM Annual Meeting), Bulletin of the Japan Society for Industrial and Applied Mathematics, The Japan Society for Industrial and Applied Mathematics, 2003, vol. 13, No. 1, pp. 79-82.

Tu, Rong et al., "3D reconstruction of coronary arteries from two X-ray angiograms based on anatomic model", Fifth International Conference on Photonics and Imaging in Biology and Medicine, Proceeding of the International Society for Optics and Photonics, 2007, vol. 6534, 8 pgs.

Li, Qin et al., "How to Reconstruct 3D Coronary Arterial Tree from Two Arbitrary Views"; Dept. of Opto-electronic Engineering, Beijing Institute of Technology, Beijing, 100081, P.R. China, © 2009 IEEE, 4 pgs.

Cilla, Myriam, et al., "Machine Learning Techniques as a Helpful Tool Toward Determination of Plaque Vulnerability"; IEEE Transactions on Biomedical Engineering, vol. 59, No. 4, Apr. 2012 , 7 pgs.

Latifoglu, Fatma, et al., Medical diagnosis of Atherosclerosis from Carotid Artery Doppler Signals using Principal Component Analysis (PCA), k-NN based weighting pre-processing and Artificial

(56) References Cited

OTHER PUBLICATIONS

Immune Recognition system (AIRS); ScienceDirect, Journal of Miomedical Informatics 41 (2008) 15-23, 9 pgs.
Motoyama, Sadako, et al., "Computed Tomographic Angiography Characteristics of Atherosclerotic Plaques Subsequently Resulting in Acute Coronary Syndrome"; Journal of the American College of Cardiology; © 2009 by the American College of Cardiology Foundation, vol. 54, No. 1, 2009, 9 pgs.
Himeno, Ryutaro, Blood Flow Simulation and its application to Medical Treatment, Journal of the Japan Society of Precision Engineering, 2005, vol. 71, No. 4, pp. 427-430.
Hyojun Byorigaku [translated as Standard Pathology] 4th Ed. (published on Aug. 1, 2010), Atsuhiko Sakamoto, Masanobu Kitagawa, Toshiro Niki (Ed.), Igaku Shoin Ltd, p. 324-330.
Byorigaku-Rinsho, Rubin Igaku heno Kiban—[translated as Pathology-Foundation for Clinical Medicine] (published on Nov. 6, 2007), Emanuel Rubin (Ed.), Toshimitsu Suzuki, Hideo Nakamura, Masahisa Fukayama, Mitsutoku Yamakawa, Tadashi Yoshino (translation supervisor), Nishimura Co, Ltd, p. 426-432.
Hyojun Byorigaku [translated as Standard Pathology] 4th Ed. (published on Aug. 1, 2010), Atsuhiko Sakamoto, Masanobu Kitagawa, Toshiro Niki (Ed.), Igaku Shoin Ltd, p. 345-349.
Wilson, N M et al: "An Integrated Software System for Preoperatively Evaluating Aorto-Femoral Reconstruction Procedures", Summer Bioengineering Conference Sonesta Beach Resort in Key Biscayne, Jun. 25, 2003 (Jun. 25, 2003), pp. 899-900.
Steele et al., "In vivo Validation of a One-Dimensional Finite-Element Method for Predicting Blood Flow in Cardiovascular Bypass Grafts", IEEE Transactins on Biomedical Engineering, vol. 50, No. 6, Jun. 2003, pp. 649-656.
Steinman et al., "Flow Imaging and Computing: Large Artery Hemodynamics", Dec. 2005, Annals of Biomedical Engineering, vol. 33, No. 12, pp. 1704-1709.
Wilson et al., "A Software Framework for Creating Patient Specific Geometric Models from Medical Imaging Data for Simulation Based Medical Planning of Vascular surgery," 2001, Medical Image Computing and Computer-Assisted Intervention—MICCAI 2001 ; pp. 449-456.
Botman, et al., "Percutaneous Coronary Intervention or ByPass Surgery in Multivessel Disease: A tailored approach based on Coronary Pressure Measurement;" 2004 Catheter. Cardiovasc. Interv., 63:184-191.
Termeer et al., "Visualization of Myocardial Perfusion Derived from Coronary Anatomy", 2008 IEEE Trans. Visual Comp. Graph 14:1595-1602.
Pijls et al., "Percutaneous Coronary Intervention of Functionally Nonsignificant Stenosis", 2007 J. Am. Col. Cardiol. 49:2105-2111.
Olufsen, Mett S., "On Deriving Lumped Models for Blood Flow and Pressure in the Systemic Arteries", Mathematical Biosciences and Engineering, vol. 1, No. 1, Jun. 2004 (pp. 61-80).
Bishop, et al. "Fractional flow reserve Critical review of an important physiologic adjunct to angiography", 2004 Am. Heart J. 147:792-802.
Lee et al. "Quantification of Absolute Myocardial Blood Flow by Magnetic Resonance Perfusion Imaging", 2009 J.A.C.C., Cardiovascular Imaging 2:761-770.
Choy et al., "Scaling of myocardial mass to flow and morphometry of coronary arteries", 2008 J. Appl. Physiol, 104:1281-1286.
Kassab et al., "Morphometry of pig coronary arterial trees". 1993 Am. J. Physiol. 265:H350-H365.
"Mathematical Optimization", Sep. 30, 2009, Wikipedia, <https://en.wikipedia.org/wiki/Mathematicl_optimization>.
Lee, K.W. et al. "Ultrasound image-based computer model of a common carotid artery with a plaque", Medical Engineering & Physics, Butterworth-Heinemann, GB, vol. 26, No. 10, Nov. 5, 2004 (Nov. 5, 2004), pp. 823-840, XP004656239, ISSN: 1350-4533, DOI, 10.1016/J. Medengphy.2004.08.013.
Singh et al., "The role of computational fluid dynamics in the management of unruptured intracranial aneurysms: A clinicians's view", Feb. 11, 2009.

Spilker, R.L.: "Computational analysis of blood flow in arteries incorporating reduced-order models of the downstream vasculature", Dissertation Jun. 2009; retrieved from URL:http://search.proquest.com/docview/30499618?accountid=29404.
Kristensen et al., "Correlation between coronary computed tomographic angiography and fractional flow reserve"; International Journal of Cardiology (2010) vol. 144:200-205; available online May 9, 2009.
Kurita et al., "Regional myocardial perfusion reserve determined using myocardial perfusion magnetic resonance imaging showed a direct correlation with coronary flow velocity reserve by Doppler flow wire"; European Heart Journal (2009) 30. pp. 444-452.
Pereztol-Valdes et al., "Correspondence between left ventricular 17 myocardial segments and coronary arteries"; European Heart Journal (2005) 26, pp. 2637-2643.
Kim et al., "Three-dimensional finite element modeling of blood flow in the coronary arteries"; $8^{th}$ world Congress on Computational Mechanics (WCCM8); ECCOMAS 2008; Jun. 30-Jul. 5, 2008, Venice, Italy; 2 pages.
Tang et al., "Local maximal stress hypothesis and computational plaque vulnerability index for atherosclerotic plaque assessment"; Annals of Biomedical Engineering, vol. 33, No. 12, Dec. 2005; pp. 1789-1801.
Le et al., "Estimation of regional myocardial mass at risk based on distal arterial umen volume and length using 3D micro-CT images"; NIH Public Access; Comput Med Imaging Graph, Sep. 2008; 32(6); pp. 488-501.
Narbeh Melikian et al. "Fractional Flow Reserve and Myocardial Perfusion Imaging in Patients with Angiographic Multivessel Coronary Artery Disease." J Am Coll Cardio Intv. Mar. 2010; 3(3):307-314.
Morris, Paul D. et al., "Virtual Fractional Flow Reserve From Coronary Angiography: Modeling the Significance of Coronary Lesions." J AmColl Cardiol Intv. Feb. 2013;6(2): 149-157.
Jingwu Yao et al., "Image-Based Fractional Flow Reserve Using Coronary Angiography," 2013 IEEE Nuclear Science Symposium and Medical Imaging Conference (2013 NSS/MIC).
Schroeder, T., "Cerebral Hyperfusion Following Carotid Endarterectomy"; J. Neurosurg./vol. 66/Jun. 1987; pp. 824-829.
Schwarz, S., "Effects of Induced Hypertension on Intracranial Pressure and Flow Velocities of the Middle Cerebral Arteries in Patients with Large Hemispheric Stroke"; Stroke 33.4 (2002): 998-1004.
Figueroa, C.A., "A Coupled-momentum Method to Model Blood Flow and Vessel Deformation in Human Arteries: Applications in Disease Research and Simulation-Based Medical Planning"; A Dissertation submitted to the Dept. of Mechanical Engineering and the Comm. on Graduate Studies of Stanford University, copyright 2006.
Forster et al.; Tc-99m sestamibi Single Photon Emission Computed Tomography for Guiding Percutaneous Coronary Intervention in Patients with Multivessel Disease: A comparison with quantitative coronary angiography and fractional flow reserve; 2010 Int. J. Cardiovasc. Imaging 26:pp. 203-213, ePub Sep. 16, 2009.
Watkins et al.; "Validation of Magnetic Resonance Myocardial Perfusion Imaging with Fractional Flow Reserve for the Detection of Significant Coronary Heart Disease"; 2009 Circulation 120: pp. 2207-2213.
Wood et al.; "Combined MR Imaging and CFD Simulation of Flow in the Human Descending Aorta", Journal of Magnetic Resonance Imaging, 13:699-713 (2001) pp. 699-713.
Nagel et al., "Magnetic Resonance Perfusion Measurements for the Noninvasive Detection of Coronary Artery Disease"; Circulation (2003), vol. 108, pp. 432-437.
Chen et al. "Lattice Boltzmann Method for Fluid Flows"; Annual Review Fluid Mech. 1998. 30. pp. 329-364.
Neal, et al., "Current Progress in Patient-Specific Modeling", Briefings in Bioinformatics, vol. II, No. I, pp. 111-226, Advance Access published on Dec. 2, 2009.
Al-Saadi et al., Noninvasive Detection of Myocardial Ischemia from Perfusion Reserve Based on Cardiovascular Magnetic Resonance; Circulation 101(12), 1379-1383. Mar. 28, 2000.

(56) References Cited

OTHER PUBLICATIONS

Pinciroli et al., A system for the Integration of Angiocardiographic Data and Images by an Object-Oriented DBMS; Computers and Biomedical Research 28, 5-23 (1995).

Anderson H.V., et al., "Coronary Artery Flow Velocity is Related to Lumen Area and Regional Left Ventricular Mass," Circulation, 2000, vol. 102 (1), pp. 48-54.

Bernhard S., et al., "Transient Integral Boundary Layer Method to Calculate the Translesional Pressure Drop and the Fractional Flow Reserve in Myocardial Bridges," BioMedical Engineering OnLine, 2006, vol. 5, 42 pages.

Bottcher M., et al., "Effect of Oral Nitroglycerin and Cold Stress on Myocardial Perfusion in Areas Subtended by Stenosed and Nonstenosed Coronary Arteries," American Journal of Cardiology, 2002, vol. 89 (9), pp. 1019-1024.

Deschamps T., et al., "Vessel Segmentation and Blood Flow Simulation Using Level-Sets and Embedded Boundary Methods," International Congress Series, 2004, vol. 1268, pp. 75-80.

European Search Report for Application No. EP14189381, dated Feb. 16, 2015, 8 pages.

European Search Report for Application No. EP15178021, dated Oct. 30, 2015, 8 pages.

Final Office Action dated May 1, 2012 for U.S. Appl. No. 13/290,842, filed Nov. 7, 2011.

Lesage D., et al., "A Review of 3d Vessel Lumen Segmentation Techniques: Models, Features and Extraction Schemes," Medical Image Analysis, 2009, vol. 13 (6), pp. 819-845.

Leuprecht A., et al., "Blood Flow in the Human Ascending Aorta: a Combined MRI and CFD Study," Journal of Engineering Mathematics, 2003, vol. 47 (3), pp. 387-404.

Liu D., et al., "Computational Analysis of Oxygen Transport in the Retinal Arterial Network," Current Eye Research, 2009, vol. 34 (11), pp. 945-956.

Olufsen M.S., et al., "Modeling Heart Rate Regulation—Part I: Sit-to-Stand Versus Head-Up Tilt," Cardiovascular Engineering—An International Journal, 2008, vol. 8 (2), pp. 73-87.

Partial European Search Report for Application No. EP14189383, dated May 26, 2015, 8 pages.

Pekkan K., et al., "Patient-Specific Surgical Planning and Hemodynamic Computational Fluid Dynamics Optimization Through Free-Form Haptic Anatomy Editing Tool (SURGEM)," Medical and Biological Engineering and Computing, 2008, vol. 46 (11), pp. 1139-1152.

Pennati G., et al., "Computational Fluid Dynamics Models and Congenital Heart Diseases," Frontiers in Pediatrics, 2013, vol. 1, 4 pages.

Qian Y., et al., "Computational Hemodynamic Analysis in Congenital Heart Disease: Simulation of the Norwood Procedure," Annals of Biomedical Engineering, 2010, vol. 38 (7), pp. 2302-2313.

Rieber J., et al., "Cardiac Magnetic Resonance Perfusion Imaging for the Functional Assessment of Coronary Artery Disease: A Comparison with Coronary Angiography and Fractional Flow Reserve," European Heart Journal, 2006, vol. 27 (12), pp. 1465-1471.

Sud V.K., et al., "Simulation of Steady Cardiovascular Flow in the Presence of Stenosis using a Finite Element Method," Physics in Medicine and Biology, 1990, vol. 35 (7), pp. 947-959.

Suttorp M.J., et al., "Primary Stenting of Totally Occluded Native Coronary Arteries II (PRISON II): a Randomized Comparison of Bare Metal Stent Implantation with Sirolimus-Eluting Stent Implantation for the Treatment of Total Coronary Occlusions," Circulation, 2006, vol. 114 (9), pp. 921-928.

Zhang J.M., et al., "Perspective on CFD Studies of Coronary Artery Disease Lesions and Hemodynamics: A Review," International Journal for Numerical Methods in Biomedical Engineering, 2014.

Antiga L., et al., "An Image-Based Modeling Framework for Patient-Specific Computational Hemodynamics," Medical & Biological Engineering & Computing, Nov. 2008, vol. 46 (11), pp. 1097-1112.

European Search Report for Application No. EP17155303, dated May 24, 2017, 7 pages.

Kock S.A., et al., "Mechanical Stresses in Carotid Plaques using MRI-Based Fluid-Structure Interaction Models," Journal of Biomechanics, 2008, vol. 41 (8), pp. 1651-1658.

Migliavacca F., et al., "Multiscale Modelling in Biofluidynamics: Application to Reconstructive Paediatric Cardiac Surgery," Journal of Biomechanics, 2006, vol. 39 (6), pp. 1010-1020.

\* cited by examiner

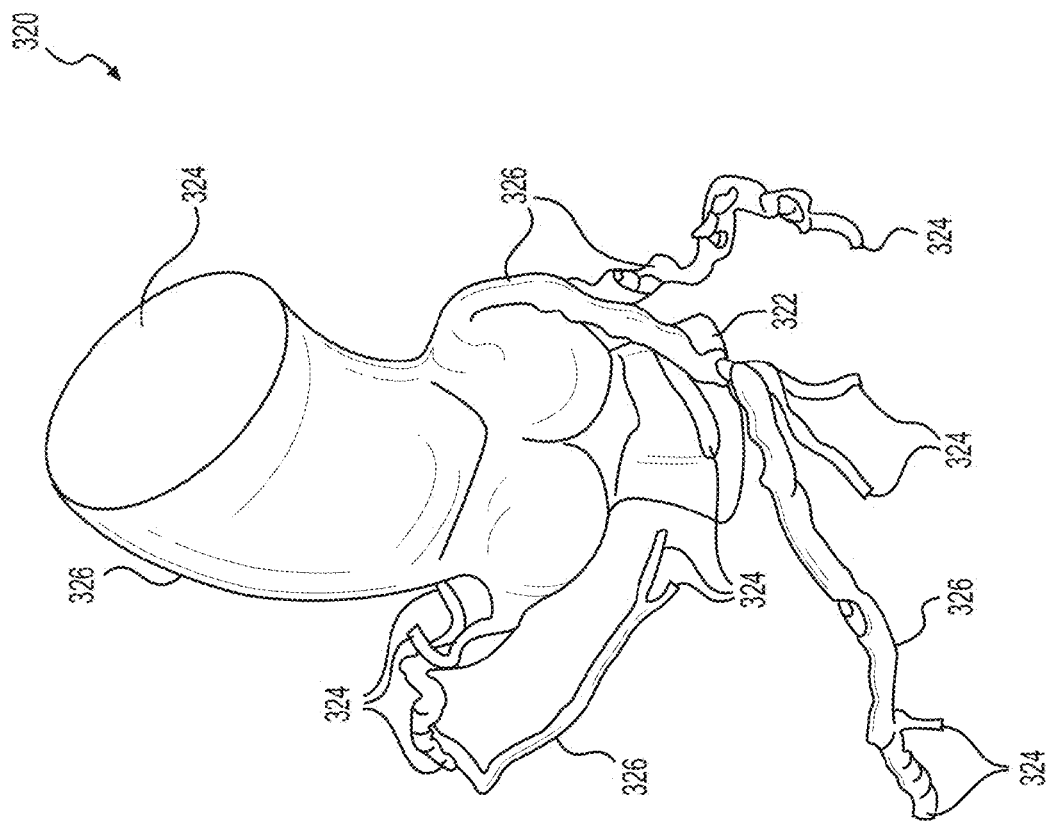

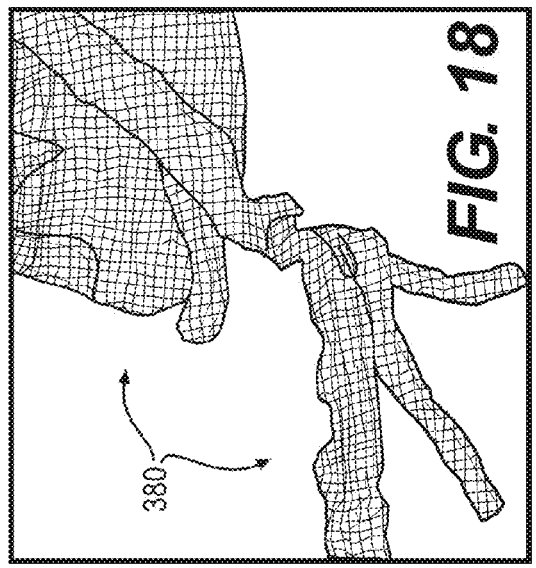
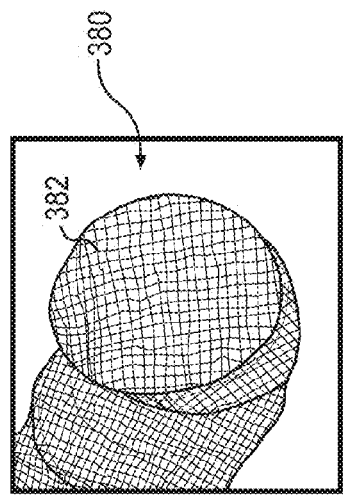
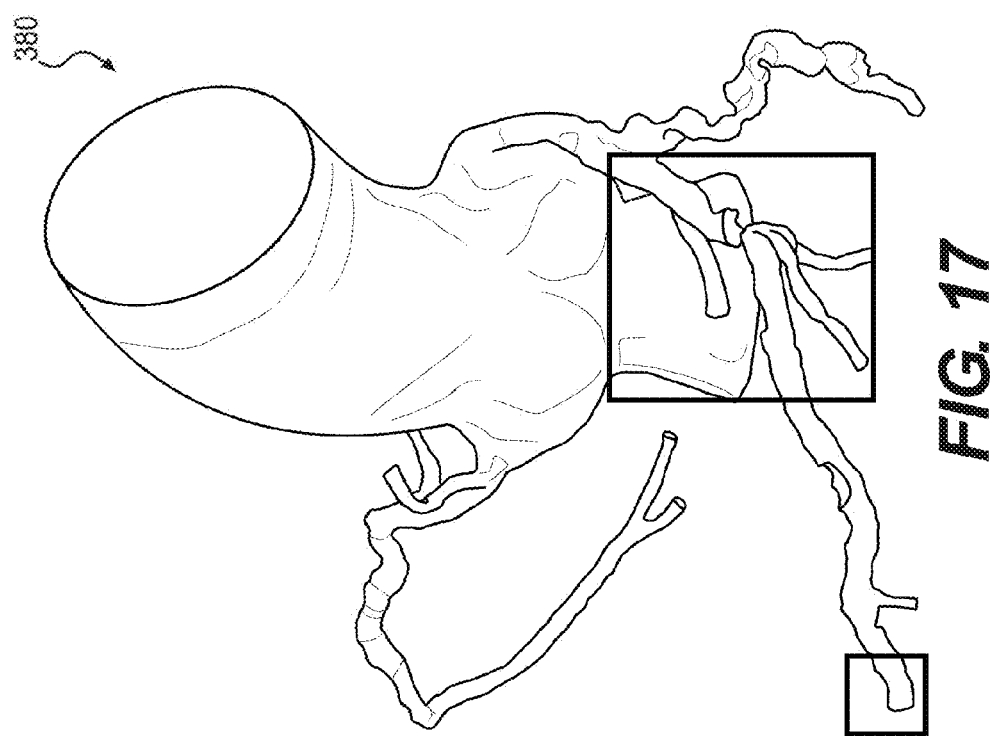

METHOD AND SYSTEM FOR IMAGE PROCESSING AND PATIENT-SPECIFIC MODELING OF BLOOD FLOW

PRIORITY

This application is a continuation of U.S. patent application Ser. No. 14/866,098, filed Sep. 25, 2015, which is a continuation of U.S. patent application Ser. No. 14/276,442, filed May 13, 2014 (now U.S. Pat. No. 9,226,672), which is a continuation of U.S. patent application Ser. No. 13/658,739, filed Oct. 23, 2012, which is a continuation of U.S. patent application Ser. No. 13/014,835, filed Jan. 27, 2011 (now U.S. Pat. No. 8,311,747), which is a divisional of U.S. patent application Ser. No. 13/013,561, filed Jan. 25, 2011 (now U.S. Pat. 8,315,812), which claims the benefit of priority from U.S. Provisional Application No. 61/401,462, filed Aug. 12, 2010, U.S. Provisional Application No. 61/401,915, filed Aug. 20, 2010, U.S. Provisional Application No. 61/402,308, filed Aug. 26, 2010, U.S. Provisional Application No. 61/402,345, filed Aug. 27, 2010, and U.S. Provisional Application No. 61/404,429, filed Oct. 1, 2010, which are herein incorporated by reference in their entirety.

TECHNICAL FIELD

Embodiments include methods and systems for modeling of fluid flow and more particularly methods and systems for patient-specific modeling of blood flow.

BACKGROUND

Coronary artery disease may produce coronary lesions in the blood vessels providing blood to the heart, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it cannot be used to predict changes in coronary blood flow, pressure, or myocardial perfusion under other physiologic states, e.g., exercise, nor can it be used to predict outcomes of interventions.

Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to what has been referred to as an "oculostenotic reflex" of some interventional cardiologists to insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., induced by intravenous administration of adenosine. The blood pressures may be measured by inserting a pressure wire into the patient. Thus, the decision to treat a lesion based on the determined FFR may be made after the initial cost and risk of diagnostic cardiac catheterization has already been incurred.

Thus, a need exists for a method for assessing coronary anatomy, myocardial perfusion, and coronary artery flow noninvasively. Such a method and system may benefit cardiologists who diagnose and plan treatments for patients with suspected coronary artery disease. In addition, a need exists for a method to predict coronary artery flow and myocardial perfusion under conditions that cannot be directly measured, e.g., exercise, and to predict outcomes of medical, interventional, and surgical treatments on coronary artery blood flow and myocardial perfusion.

It is to be understood that both the foregoing general description and the following detailed description are exemplary and explanatory only and are not restrictive of the disclosure.

SUMMARY

In accordance with an embodiment, a system for determining cardiovascular information for a patient includes at least one computer system configured to receive patient-specific data regarding a geometry of the patient's heart and create a three-dimensional model representing at least a portion of the patient's heart based on the patient-specific data. The at least one computer system is further configured to create a physics-based model relating to a blood flow characteristic of the patient's heart and determine a fractional flow reserve within the patient's heart based on the three-dimensional model and the physics-based model.

In accordance with another embodiment, a method for determining patient-specific cardiovascular information using at least one computer system includes inputting into the at least one computer system patient-specific data regarding a geometry of the patient's heart, and creating, using the at least one computer system, a three-dimensional model representing at least a portion of the patient's heart based on the patient-specific data. The method further includes creating, using the at least one computer system, a physics-based model relating to a blood flow characteristic of the patient's heart, and determining, using the at least one computer system, a fractional flow reserve within the patient's heart based on the three-dimensional model and the physics-based model.

In accordance with another embodiment, a non-transitory computer readable medium for use on at least one computer system containing computer-executable programming instructions for performing a method for determining patient-specific cardiovascular information is provided. The method includes receiving patient-specific data regarding a geometry of the patient's heart and creating a three-dimensional model representing at least a portion of the patient's heart based on the patient-specific data. The method further includes creating a physics-based model relating to a blood flow characteristic in the patient's heart and determining a fractional flow reserve within the patient's heart based on the three-dimensional model and the physics-based model.

In accordance with another embodiment, a system for planning treatment for a patient includes at least one computer system configured to receive patient-specific data regarding a geometry of an anatomical structure of the patient and create a three-dimensional model representing at least a portion of the anatomical structure of the patient based on the patient-specific data. The at least one computer system is further configured to determine first information regarding a blood flow characteristic within the anatomical structure of the patient based on the three-dimensional model and a physics-based model relating to the anatomical structure of the patient, modify the three-dimensional model, and determine second information regarding the blood flow characteristic within the anatomical structure of the patient based on the modified three-dimensional model.

In accordance with another embodiment, a non-transitory computer readable medium for use on a computer system containing computer-executable programming instructions for performing a method for planning treatment for a patient is provided. The method includes receiving patient-specific data regarding a geometry of an anatomical structure of the patient and creating a three-dimensional model representing at least a portion of the anatomical structure of the patient based on the patient-specific data. The method further includes determining first information regarding a blood flow characteristic within the anatomical structure of the patient based on the three-dimensional model and a physics-based model relating to the anatomical structure of the patient, and determining second information regarding the blood flow characteristic within the anatomical structure of the patient based on a desired change in geometry of the anatomical structure of the patient.

In accordance with another embodiment, a method for planning treatment for a patient using a computer system includes inputting into at least one computer system patient-specific data regarding a geometry of an anatomical structure of the patient and creating, using the at least one computer system, a three-dimensional model representing at least a portion of the anatomical structure of the patient based on the patient-specific data. The method further includes determining, using the at least one computer system, first information regarding a blood flow characteristic within the anatomical structure of the patient based on the three-dimensional model and a physics-based model relating to the anatomical structure of the patient. The method also includes modifying, using the at least one computer system, the three-dimensional model, and determining, using the at least one computer system, second information regarding the blood flow characteristic within the anatomical structure of the patient based on the modified three-dimensional model.

In accordance with another embodiment, a system for planning treatment for a patient includes at least one computer system configured to receive patient-specific data regarding a geometry of an anatomical structure of the patient and create a three-dimensional model representing at least a portion of the anatomical structure of the patient based on the patient-specific data. The at least one computer system is also configured to determine first information regarding a blood flow characteristic within the anatomical structure of the patient based on the three-dimensional model and information regarding a physiological condition of the patient, modify the physiological condition of the patient, and determine second information regarding the blood flow characteristic within the anatomical structure of the patient based on the modified physiological condition of the patient.

In accordance with another embodiment, a non-transitory computer readable medium for use on a computer system containing computer-executable programming instructions for performing a method for planning treatment for a patient is provided. The method includes receiving patient-specific data regarding a geometry of an anatomical structure of the patient and creating a three-dimensional model representing at least a portion of the anatomical structure of the patient based on the patient-specific data. The method further includes determining first information regarding a blood flow characteristic within the anatomical structure of the patient based on the three-dimensional model and information regarding a physiological condition of the patient, and determining second information regarding the blood flow characteristic within the anatomical structure of the patient based on a desired change in the physiological condition of the patient.

In accordance with another embodiment, a method for planning treatment for a patient using at least one computer system includes inputting into at least one computer system patient-specific data regarding a geometry of an anatomical structure of the patient, and creating, using the at least one computer system, a three-dimensional model representing at least a portion of the anatomical structure of the patient based on the patient-specific data. The method also includes determining, using the at least one computer system, first information regarding a blood flow characteristic within the anatomical structure of the patient based on the three-dimensional model and information regarding a physiological condition of the patient. The method further includes modifying, using the at least one computer system, the physiological condition of the patient, and determining, using the at least one computer system, second information regarding the blood flow characteristic within the anatomical structure of the patient based on the modified physiological condition of the patient.

In accordance with another embodiment, a system for determining patient-specific cardiovascular information includes at least one computer system configured to receive patient-specific data regarding a geometry of an anatomical structure of the patient and create a three-dimensional model representing at least a portion of the anatomical structure of the patient based on the patient-specific data. The at least one computer system is also configured to determine a total resistance associated with a total flow through the portion of the anatomical structure of the patient and determine information regarding a blood flow characteristic within the anatomical structure of the patient based on the three-dimensional model, a physics-based model relating to the anatomical structure of the patient, and the determined total resistance.

In accordance with another embodiment, a method for determining patient-specific cardiovascular information using at least one computer system includes inputting into the at least one computer system patient-specific data regarding a geometry of an anatomical structure of the patient, and creating, using at least one computer, a three-dimensional model representing at least a portion of the anatomical structure of the patient based on the patient-specific data. The method also includes determining, using at least one computer, a total resistance associated with a total flow through the portion of the anatomical structure of the patient, and determining, using at least one computer, information regarding a blood flow characteristic within the anatomical structure of the patient based on the three-dimensional model, a physics-based model relating to the anatomical structure of the patient, and the determined total resistance.

In accordance with another embodiment, a non-transitory computer readable medium for use on a computer system containing computer-executable programming instructions for performing a method for determining patient-specific cardiovascular information is provided. The method includes receiving patient-specific data regarding a geometry of an anatomical structure of the patient and creating a three-dimensional model representing at least a portion of the anatomical structure of the patient based on the patient-specific data. The method also includes determining a total resistance associated with a total flow through the portion of the anatomical structure of the patient and determining information regarding a blood flow characteristic within the anatomical structure of the patient based on the three-dimensional model, a physics-based model relating to the anatomical structure of the patient, and the determined total resistance.

In accordance with another embodiment, a system for providing patient-specific cardiovascular information using a web site includes at least one computer system configured to allow a remote user to access a web site, receive patient-specific data regarding at least a portion of a geometry of an anatomical structure of the patient, create a three-dimensional model representing at least a portion of the anatomical structure of the patient based on the patient-specific data, and determine information regarding a blood flow characteristic within the anatomical structure of the patient based on the three-dimensional model and a physiological condition of the patient. The at least one computer system is also configured to communicate display information regarding a first three-dimensional simulation of at least the portion of the anatomical structure of the patient to the remote user using the web site. The three-dimensional simulation includes the determined information regarding the blood flow characteristic.

In accordance with another embodiment, a method for providing patient-specific cardiovascular information using a web site includes allowing, using at least one computer system, a remote user to access a web site, and receiving, using the at least one computer system, patient-specific data regarding a geometry of an anatomical structure of the patient. The method also includes creating, using the at least one computer system, a three-dimensional model representing at least a portion of the anatomical structure of the patient based on the patient-specific data, and determining, using the at least one computer system, information regarding a blood flow characteristic within the anatomical structure of the patient based on the three-dimensional model and a physiological condition of the patient. The method further includes communicating, using the at least one computer system, display information regarding a first three-dimensional simulation of at least the portion of the anatomical structure of the patient to the remote user using the web site. The three-dimensional simulation includes the determined information regarding the blood flow characteristic.

In accordance with another embodiment, a non-transitory computer readable medium for use on a computer system containing computer-executable programming instructions for performing a method for providing patient-specific cardiovascular information using a web site is provided. The method includes allowing a remote user to access a web site, receiving patient-specific data regarding a geometry of an anatomical structure of the patient, and creating a three-dimensional model representing at least a portion of the anatomical structure of the patient based on the patient-specific data. The method also includes determining information regarding a blood flow characteristic within the anatomical structure of the patient based on the three-dimensional model and a physics-based model relating to the anatomical structure of the patient, and communicating display information regarding a first three-dimensional simulation of at least the portion of the anatomical structure of the patient to the remote user using the web site. The three-dimensional simulation includes the determined information regarding the blood flow characteristic.

In accordance with another embodiment, a system for determining patient-specific time-varying cardiovascular information includes at least one computer system configured to receive time-varying patient-specific data regarding a geometry of at least a portion of an anatomical structure of the patient at different times and create a three-dimensional model representing at least a portion of the anatomical structure of the patient based on the patient-specific data. The at least one computer system is also configured to determine information regarding a change in a blood flow characteristic over time within the anatomical structure of the patient based on the three-dimensional model and a physics-based model relating to the anatomical structure of the patient.

In accordance with another embodiment, a method for determining patient-specific time-varying cardiovascular information using at least one computer system includes receiving, using at least one computer system, time-varying patient-specific data regarding a geometry of an anatomical structure of the patient at different times. The method also includes creating, using the at least one computer system, a three-dimensional model representing at least a portion of the anatomical structure of the patient based on the patient-specific data. The method further includes determining, using the at least one computer system, information regarding a change in a blood flow characteristic over time within the anatomical structure of the patient based on the three-dimensional model and the information regarding a physics-based model relating to the anatomical structure of the patient.

In accordance with another embodiment, a non-transitory computer readable medium for use on a computer system containing computer-executable programming instructions for performing a method for determining patient-specific time-varying cardiovascular information is provided. The method includes receiving time-varying patient-specific data regarding a geometry of an anatomical structure of the patient at different times, creating a three-dimensional model representing at least a portion of the anatomical structure of the patient based on the patient-specific data, and determining information regarding a change in a blood flow characteristic over time within the anatomical structure of the patient based on the three-dimensional model and the information regarding a physics-based model relating to the anatomical structure of the patient.

In accordance with another embodiment, a system for determining cardiovascular information for a patient includes at least one computer system configured to receive patient-specific data regarding a geometry and at least one material property of at least a portion of an anatomical structure of the patient. The anatomical structure includes at least a portion of a blood vessel. The at least one computer system is further configured to create a three-dimensional model representing the anatomical structure of the patient based on the patient-specific data, and determine information regarding a blood flow characteristic within the anatomical structure of the patient based on the three-dimensional model and a physiological condition of the patient. The at least one computer system is also configured to identify a location of a plaque within the blood vessel.

In accordance with another embodiment, a method for determining cardiovascular information for a patient using at least one computer system includes receiving, using at least one computer system, patient-specific data regarding a geometry and at least one material property of at least a portion of an anatomical structure of the patient. The anatomical structure includes at least a portion of a blood vessel. The method also includes creating, using the at least one computer system, a three-dimensional model representing the anatomical structure of the patient based on the patient-specific data, and determining, using the at least one computer system, information regarding a blood flow characteristic within the anatomical structure of the patient based on the three-dimensional model and a physiological condition of the patient. The method further includes identifying, using the at least one computer system, a plaque within the blood vessel.

In accordance with another embodiment, a non-transitory computer readable medium for use on a computer system containing computer-executable programming instructions for performing a method for determining cardiovascular information for a patient is provided. The method includes receiving patient-specific data regarding a geometry and at least one material property of at least a portion of an anatomical structure of the patient. The anatomical structure includes at least a portion of a blood vessel. The method also includes creating a three-dimensional model representing the anatomical structure of the patient based on the patient-specific data, determining information regarding a blood flow characteristic within the anatomical structure of the patient based on the three-dimensional model and a physiological condition of the patient, and identifying a location of a plaque within the blood vessel.

In accordance with another embodiment, a system for determining cardiovascular information for a patient includes at least one computer system configured to receive patient-specific data regarding a geometry of at least a portion of an anatomical structure of the patient. The anatomical structure includes at least a portion of a plurality of arteries and tissue connected to at least a portion of the plurality of arteries. The at least one computer system is further configured to create a three-dimensional model representing the anatomical structure of the patient based on the patient-specific data, divide at least a portion of the three-dimensional model representing the tissue into segments, and determine information regarding a blood flow characteristic associated with at least one of the segments based on the three-dimensional model and a physiological condition of the patient.

In accordance with another embodiment, a method for determining cardiovascular information for a patient using at least one computer system includes receiving, using at least one computer system, patient-specific data regarding a geometry of at least a portion of an anatomical structure of the patient. The anatomical structure includes at least a portion of a plurality of arteries and tissue connected to at least a portion of the plurality of arteries. The method also includes creating, using the at least one computer system, a three-dimensional model representing the anatomical structure of the patient based on the patient-specific data, and extending, using the at least one computer system, the three-dimensional model to form an augmented model. The method further includes dividing, using the at least one computer system, at least a portion of the augmented model representing the tissue into segments, and determining, using the at least one computer system, information regarding a blood flow characteristic associated with at least one of the segments based on the augmented model and a physiological condition of the patient.

In accordance with another embodiment, a non-transitory computer readable medium for use on a computer system containing computer-executable programming instructions for performing a method for determining cardiovascular information for a patient is provided. The method includes receiving patient-specific data regarding a geometry of at least a portion of an anatomical structure of the patient. The anatomical structure includes at least a portion of a plurality of arteries and tissue connected to at least a portion of the plurality of arteries. The method also includes creating a three-dimensional model representing the anatomical structure of the patient based on the patient-specific data, dividing at least a portion of the three-dimensional model representing the tissue into segments, and determining information regarding a blood flow characteristic associated with at least one of the segments based on the three-dimensional model and a physics-based model relating to the anatomical structure.

In accordance with another embodiment, a system for determining cardiovascular information for a patient includes at least one computer system configured to receive patient-specific data regarding a geometry of the patient's brain. The at least one computer system is further configured to create a three-dimensional model representing at least a portion of the patient's brain based on the patient-specific data, and determine information regarding a blood flow characteristic within the patient's brain based on the three-dimensional model and a physics-based model relating to the patient's brain.

In accordance with another embodiment, a method for determining patient-specific cardiovascular information using at least one computer system includes inputting into the at least one computer system patient-specific data regarding a geometry of at least a portion of a plurality of cerebral arteries of the patient. The method also includes creating, using the at least one computer system, a three-dimensional model representing at least the portion of the cerebral arteries of the patient based on the patient-specific data, and determining, using the at least one computer system, information regarding a blood flow characteristic within the cerebral arteries of the patient based on the three-dimensional model and a physics-based model relating to the cerebral arteries of the patient.

In accordance with another embodiment, a non-transitory computer readable medium for use on at least one computer system containing computer-executable programming instructions for performing a method for determining patient-specific cardiovascular information is provided. The method includes receiving patient-specific data regarding a geometry of the patient's brain, creating a three-dimensional model representing at least a portion of the patient's brain based on the patient-specific data, and determining information regarding a blood flow characteristic within the patient's brain based on the three-dimensional model and a physics-based model relating to the patient's brain.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

FIG. 8 shows a trimmed solid model, according to an exemplary embodiment;

FIG. 17 shows a three-dimensional mesh prepared based on the solid model of FIG. 8;

FIGS. 18 and 19 show portions of the three-dimensional mesh of FIG. 17;

DESCRIPTION OF THE EMBODIMENTS

Figure 1:
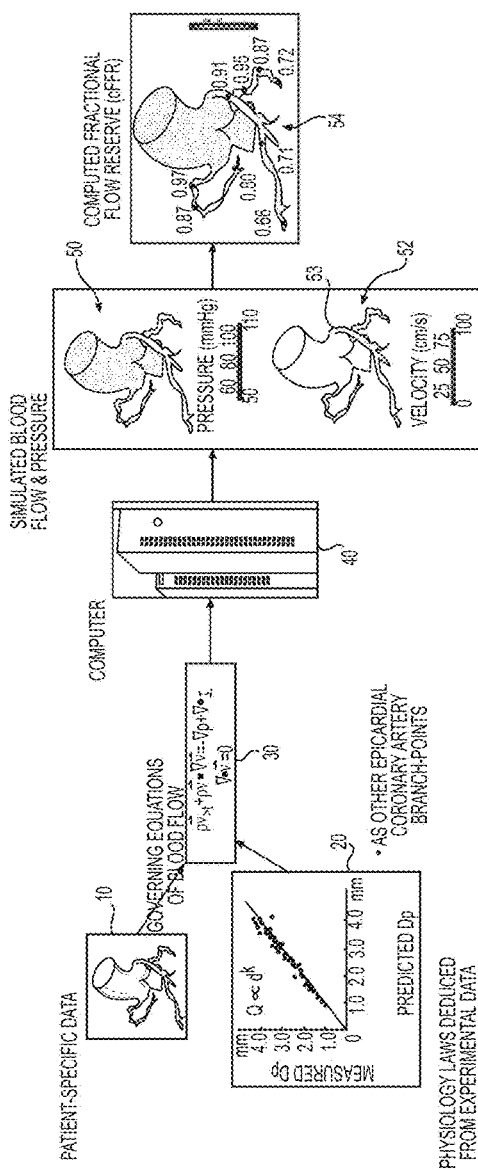
FIG. 1 is a schematic diagram of a system for providing various information relating to coronary blood flow in a specific patient, according to an exemplary embodiment.

Reference will now be made in detail to exemplary embodiments, examples of which are illustrated in the accompanying drawings. Wherever possible, the same reference numbers will be used throughout the drawings to refer to the same or like parts. This description is organized according to the following outline:

I. Overview
II. Obtaining and Preprocessing Patient-Specific Anatomical Data
III. Creating the Three-Dimensional Model Based on Obtained Anatomical Data
IV. Preparing The Model For Analysis and Determining Boundary Conditions
   A. Preparing the Model For Analysis
   B. Determining Boundary Conditions
      i. Determining Reduced Order Models
      ii. Exemplary Lumped Parameter Models
   C. Creating the Three-Dimensional Mesh
V. Performing The Computational Analysis And Outputting Results
   A. Performing the Computational Analysis
   B. Displaying Results for Blood Pressure, Flow, and cFFR
   C. Verifying Results
   D. Another Embodiment of a System and Method for Providing Coronary Blood Flow Information
VI. Providing Patient-Specific Treatment Planning
   A. Using Reduced Order Models to Compare Different Treatment Options
VII. Other Results
   A. Assessing Myocardial Perfusion
   B. Assessing Plaque Vulnerability
VIII. Other Applications
   A. Modeling Intracranial and Extracranial Blood Flow
      i. Assessing Cerebral Perfusion
      ii. Assessing Plaque Vulnerability I. Overview In an exemplary embodiment, a method and system determines various information relating to blood flow in a specific patient using information retrieved from the patient noninvasively. The determined information may relate to blood flow in the patient's coronary vasculature. Alternatively, as will be described below in further detail, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. The coronary vasculature circulates blood to and within the heart and includes an aorta 2 (FIG. 5) that supplies blood to a plurality of main coronary arteries 4 (FIG. 5) (e.g., the left anterior descending (LAD) artery, the left circumflex (LCX) artery, the right coronary (RCA) artery, etc.), which may further divide into branches of arteries or other types of vessels downstream from the aorta 2 and the main coronary arteries 4. Thus, the exemplary method and system may determine various information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

FIG. 1 shows aspects of a system for providing various information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54.

Figure 2:
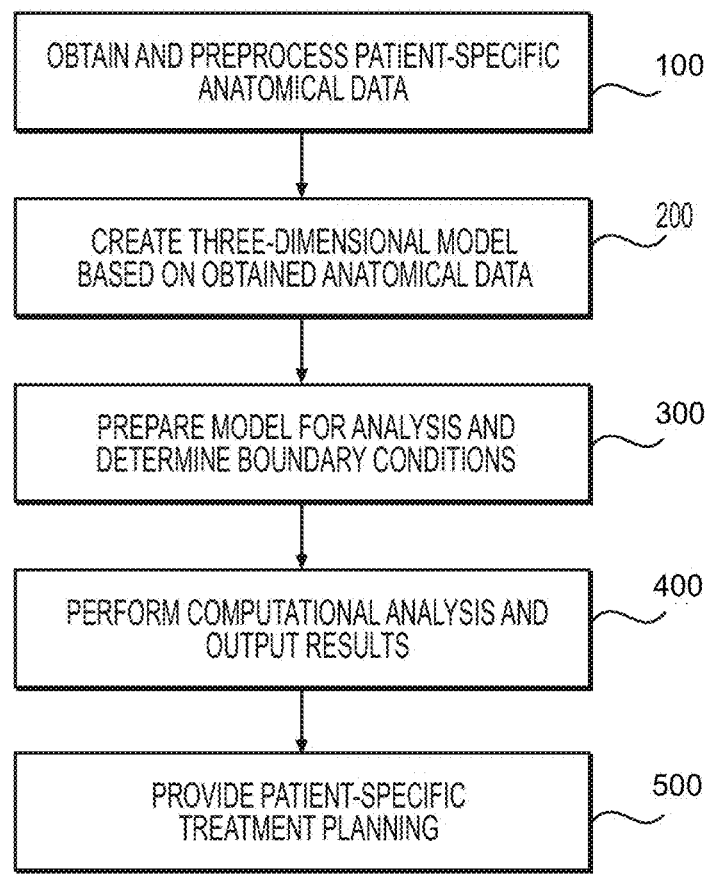
FIG. 2 is a flow chart of a method for providing various information relating to blood flow in a specific patient, according to an exemplary embodiment.

FIG. 2 shows aspects of a method for providing various information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 100). The patient-specific anatomical data may be obtained noninvasively, e.g., by CCTA, as will be described below.

A three-dimensional model of the patient's anatomy may be created based on the obtained anatomical data (step 200). For example, the three-dimensional model may be the three-dimensional model 10 of the patient's anatomy described above in connection with FIG. 1.

The three-dimensional model may be prepared for analysis and boundary conditions may be determined (step 300). For example, the three-dimensional model 10 of the patient's anatomy described above in connection with FIG. 1 may be trimmed and discretized into a volumetric mesh, e.g., a finite element or finite volume mesh. The volumetric mesh may be used to generate the equations 30 described above in connection with FIG. 1.

Boundary conditions may also be assigned and incorporated into the equations 30 described above in connection with FIG. 1. The boundary conditions provide information about the three-dimensional model 10 at its boundaries, e.g., the inflow boundaries 322 (FIG. 8), the outflow boundaries 324 (FIG. 8), the vessel wall boundaries 326 (FIG. 8), etc. The inflow boundaries 322 may include the boundaries through which flow is directed into the anatomy of the three-dimensional model, such as at an end of the aorta near the aortic root (e.g., end A shown in FIG. 16). Each inflow boundary 322 may be assigned, e.g., with a prescribed value or field for velocity, flow rate, pressure, or other characteristic, by coupling a heart model and/or a lumped parameter model to the boundary, etc. The outflow boundaries 324 may include the boundaries through which flow is directed outward from the anatomy of the three-dimensional model, such as at an end of the aorta near the aortic arch (e.g., end B shown in FIG. 16), and the downstream ends of the main coronary arteries and the branches that extend therefrom (e.g., ends a-m shown in FIG. 16). Each outflow boundary can be assigned, e.g., by coupling a lumped parameter or distributed (e.g., a one-dimensional wave propagation) model, as will be described in detail below. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 400) to determine blood flow information for the patient. For example, the computational analysis may be performed with the equations 30 and using the computer 40 described above in connection with FIG. 1 to produce the images described above in connection with FIG. 1, such as the simulated blood pressure model 50, the simulated blood flow model 52, and/or the cFFR model 54.

The method may also include providing patient-specific treatment options using the results (step 500). For example, the three-dimensional model 10 created in step 200 and/or the boundary conditions assigned in step 300 may be adjusted to model one or more treatments, e.g., placing a coronary stent in one of the coronary arteries represented in the three-dimensional model 10 or other treatment options. Then, the computational analysis may be performed as described above in step 400 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow. The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Thus, the software tool may perform steps 100-500. In step 500, the physician may provide further inputs to the computer system to select possible treatment options, and the computer system may display to the physician new simulations based on the selected possible treatment options. Further, each of steps 100-500 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 100-500 and any other steps described below for providing patient-specific information. In step 500, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

It is to be understood that one or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Figure 3:
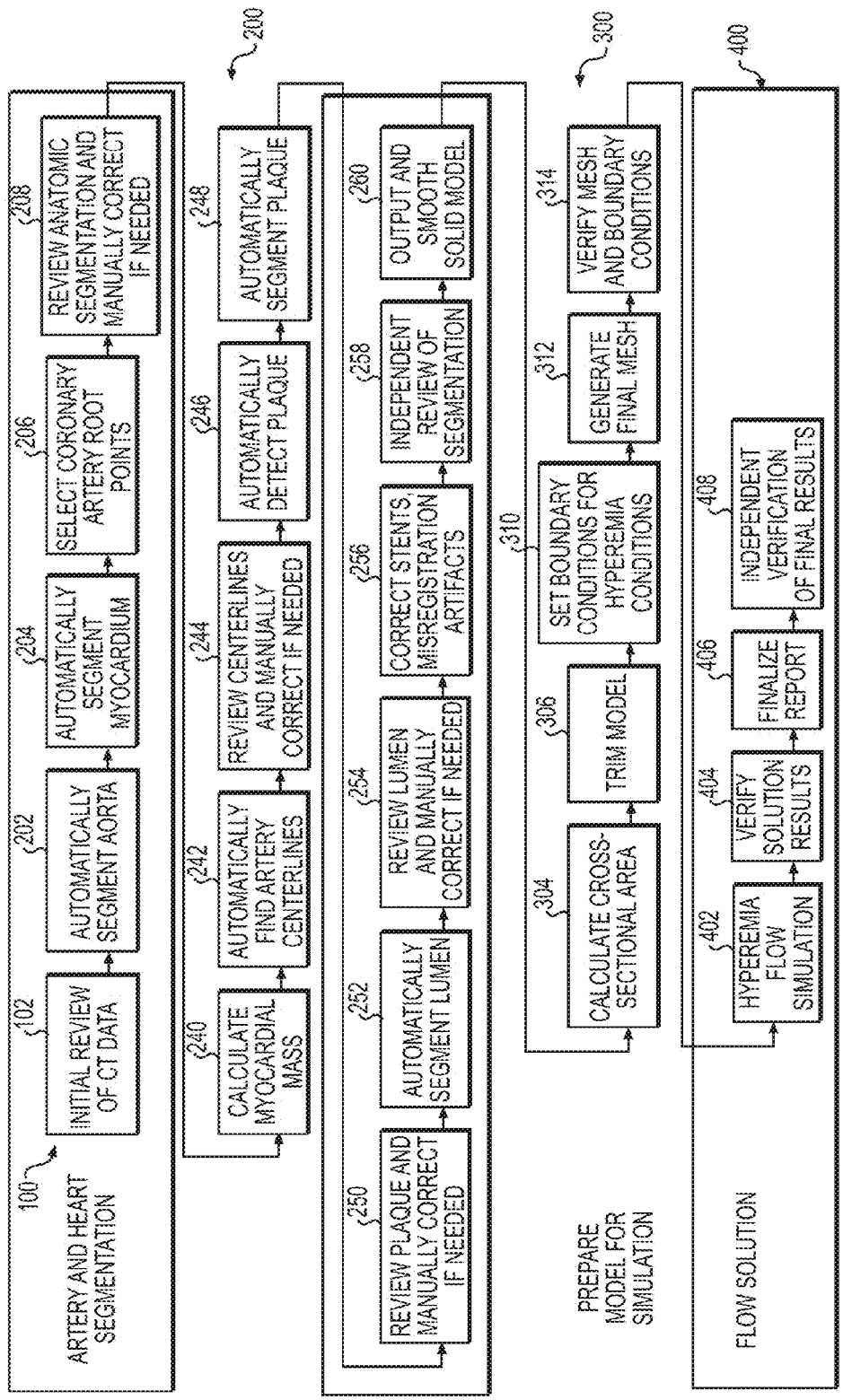
FIG. 3 is a flow chart showing the substeps of the method of FIG. 2.

FIG. 3 shows further aspects of the exemplary method for providing various information relating to blood flow in a specific patient. The aspects shown in FIG. 3 may be incorporated into the software tool that may be incorporated at least partially into a computer system and/or as part of a web-based service.

II. Obtaining and Preprocessing Patient-Specific Anatomical Data

As described above in connection with step 100 shown in FIG. 2, the exemplary method may include obtaining patient-specific anatomical data, such as information regarding the patient's heart, and preprocessing the data. In an exemplary embodiment, step 100 may include the following steps.

Initially, a patient may be selected. For example, the patient may be selected by the physician when the physician determines that information about the patient's coronary blood flow is desired, e.g., if the patient is experiencing symptoms associated with coronary artery disease, such as chest pain, heart attack, etc.

Figure 4:
FIG. 4 shows imaging data obtained noninvasively from a patient, according to an exemplary embodiment.

Patient-specific anatomical data may be obtained, such as data regarding the geometry of the patient's heart, e.g., at least a portion of the patient's aorta, a proximal portion of the main coronary arteries (and the branches extending therefrom) connected to the aorta, and the myocardium. The patient-specific anatomical data may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart. For example, 64-slice CCTA data may be obtained, e.g., data relating to 64 slices of the patient's heart, and assembled into a three-dimensional image. FIG. 4 shows an example of a three-dimensional image 120 produced by the 64-slice CCTA data.

Alternatively, other noninvasive imaging methods, such as magnetic resonance imaging (MRI) or ultrasound (US), or invasive imaging methods, such as digital subtraction angiography (DSA), may be used to produce images of the structures of the patient's anatomy. The imaging methods may involve injecting the patient intravenously with a contrast agent to enable identification of the structures of the anatomy. The resulting imaging data (e.g., provided by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may be the blood pressure in the patient's brachial artery (e.g., using a pressure cuff), such as the maximum (systolic) and minimum (diastolic) pressures.

The patient-specific anatomical data obtained as described above may be transferred over a secure communication line (e.g., via a network). For example, the data may be transferred to a server or other computer system for performing the computational analysis, e.g., the computational analysis described above in step 400. In an exemplary embodiment, the data may be transferred to a server or other computer system operated by a service provider providing a web-based service. Alternatively, the data may be transferred to a computer system operated by the patient's physician or other user.

Referring back to FIG. 3, the transferred data may be reviewed to determine if the data is acceptable (step 102). The determination may be performed by the user and/or by the computer system. For example, the transferred data (e.g., the CCTA data and other data) may be verified by a user and/or by the computer system, e.g., to determine if the CCTA data is complete (e.g., includes sufficient portions of the aorta and the main coronary arteries) and corresponds to the correct patient.

The transferred data (e.g., the CCTA data and other data) may also be preprocessed and assessed. The preprocessing and/or assessment may be performed by a user and/or by the computer system and may include, e.g., checking for misregistration, inconsistencies, or blurring in the CCTA data, checking for stents shown in the CCTA data, checking for other artifacts that may prevent the visibility of lumens of the blood vessels, checking for sufficient contrast between the structures (e.g., the aorta, the main coronary arteries, and other blood vessels) and the other portions of the patient, etc.

The transferred data may be evaluated to determine if the data is acceptable based on the verification, preprocessing, and/or assessment described above. During the verification, preprocessing, and/or assessment described above, the user and/or computer system may be able to correct certain errors or problems with the data. If, however, there are too many errors or problems, then the data may be determined to be unacceptable, and the user and/or computer system may generate a rejection report explaining the errors or problems necessitating the rejection of the transferred data. Optionally, a new CCTA scan may be performed and/or the physiological data described above may be measured from the patient again. If the transferred data is determined to be acceptable, then the method may proceed to step 202 described below.

Accordingly, step 102 shown in FIG. 3 and described above may be considered as a substep of step 100 of FIG. 2.

III. Creating The Three-Dimensional Model Based On Obtained Anatomical Data

As described above in connection with step 200 shown in FIG. 2, the exemplary method may include creating the three-dimensional model based on the obtained anatomical data. In an exemplary embodiment, step 200 may include the following steps.

Figure 5:
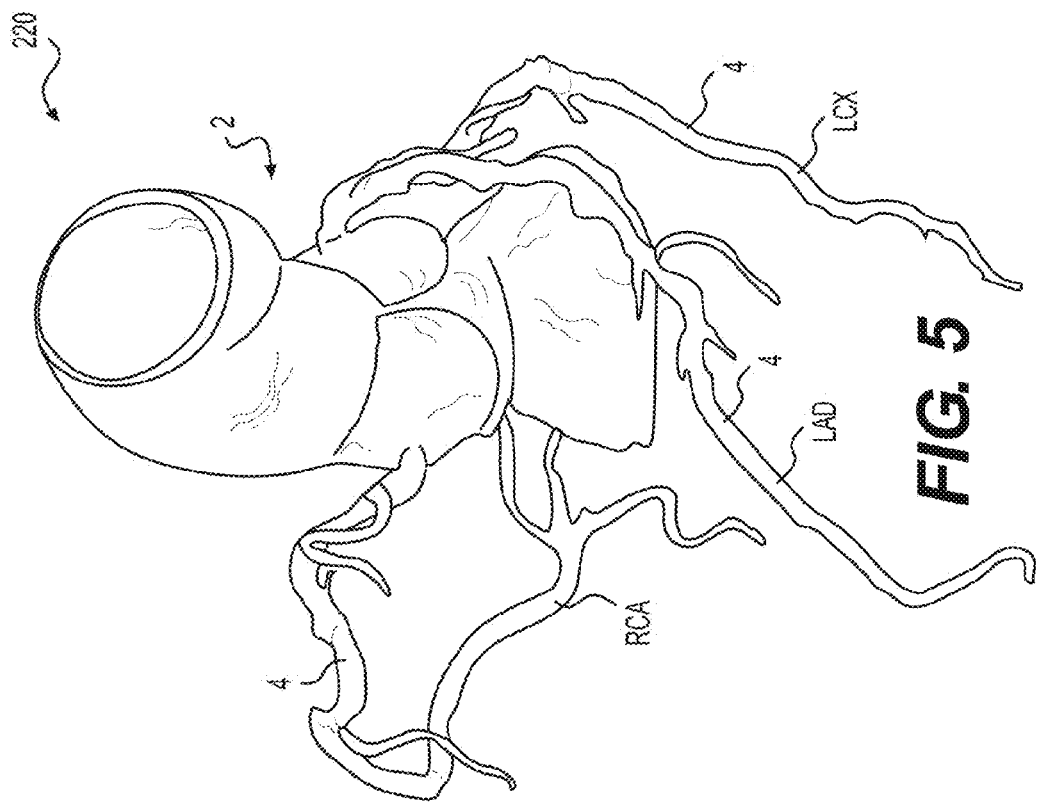
FIG. 5 shows an exemplary three-dimensional model generated using the imaging data of FIG. 4.

Using the CCTA data, a three-dimensional model of the coronary vessels may be generated. FIG. 5 shows an example of the surface of a three-dimensional model 220 generated using the CCTA data. For example, the model 220 may include, e.g., at least a portion of the aorta, at least a proximal portion of one or more main coronary arteries connected to that portion of the aorta, at least a proximal portion of one or more branches connected to the main coronary arteries, etc. The modeled portions of the aorta, the main coronary arteries, and/or the branches may be interconnected and treelike such that no portion is disconnected from the rest of the model 220. The process of forming the model 220 is called segmentation.

Referring back to FIG. 3, the computer system may automatically segment at least a portion of the aorta (step 202) and the myocardium (or other heart tissue, or other tissue connected to the arteries to be modeled) (step 204). The computer system may also segment at least a portion of the main coronary arteries connected to the aorta. In an exemplary embodiment, the computer system may allow the user to select one or more coronary artery root or starting points (step 206) in order to segment the main coronary arteries.

Segmentation may be performed using various methods. Segmentation may be performed automatically by the computer system based on user inputs or without user inputs. For example, in an exemplary embodiment, the user may provide inputs to the computer system in order to generate a first initial model. For example, the computer system may display to the user the three-dimensional image 120 (FIG. 4) or slices thereof produced from the CCTA data. The three-dimensional image 120 may include portions of varying intensity of lightness. For example, lighter areas may indicate the lumens of the aorta, the main coronary arteries, and/or the branches. Darker areas may indicate the myocardium and other tissue of the patient's heart.

Figure 6:
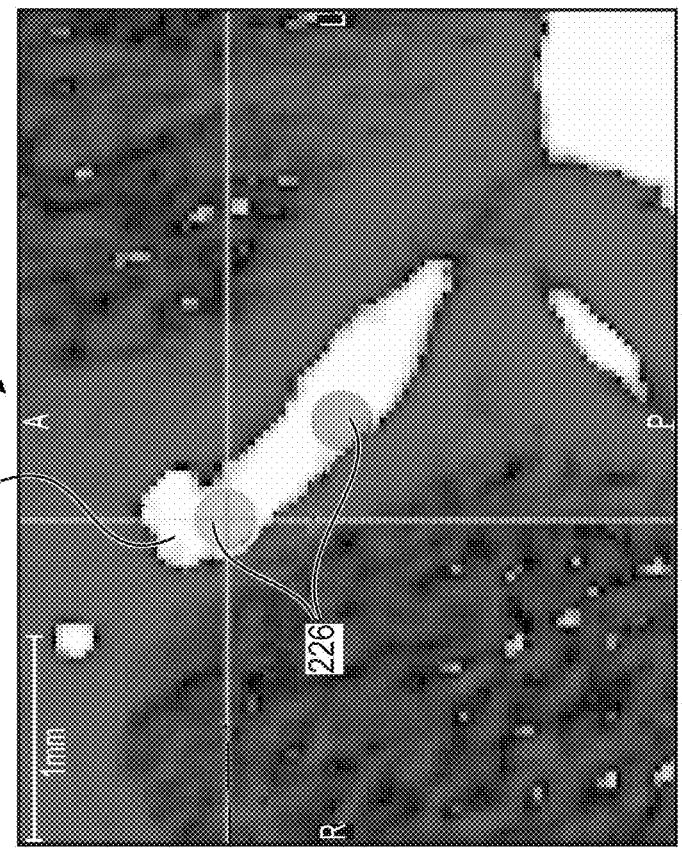
FIG. 6 shows a portion of a slice of the imaging data of FIG. 4 including seeds for forming a first initial model.

FIG. 6 shows a portion of a slice 222 of the three-dimensional image 120 that may be displayed to the user, and the slice 222 may include an area 224 of relative lightness. The computer system may allow the user to select the area 224 of relative lightness by adding one or more seeds 226, and the seeds 226 may serve as coronary artery root or starting points for segmenting the main coronary arteries. At the command of the user, the computer system may then use the seeds 226 as starting points to form the first initial model. The user may add seeds 226 in one or more of the aorta and/or the individual main coronary arteries. Optionally, the user may also add seeds 226 in one or more of the branches connected to the main coronary arteries. Alternatively, the computer system may place the seeds automatically, e.g., using extracted centerline information. The computer system may determine an intensity value of the image 120 where the seeds 226 have been placed and may form the first initial model by expanding the seeds 226 along the portions of the image 120 having the same intensity value (or within a range or threshold of intensity values centered at the selected intensity value). Thus, this method of segmentation may be called "threshold-based segmentation."

Figure 7:
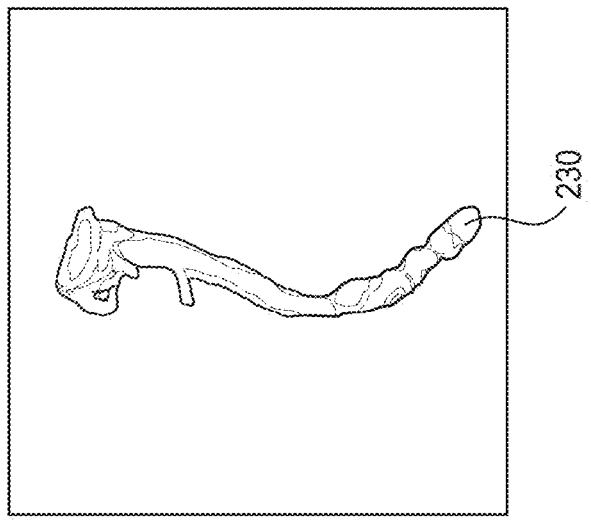
FIG. 7 shows a portion of the first initial model formed by expanding the seeds of FIG. 6.

FIG. 7 shows a portion 230 of the first initial model that is formed by expanding the seeds 226 of FIG. 6. Accordingly, the user inputs the seeds 226 as starting points for the computer system to begin forming the first initial model. This process may be repeated until the entire portions of interest, e.g., the portions of the aorta and/or the main coronary arteries, are segmented. Alternatively, the first initial model may be generated by the computer system without user inputs.

Alternatively, segmentation may be performed using a method called "edge-based segmentation." In an exemplary embodiment, both the threshold-based and edge-based segmentation methods may be performed, as will be described below, to form the model 220.

A second initial model may be formed using the edge-based segmentation method. With this method, the lumen edges of the aorta and/or the main coronary arteries may be located. For example, in an exemplary embodiment, the user may provide inputs to the computer system, e.g., the seeds 226 as described above, in order to generate the second initial model. The computer system may expand the seeds 226 along the portions of the image 120 until the edges are reached. The lumen edges may be located, e.g., by the user visually, and/or by the computer system (e.g., at locations where there is a change in intensity value above a set threshold). The edge-based segmentation method may be performed by the computer system and/or the user.

The myocardium or other tissue may also be segmented based on the CCTA data in step 204. For example, the CCTA data may be analyzed to determine the location of the internal and external surfaces of the myocardium, e.g., the left and/or right ventricles. The locations of the surfaces may be determined based on the contrast (e.g., relative darkness and lightness) of the myocardium compared to other structures of the heart in the CCTA data. Thus, the geometry of the myocardium may be determined.

The segmentation of the aorta, the myocardium, and/or the main coronary arteries may be reviewed and/or corrected, if necessary (step 208). The review and/or correction may be performed by the computer system and/or the user. For example, in an exemplary embodiment, the computer system may automatically review the segmentation, and the user may manually correct the segmentation if there are any errors, e.g., if any portions of the aorta, the myocardium, and/or the main coronary arteries in the model 220 are missing or inaccurate.

For example, the first and second initial models described above may be compared to ensure that the segmentation of the aorta and/or the main coronary arteries is accurate. Any areas of discrepancy between the first and second initial models may be compared to correct the segmentation and to form the model 220. For example, the model 220 may be an average between the first and second initial models. Alternatively, only one of the segmentation methods described above may be performed, and the initial model formed by that method may be used as the model 220.

The myocardial mass may be calculated (step 240). The calculation may be performed by the computer system. For example, the myocardial volume may be calculated based on the locations of the surfaces of the myocardium determined as described above, and the calculated myocardial volume may be multiplied by the density of the myocardium to calculate the myocardial mass. The density of the myocardium may be preset.

The centerlines of the various vessels (e.g., the aorta, the main coronary arteries, etc.) of the model 220 (FIG. 5) may be determined (step 242). In an exemplary embodiment, the determination may be performed automatically by the computer system.

The centerlines determined in step 242 may be reviewed and/or corrected, if necessary (step 244). The review and/or correction may be performed by the computer system and/or the user. For example, in an exemplary embodiment, the computer system may automatically review the centerlines, and the user may manually correct the centerlines if there are any errors, e.g., if any centerlines are missing or inaccurate.

Calcium or plaque (causing narrowing of a vessel) may be detected (step 246). In an exemplary embodiment, the computer system may automatically detect the plaque. For example, the plaque may be detected in the three-dimensional image 120 and removed from the model 220. The plaque may be identified in the three-dimensional image 120 since the plaque appears as areas that are even lighter than the lumens of the aorta, the main coronary arteries, and/or the branches. Thus, the plaque may be detected by the computer system as having an intensity value below a set value or may be detected visually by the user. After detecting the plaque, the computer system may remove the plaque from the model 220 so that the plaque is not considered as part of the lumen or open space in the vessels. Alternatively, the computer system may indicate the plaque on the model 220 using a different color, shading, or other visual indicator than the aorta, the main coronary arteries, and/or the branches.

The computer system may also automatically segment the detected plaque (step 248). For example, the plaque may be segmented based on the CCTA data. The CCTA data may be analyzed to locate the plaque (or a surface thereof) based on the contrast (e.g., relative darkness and lightness) of the plaque compared to other structures of the heart in the CCTA data. Thus, the geometry of the plaque may also be determined.

The segmentation of the plaque may be reviewed and/or corrected, if necessary (step 250). The review and/or correction may be performed by the computer system and/or the user. For example, in an exemplary embodiment, the computer system may automatically review the segmentation, and the user may manually correct the segmentation if there are any errors, e.g., if any plaque is missing or shown inaccurately.

The computer system may automatically segment the branches connected to the main coronary arteries (step 252). For example, the branches may be segmented using similar methods for segmenting the main coronary arteries, e.g., as shown in FIGS. 6 and 7 and described above in connection with step 206. The computer system may also automatically segment the plaque in the segmented branches using similar methods as described above in connection with steps 248 and 250. Alternatively, the branches (and any plaque contained therein) may be segmented at the same time as the main coronary arteries (e.g., in step 206).

The segmentation of the branches may be reviewed and/or corrected, if necessary (step 254). The review and/or correction may be performed by the computer system and/or the user. For example, in an exemplary embodiment, the computer system may automatically review the segmentation, and the user may manually correct the segmentation if there are any errors, e.g., if any portions of the branches in the model 220 are missing or inaccurate.

The model 220 may be corrected if any misregistration, stents, or other artifacts are located (e.g., during the review of the CCTA data in step 102) (step 256). The correction may be performed by a user and/or by the computer system. For example, if a misregistration or other artifact (e.g., inconsistency, blurring, an artifact affecting lumen visibility, etc.) is located, the model 220 may be reviewed and/or corrected to avoid an artificial or false change in the cross-sectional area of a vessel (e.g., an artificial narrowing). If a stent is located, the model 220 may be reviewed and/or corrected to indicate the location of the stent and/or to correct the cross-sectional area of the vessel where the stent is located, e.g., based on the size of the stent.

The segmentation of the model 220 may also be independently reviewed (step 258). The review may be performed by a user and/or by the computer system. For example, the user and/or computer system may be able to identify certain errors with the model 220, such as correctable errors and/or errors that may require the model 220 to be at least partially redone or resegmented. If such errors are identified, then the segmentation may be determined to be unacceptable, and certain steps, e.g., one or more of steps 202-208, 240-256, depending on the error(s), may be repeated.

If the segmentation of the model 220 is independently verified as acceptable, then, optionally, the model 220 may be output and smoothed (step 260). The smoothing may be performed by the user and/or by the computer system. For example, ridges, points, or other discontinuous portions may be smoothed. The model 220 may be output to a separate software module to be prepared for computational analysis, etc.

Accordingly, steps 202-208 and 240-260 shown in FIG. 3 and described above may be considered as substeps of step 200 of FIG. 2.

IV. Preparing the Model for Analysis and Determining Boundary Conditions

As described above in connection with step 300 shown in FIG. 2, the exemplary method may include preparing the model for analysis and determining boundary conditions. In an exemplary embodiment, step 300 may include the following steps.

A. Preparing the Model for Analysis

Referring back to FIG. 3, the cross-sectional areas of the various vessels (e.g., the aorta, the main coronary arteries, and/or the branches) of the model 220 (FIG. 5) may also be determined (step 304). In an exemplary embodiment, the determination may be performed by the computer system.

The model 220 (FIG. 5) may be trimmed (step 306) and a solid model may be generated. FIG. 8 shows an example of the trimmed solid model 320 prepared based on a model similar to the model 220 shown in FIG. 5. The solid model 320 is a three-dimensional patient-specific geometric model. In an exemplary embodiment, the trimming may be performed by the computer system, with or without a user's input. Each of the inflow boundaries 322 and outflow boundaries 324 may be trimmed such that the surface forming the respective boundary is perpendicular to the centerlines determined in step 242. The inflow boundaries 322 may include the boundaries through which flow is directed into the anatomy of the model 320, such as at an upstream end of the aorta, as shown in FIG. 8. The outflow boundaries 324 may include the boundaries through which flow is directed outward from the anatomy of the model 320, such as at a downstream end of the aorta and the downstream ends of the main coronary arteries and/or branches.

B. Determining Boundary Conditions

Boundary conditions may be provided to describe what is occurring at the boundaries of the model, e.g., the three-dimensional solid model 320 of FIG. 8. For example, the boundary conditions may relate to at least one blood flow characteristic associated with the patient's modeled anatomy, e.g., at the boundaries of the modeled anatomy, and the blood flow characteristic(s) may include blood flow velocity, pressure, flow rate, FFR, etc. By appropriately determining the boundary conditions, a computational analysis may be performed to determine information at various locations within the model. Examples of boundary conditions and methods for determining such boundary conditions will now be described.

In an exemplary embodiment, the determined boundary conditions may simplify the structures upstream and downstream from the portions of the vessels represented by the solid model 320 into a one- or two-dimensional reduced order model. An exemplary set of equations and other details for determining the boundary conditions are disclosed, for example, in U.S. Patent Application Publication No. 2010/0241404 and U.S. Provisional Application No. 61/210,401, which are both entitled "Patient-Specific Hemodynamics of the Cardiovascular System" and hereby incorporated by reference in their entirety.

Figures 9, 10, 11:
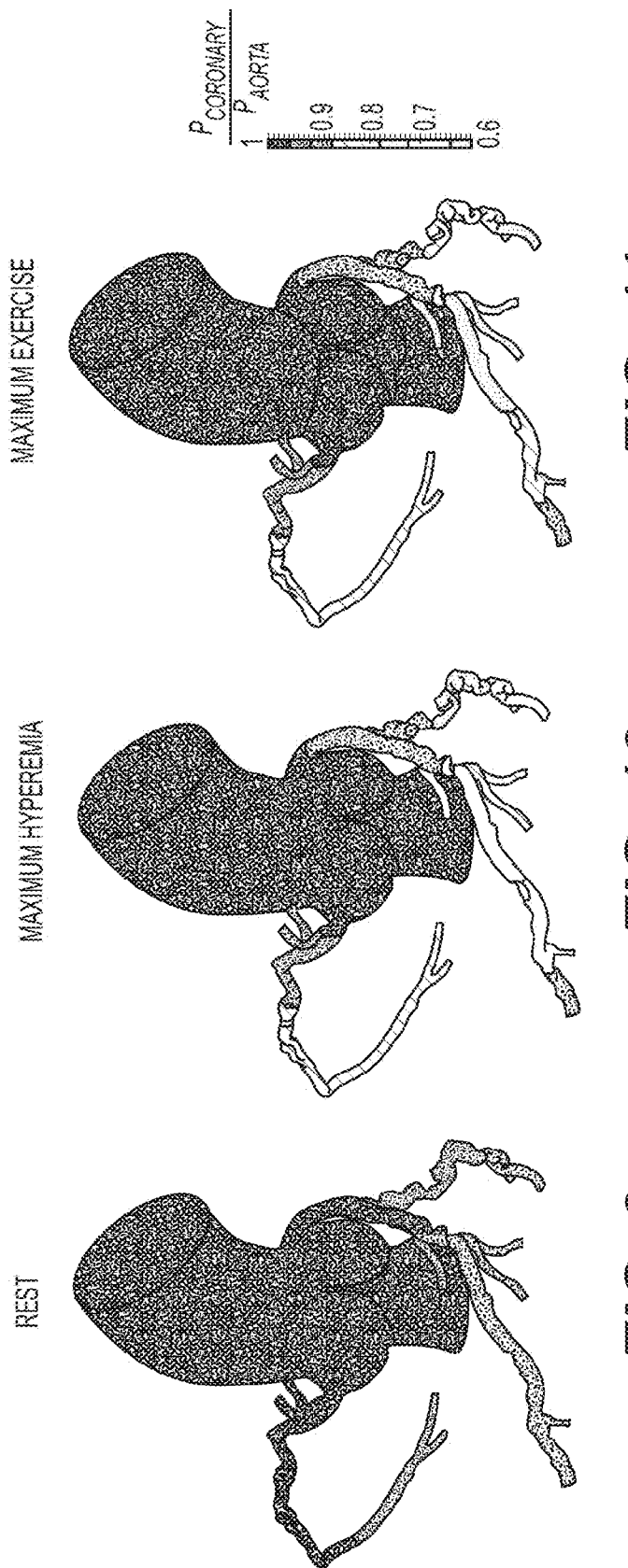
FIG. 9 shows an exemplary computed FFR (cFFR) model when the patient is at rest.
FIG. 10 shows an exemplary cFFR model when the patient is under maximum hyperemia.
FIG. 11 shows an exemplary cFFR model when the patient is under maximum exercise.

Boundary conditions may vary depending on the physiological condition of the patient since blood flow though the heart may differ depending on the physiological condition of the patient. For example, FFR is typically measured under the physiological condition of hyperemia, which generally occurs when the patient is experiencing increased blood flow in the heart, e.g., due to stress, etc. The FFR is the ratio of the coronary pressure to aortic pressure under conditions of maximum stress. Hyperemia may also be induced pharmacologically, e.g., with adenosine. FIGS. 9-11 show examples of a calculated FFR (cFFR) model that indicates the change in the ratio of coronary pressure to aortic pressure in the model 320, depending on the physiological condition of the patient (at rest, under maximum hyperemia, or under maximum exercise). FIG. 9 shows minimal variation in the ratio of coronary pressure to aortic pressure throughout the model 320 when the patient is at rest. FIG. 10 shows greater variation in the ratio of coronary pressure to aortic pressure throughout the model 320 when the patient is undergoing maximum hyperemia. FIG. 11 shows even greater variation in the ratio of coronary pressure to aortic pressure throughout the model 320 when the patient is undergoing maximum exercise.

Referring back to FIG. 3, boundary conditions for hyperemia conditions may be determined (step 310). In an exemplary embodiment, the effect of adenosine may be modeled using a decrease in coronary artery resistance by a factor of 1-5 fold, a decrease in aortic blood pressure of approximately 0-20%, and an increase in heart rate of approximately 0-20%. For example, the effect of adenosine may be modeled using a decrease in coronary artery resistance by a factor of 4 fold, a decrease in aortic blood pressure of approximately 10%, and an increase in heart rate of approximately 10%. Although the boundary conditions for hyperemia conditions are determined in the exemplary embodiment, it is understood that boundary conditions for other physiological states, such as rest, varying degrees of hyperemia, varying degrees of exercise, exertion, stress, or other conditions, may be determined.

Boundary conditions provide information about the three-dimensional solid model 320 at its boundaries, e.g., the inflow boundaries 322, the outflow boundaries 324, vessel wall boundaries 326, etc., as shown in FIG. 8. The vessel wall boundaries 326 may include the physical boundaries of the aorta, the main coronary arteries, and/or other coronary arteries or vessels of the model 320.

Each inflow or outflow boundary 322, 324 may be assigned a prescribed value or field of values for velocity, flow rate, pressure, or other blood flow characteristic. Alternatively, each inflow or outflow boundary 322, 324 may be assigned by coupling a heart model to the boundary, a lumped parameter or distributed (e.g. one-dimensional wave propagation) model, another type of one- or two-dimensional model, or other type of model. The specific boundary conditions may be determined based on, e.g., the geometry of the inflow or outflow boundaries 322, 324 determined from the obtained patient-specific information, or other measured parameters, such as cardiac output, blood pressure, the myocardial mass calculated in step 240, etc.

i. Determining Reduced Order Models

The upstream and downstream structures connected to the solid model 320 may be represented as reduced order models representing the upstream and downstream structures. For example, FIGS. 12-15 show aspects of a method for preparing a lumped parameter model from three-dimensional patient-specific anatomical data at one of the outflow boundaries 324, according to an exemplary embodiment. The method may be performed separately from and prior to the methods shown in FIGS. 2 and 3.

Figure 13:
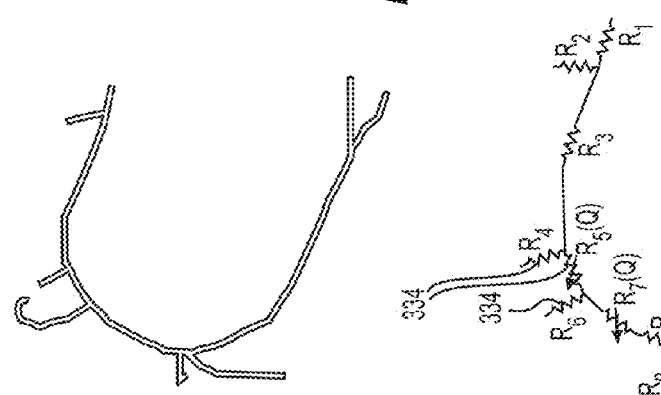
FIG. 13 shows a portion of the centerlines for the trimmed solid model of FIG. 12, provided for forming a lumped parameter model.
Figure 12:
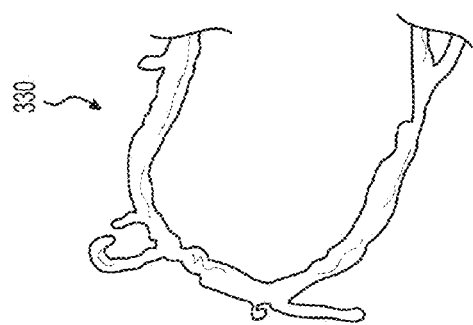
FIG. 12 shows a portion of a trimmed solid model provided for forming a lumped parameter model, according to an exemplary embodiment.

FIG. 12 shows a portion 330 of the solid model 320 of one of the main coronary arteries or the branches extending therefrom, and FIG. 13 shows the portion of the centerlines determined in step 242 of the portion 330 shown in FIG. 12.

Figure 14:
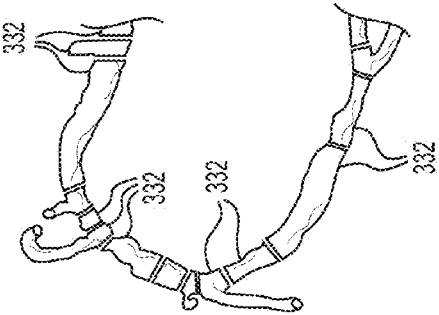
FIG. 14 shows segments formed based on the trimmed solid model of FIG. 12, provided for forming a lumped parameter model.

The portion 330 may be divided into segments 332. FIG. 14 shows an example of the segments 332 that may be formed from the portion 330. The selection of the lengths of the segments 332 may be performed by the user and/or the computer system. The segments 332 may vary in length, depending, for example, on the geometry of the segments 332. Various techniques may be used to segment the portion 330. For example, diseased portions, e.g., portions with a relatively narrow cross-section, a lesion, and/or a stenosis (an abnormal narrowing in a blood vessel), may be provided in one or more separate segments 332. The diseased portions and stenoses may be identified, e.g., by measuring the cross-sectional area along the length of the centerline and calculating locally minimum cross-sectional areas.

Figure 15:
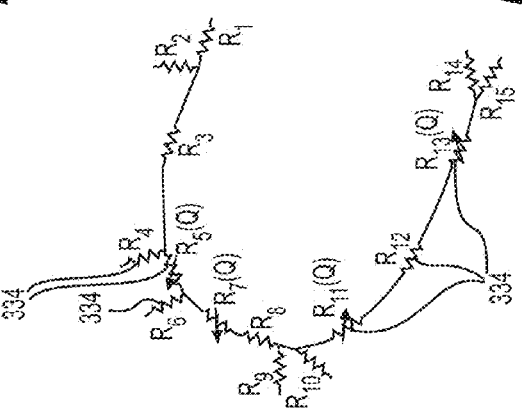
FIG. 15 shows the segments of FIG. 14 replaced by resistors, provided for forming a lumped parameter model.

The segments 332 may be approximated by a circuit diagram including one or more (linear or nonlinear) resistors 334 and/or other circuit elements (e.g., capacitors, inductors, etc.). FIG. 15 shows an example of the segments 332 replaced by a series of linear and nonlinear resistors 334. The individual resistances of the resistors 334 may be determined, e.g., based on an estimated flow and/or pressure across the corresponding segment 332.

The resistance may be constant, linear, or non-linear, e.g., depending on the estimated flow rate through the corresponding segment 332. For more complex geometries, such as a stenosis, the resistance may vary with flow rate. Resistances for various geometries may be determined based on a computational analysis (e.g., a finite difference, finite volume, spectral, lattice Boltzmann, particle-based, level set, isogeometric, or finite element method, or other computational fluid dynamics (CFD) analytical technique), and multiple solutions from the computational analysis performed under different flow and pressure conditions may be used to derive patient-specific, vessel-specific, and/or lesion-specific resistances. The results may be used to determine resistances for various types of features and geometries of any segment that may be modeled. As a result, deriving patient-specific, vessel-specific, and/or lesion-specific resistances as described above may allow the computer system to recognize and evaluate more complex geometry such as asymmetric stenosis, multiple lesions, lesions at bifurcations and branches and tortuous vessels, etc.

Capacitors may be also included, and capacitance may be determined, e.g., based on elasticity of the vessel walls of the corresponding segment. Inductors may be included, and inductance may be determined, e.g., based on inertial effects related to acceleration or deceleration of the blood volume flowing through the corresponding segment.

The individual values for resistance, capacitance, inductance, and other variables associated with other electrical components used in the lumped parameter model may be derived based on data from many patients, and similar vessel geometries may have similar values. Thus, empirical models may be developed from a large population of patient-specific data, creating a library of values corresponding to specific geometric features that may be applied to similar patients in future analyses. Geometries may be matched between two different vessel segments to automatically select the values for a segment 332 of a patient from a previous simulation.

ii. Exemplary Lumped Parameter Models

Figure 16:
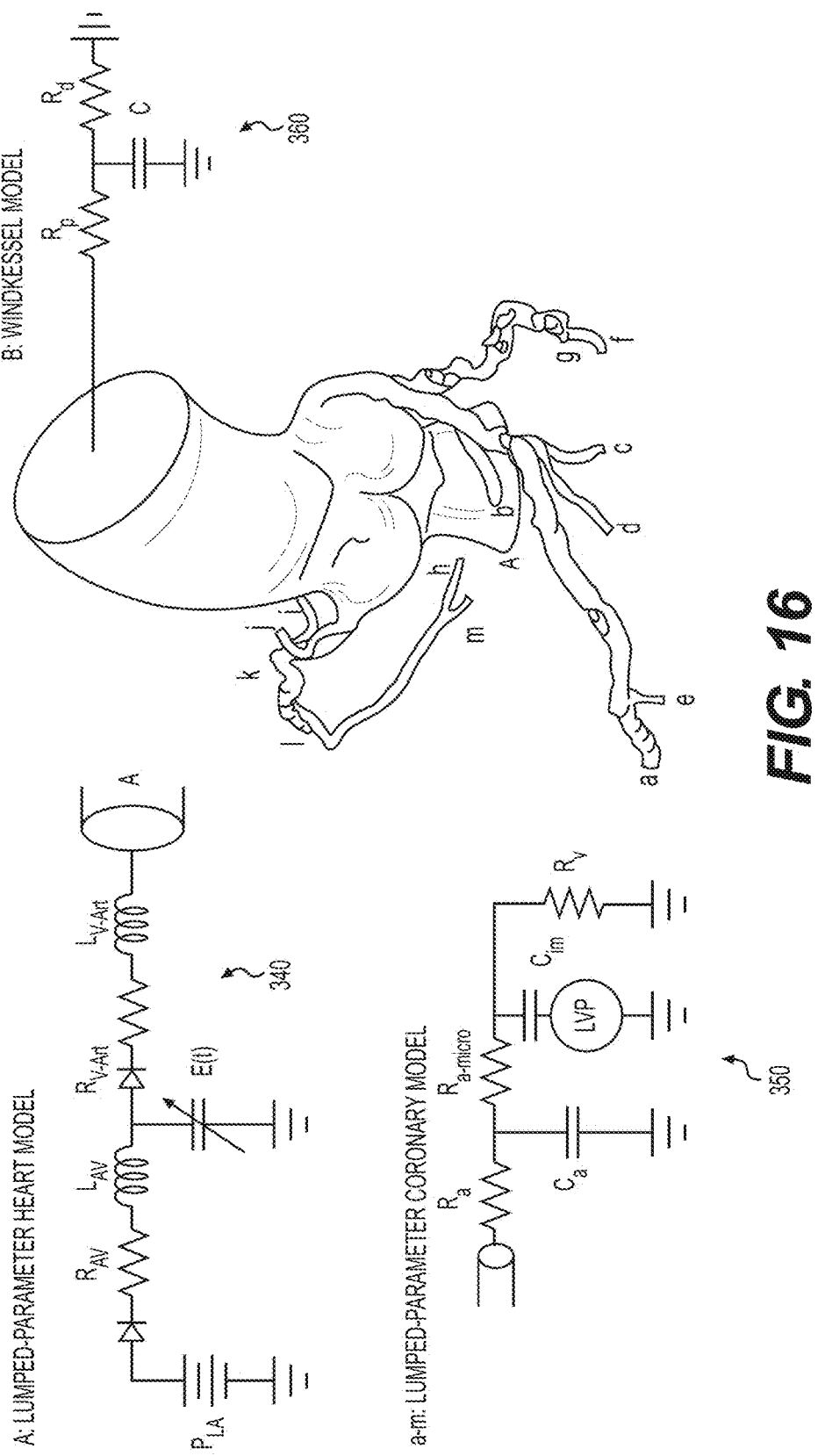
FIG. 16 shows exemplary lumped parameter models representing the upstream and downstream structures at the inflow and outflow boundaries of a solid model, according to an exemplary embodiment.

Alternatively, instead of performing the steps described above in connection with FIGS. 12-15, the lumped parameter models may be preset. For example, FIG. 16 shows examples of lumped parameter models 340, 350, 360 representing the upstream and downstream structures at the inflow and outflow boundaries 322, 324 of the solid model 320. End A is located at the inflow boundary 322, and ends a-m and B are located at the outflow boundaries.

A lumped parameter heart model 340 may be used to determine the boundary condition at the end A at the inflow boundary 322 of the solid model 320. The lumped parameter heart model 340 may be used to represent blood flow from the heart under hyperemia conditions. The lumped parameter heart model 340 includes various parameters (e.g., $P_{LA}$, $R_{AV}$, $L_{AV}$, $R_{V\text{-}Art}$, $L_{V\text{-}Art}$, and E(t)) that may be determined based on known information regarding the patient, e.g., an aortic pressure, the patient's systolic and diastolic blood pressures (e.g., as determined in step 100), the patient's cardiac output (the volume of blood flow from the heart, e.g., calculated based on the patient's stroke volume and heart rate determined in step 100), and/or constants determined experimentally.

A lumped parameter coronary model 350 may be used to determine the boundary conditions at the ends a-m at the outflow boundaries 324 of the solid model 320 located at the downstream ends of the main coronary arteries and/or the branches that extend therefrom. The lumped parameter coronary model 350 may be used to represent blood flow exiting from the modeled vessels through the ends a-m under hyperemia conditions. The lumped parameter coronary model 350 includes various parameters (e.g., $R_a$, $C_a$, $R_{a\text{-}micro}$, $C_{im}$, and $R_V$) that may be determined based on known information regarding the patient, e.g., the calculated myocardial mass (e.g., as determined in step 240) and terminal impedance at the ends a-m (e.g., determined based on the cross-sectional areas of the vessels at the ends a-m as determined in step 304).

For example, the calculated myocardial mass may be used to estimate a baseline (resting) mean coronary flow through the plurality of outflow boundaries 324. This relationship may be based on an experimentally-derived physiological law (e.g., of the physiological laws 20 of FIG. 1) that correlates the mean coronary flow Q with the myocardial mass M (e.g., as determined in step 240) as $Q \propto Q_o M^\alpha$, where $\alpha$ is a preset scaling exponent and $Q_o$ is a preset constant. The total coronary flow Q at the outflow boundaries 324 under baseline (resting) conditions and the patient's blood pressure (e.g., as determined in step 100) may then be used to determine a total resistance Rat the outflow boundaries 324 based on a preset, experimentally-derived equation.

The total resistance R may be distributed among the ends a-m based on the respective cross-sectional areas of the ends a-m (e.g., as determined in step 304). This relationship may be based on an experimentally-derived physiological law (e.g., of the physiological laws 20 of FIG. 1) that correlates the respective resistance at the ends a-m as $R_i \propto R_{i,o} d_i^\beta$ where $R_i$ is the resistance to flow at the i-th outlet, and $R_{i,o}$ is a preset constant, $d_i$ is the diameter of that outlet, and $\beta$ is a preset power law exponent, e.g., between −3 and −2, −2.7 for coronary flow, −2.9 for cerebral flow, etc. The coronary flow through the individual ends a-m and the mean pressures at the individual ends a-m (e.g., determined based on the individual cross-sectional areas of the ends a-m of the vessels as determined in step 304) may be used to determine a sum of the resistances of the lumped parameter coronary model 350 at the corresponding ends a-m (e.g., $R_a + R_{a\text{-}micro} R_V$). Other parameters (e.g., $R_a/R_{a\text{-}micro}$, $C_a$, $C_{im}$) may be constants determined experimentally.

A Windkessel model 360 may be used to determine the boundary condition at the end B at the outflow boundary 324 of the solid model 320 located at the downstream end of the aorta toward the aortic arch. The Windkessel model 360 may be used to represent blood flow exiting from the modeled aorta through the end B under hyperemia conditions. The Windkessel model 360 includes various parameters (e.g., $R_P$, $R_d$, and C) that may be determined based on known information regarding the patient, e.g., the patient's cardiac output described above in connection with the lumped parameter heart model 340, the baseline mean coronary flow described above in connection with the lumped parameter coronary model 350, an aortic pressure (e.g., determined based on the cross-sectional area of the aorta at the end B as determined in step 304), and/or constants determined experimentally.

The boundary conditions, e.g., the lumped parameter models 340, 350, 360 (or any of the constants included therein) or other reduced order model, may be adjusted based on other factors. For example, resistance values may be adjusted (e.g., increased) if a patient has a lower flow to vessel size ratio due to a comparatively diminished capacity to dilate vessels under physiologic stress. Resistance values may also be adjusted if the patient has diabetes, is under medication, has undergone past cardiac events, etc.

Alternate lumped parameter or distributed, one-dimensional network models may be used to represent the coronary vessels downstream of the solid model 320. Myocardial perfusion imaging using MRI, CT, PET, or SPECT may be used to assign parameters for such models. Also, alternate imaging sources, e.g., magnetic resonance angiography (MRA), retrospective cine gating or prospective cine gating computed tomography angiography (CTA), etc., may be used to assign parameters for such models. Retrospective cine gating may be combined with image processing methods to obtain ventricular chamber volume changes over the cardiac cycle to assign parameters to a lumped parameter heart model.

Simplifying a portion of the patient's anatomy using the lumped parameter models 340, 350, 360, or other reduced order one- or two-dimensional model allows the computational analysis (e.g., step 402 of FIG. 3 described below) to be performed more quickly, particularly if the computational analysis is performed multiple times such as when evaluating possible treatment options (e.g., step 500 of FIG. 2) in addition to the untreated state (e.g., step 400 of FIGS. 2 and 3), while maintaining high accuracy with the final results.

In an exemplary embodiment, the determination of the boundary conditions may be performed by the computer system based on the user's inputs, such as patient-specific physiological data obtained in step 100.

C. Creating the Three-Dimensional Mesh

Referring back to FIG. 3, a three-dimensional mesh may be generated based on the solid model 320 generated in step 306 (step 312). FIGS. 17-19 show an example of a three-dimensional mesh 380 prepared based on the solid model 320 generated in step 306. The mesh 380 includes a plurality of nodes 382 (meshpoints or gridpoints) along the surfaces of the solid model 320 and throughout the interior of the solid model 320. The mesh 380 may be created with tetrahedral elements (having points that form the nodes 382), as shown in FIGS. 18 and 19. Alternatively, elements having other shapes may be used, e.g., hexahedrons or other polyhedrons, curvilinear elements, etc. In an exemplary embodiment, the number of nodes 382 may be in the millions, e.g., five to fifty million. The number of nodes 382 increases as the mesh 380 becomes finer. With a higher number of nodes 382, information may be provided at more points within the model 320, but the computational analysis may take longer to run since a greater number of nodes 382 increases the number of equations (e.g., the equations 30 shown in FIG. 1) to be solved. In an exemplary embodiment, the generation of the mesh 380 may be performed by the computer system, with or without a user's input (e.g., specifying a number of the nodes 382, the shapes of the elements, etc.).

Referring back to FIG. 3, the mesh 380 and the determined boundary conditions may be verified (step 314). The verification may be performed by a user and/or by the computer system. For example, the user and/or computer system may be able to identify certain errors with the mesh 380 and/or the boundary conditions that require the mesh 380 and/or the boundary conditions to be redone, e.g., if the mesh 380 is distorted or does not have sufficient spatial resolution, if the boundary conditions are not sufficient to perform the computational analysis, if the resistances determined in step 310 appear to be incorrect, etc. If so, then the mesh 380 and/or the boundary conditions may be determined to be unacceptable, and one or more of steps 304-314 may be repeated. If the mesh 380 and/or the boundary conditions are determined to be acceptable, then the method may proceed to step 402 described below.

In addition, the user may check that the obtained patient-specific information, or other measured parameters, such as cardiac output, blood pressures, height, weight, the myocardial mass calculated in step 240, are entered correctly and/or calculated correctly.

Accordingly, steps 304-314 shown in FIG. 3 and described above may be considered as substeps of step 300 of FIG. 2.

V. Performing the Computational Analysis and Outputting Results

As described above in connection with step 400 shown in FIG. 2, the exemplary method may include performing the computational analysis and outputting results. In an exemplary embodiment, step 400 may include the following steps.

A. Performing the Computational Analysis

Referring to FIG. 3, the computational analysis may be performed by the computer system (step 402). In an exemplary embodiment, step 402 may last minutes to hours, depending, e.g., on the number of nodes 382 in the mesh 380 (FIGS. 17-19), etc.

The analysis involves generating a series of equations that describe the blood flow in the model 320 from which the mesh 380 was generated. As described above, in the exemplary embodiment, the desired information relates to the simulation of blood flow through the model 320 under hyperemic conditions.

The analysis also involves using a numerical method to solve the three-dimensional equations of blood flow using the computer system. For example, the numerical method may be a known method, such as finite difference, finite volume, spectral, lattice Boltzmann, particle-based, level set, isogeometric, or finite element methods, or other computational fluid dynamics (CFD) numerical techniques.

Using these numerical methods, the blood may be modeled as a Newtonian, a non-Newtonian, or a multiphase fluid. The patient's hematocrit or other factors measured in step 100 may be used to determine blood viscosity for incorporation in the analysis. The blood vessel walls may be assumed to be rigid or compliant. In the latter case, equations for wall dynamics, e.g., the elastodynamics equations, may be solved together with the equations for blood flow. Time-varying three-dimensional imaging data obtained in step 100 may be used as an input to model changes in vessel shape over the cardiac cycle. An exemplary set of equations and steps for performing the computational analysis are disclosed in further detail, for example, in U.S. Pat. No. 6,236,878, which is entitled "Method for Predictive Modeling for Planning Medical Interventions and Simulating Physiological Conditions," and U.S. Patent Application Publication No. 2010/0241404 and U.S. Provisional Application No. 61/210,401, which are both entitled "Patient-Specific Hemodynamics of the Cardiovascular System," all of which are hereby incorporated by reference in their entirety.

The computational analysis using the prepared model and boundary conditions may determine blood flow and pressure at each of the nodes 382 of the mesh 380 representing the three-dimensional solid model 320. For example, the results of the computational analysis may include values for various parameters at each of the nodes 382, such as, but not limited to, various blood flow characteristics or parameters, such as blood flow velocity, pressure, flow rate, or computed parameters, such as cFFR, as described below. The parameters may also be interpolated across the three-dimensional solid model 320. As a result, the results of the computational analysis may provide the user with information that typically may be determined invasively.

Referring back to FIG. 3, the results of the computational analysis may be verified (step 404). The verification may be performed by a user and/or by the computer system. For example, the user and/or computer system may be able to identify certain errors with the results that require the mesh 380 and/or the boundary conditions to be redone or revised, e.g., if there is insufficient information due to an insufficient number of nodes 382, if the analysis is taking too long due to an excessive number of nodes 382, etc.

If the results of the computational analysis are determined to be unacceptable in step 404, then the user and/or computer system may determine, for example, whether and how to revise or refine the solid model 320 generated in step 306 and/or the mesh 380 generated in step 312, whether and how to revise the boundary conditions determined in step 310, or whether to make other revisions to any of the inputs for the computational analysis. Then, one or more steps described above, e.g., steps 306-314, 402, and 404 may be repeated based on the determined revisions or refinements.

B. Displaying Results for Blood Pressure, Flow, and cFFR

Referring back to FIG. 3, if the results of the computational analysis are determined to be acceptable in step 404, then the computer system may output certain results of the computational analysis. For example, the computer system may display images generated based on the results of the computational analysis, such as the images described above in connection with FIG. 1, such as the simulated blood pressure model 50, the simulated blood flow model 52, and/or the cFFR model 54. As noted above, these images indicate the simulated blood pressure, blood flow, and cFFR under simulated hyperemia conditions, e.g., since the boundary conditions determined in step 310 were determined with respect to hyperemia conditions.

The simulated blood pressure model 50 (FIG. 1) shows the local blood pressure (e.g., in millimeters of mercury or mmHg) throughout the patient's anatomy represented by the mesh 380 of FIGS. 17-19 under simulated hyperemia conditions. The computational analysis may determine the local blood pressure at each node 382 of the mesh 380, and the simulated blood pressure model 50 may assign a corresponding color, shade, or other visual indicator to the respective pressures such that the simulated blood pressure model 50 may visually indicate the variations in pressure throughout the model 50 without having to specify the individual values for each node 382. For example, the simulated blood pressure model 50 shown in FIG. 1 shows that, for this particular patient, under simulated hyperemia conditions, the pressure may be generally uniform and higher in the aorta (as indicated by the darker shading), and that the pressure gradually and continuously decreases as the blood flows downstream into the main coronary arteries and into the branches (as shown by the gradual and continuous lightening in shading toward the downstream ends of the branches). The simulated blood pressure model 50 may be accompanied by a scale indicating the specific numerical values for blood pressure, as shown in FIG. 1.

In an exemplary embodiment, the simulated blood pressure model 50 may be provided in color, and a color spectrum may be used to indicate variations in pressure throughout the model 50. The color spectrum may include red, orange, yellow, green, blue, indigo, and violet, in order from highest pressure to lowest pressure. For example, the upper limit (red) may indicate approximately 110 mmHg or more (or 80 mmHg, 90 mmHg, 100 mmHg, etc.), and the lower limit (violet) may indicate approximately 50 mmHg or less (or 20 mmHg, 30 mmHg, 40 mmHg, etc.), with green indicating approximately 80 mmHg (or other value approximately halfway between the upper and lower limits). Thus, the simulated blood pressure model 50 for some patients may show a majority or all of the aorta as red or other color towards the higher end of the spectrum, and the colors may change gradually through the spectrum (e.g., towards the lower end of the spectrum (down to violet)) towards the distal ends of the coronary arteries and the branches that extend therefrom. The distal ends of the coronary arteries for a particular patient may have different colors, e.g., anywhere from red to violet, depending on the local blood pressures determined for the respective distal ends.

The simulated blood flow model 52 (FIG. 1) shows the local blood velocity (e.g., in centimeters per second or cm/s) throughout the patient's anatomy represented by the mesh 380 of FIGS. 17-19 under simulated hyperemia conditions. The computational analysis may determine the local blood velocity at each node 382 of the mesh 380, and the simulated blood flow model 52 may assign a corresponding color, shade, or other visual indicator to the respective velocities such that the simulated blood flow model 52 may visually indicate the variations in velocity throughout the model 52 without having to specify the individual values for each node 382. For example, the simulated blood flow model 52 shown in FIG. 1 shows that, for this particular patient, under simulated hyperemia conditions, the velocity is generally higher in certain areas of the main coronary arteries and the branches (as indicated by the darker shading in area 53 in FIG. 1). The simulated blood flow model 52 may be accompanied by a scale indicating the specific numerical values for blood velocity, as shown in FIG. 1.

In an exemplary embodiment, the simulated blood flow model 52 may be provided in color, and a color spectrum may be used to indicate variations in velocity throughout the model 52. The color spectrum may include red, orange, yellow, green, blue, indigo, and violet, in order from highest velocity to lowest velocity. For example, the upper limit (red) may indicate approximately 100 (or 150) cm/s or more, and the lower limit (violet) may indicate approximately 0 cm/s, with green indicating approximately 50 cm/s (or other value approximately halfway between the upper and lower limits). Thus, the simulated blood flow model 52 for some patients may show a majority or all of the aorta as a mixture of colors towards the lower end of the spectrum (e.g., green through violet), and the colors may change gradually through the spectrum (e.g., towards the higher end of the spectrum (up to red)) at certain locations where the determined blood velocities increase.

The cFFR model 54 (FIG. 1) shows the local cFFR throughout the patient's anatomy represented by the mesh 380 of FIGS. 17-19 under simulated hyperemia conditions. As noted above, cFFR may be calculated as the ratio of the local blood pressure determined by the computational analysis (e.g., shown in the simulated blood pressure model 50) at a particular node 382 divided by the blood pressure in the aorta, e.g., at the inflow boundary 322 (FIG. 8). The computational analysis may determine the cFFR at each node 382 of the mesh 380, and the cFFR model 54 may assign a corresponding color, shade, or other visual indicator to the respective cFFR values such that the cFFR model 54 may visually indicate the variations in cFFR throughout the model 54 without having to specify the individual values for each node 382. For example, the cFFR model 54 shown in FIG. 1 shows that, for this particular patient, under simulated hyperemia conditions, cFFR may be generally uniform and approximately 1.0 in the aorta, and that cFFR gradually and continuously decreases as the blood flows downstream into the main coronary arteries and into the branches. The cFFR model 54 may also indicate cFFR values at certain points throughout the cFFR model 54, as shown in FIG. 1. The cFFR model 54 may be accompanied by a scale indicating the specific numerical values for cFFR, as shown in FIG. 1.

In an exemplary embodiment, the cFFR model 54 may be provided in color, and a color spectrum may be used to indicate variations in pressure throughout the model 54. The color spectrum may include red, orange, yellow, green, blue, indigo, and violet, in order from lowest cFFR (indicating functionally significant lesions) to highest cFFR. For example, the upper limit (violet) may indicate a cFFR of 1.0, and the lower limit (red) may indicate approximately 0.7 (or 0.75 or 0.8) or less, with green indicating approximately 0.85 (or other value approximately halfway between the upper and lower limits). For example, the lower limit may be determined based on a lower limit (e.g., 0.7, 0.75, or 0.8) used for determining whether the cFFR measurement indicates a functionally significant lesion or other feature that may require intervention. Thus, the cFFR model 54 for some patients may show a majority or all of the aorta as violet or other color towards the higher end of the spectrum, and the colors may change gradually through the spectrum (e.g., towards the higher end of the spectrum (up to anywhere from red to violet) towards the distal ends of the coronary arteries and the branches that extend therefrom. The distal ends of the coronary arteries for a particular patient may have different colors, e.g., anywhere from red to violet, depending on the local values of cFFR determined for the respective distal ends.

After determining that the cFFR has dropped below the lower limit used for determining the presence of a functionally significant lesion or other feature that may require intervention, the artery or branch may be assessed to locate the functionally significant lesion(s). The computer system or the user may locate the functionally significant lesion(s) based on the geometry of the artery or branch (e.g., using the cFFR model 54). For example, the functionally significant lesion(s) may be located by finding a narrowing or stenosis located near (e.g., upstream) from the location of the cFFR model 54 having the local minimum cFFR value. The computer system may indicate or display to the user the portion(s) of the cFFR model 54 (or other model) that includes the functionally significant lesion(s).

Figure 21:
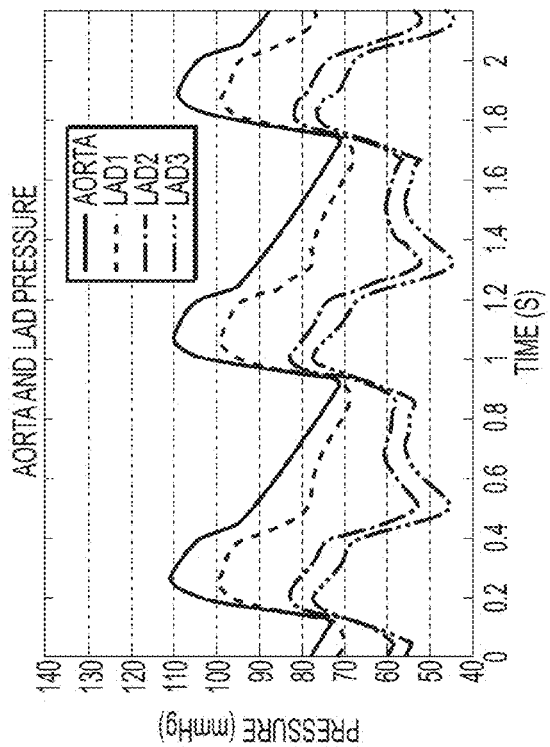
FIG. 21 is a graph of simulated blood pressure over time in the aorta and at some of the points identified in FIG. 20.
Figure 22:
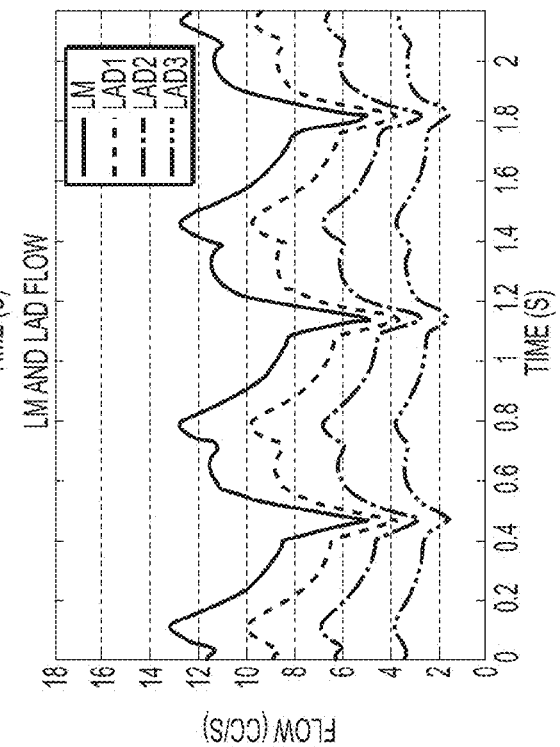
FIG. 22 is a graph of simulated blood flow over time at each of the points identified in FIG. 20.
Figure 20:
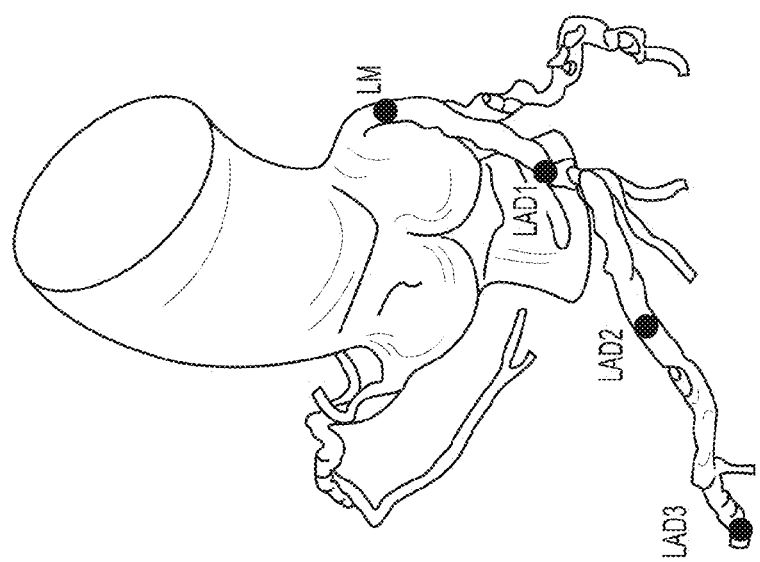
FIG. 20 shows a model of the patient's anatomy including blood flow information with certain points on the model identified by individual reference labels.

Other images may also be generated based on the results of the computational analysis. For example, the computer system may provide additional information regarding particular main coronary arteries, e.g., as shown in FIGS. 20-22. The coronary artery may be chosen by the computer system, for example, if the particular coronary artery includes the lowest cFFR. Alternatively, the user may select the particular coronary artery.

FIG. 20 shows a model of the patient's anatomy including results of the computational analysis with certain points on the model identified by individual reference labels (e.g., LM, LAD1, LAD2, LAD3, etc.). In the exemplary embodiment shown in FIG. 21, the points are provided in the LAD artery, which is the main coronary artery having the lowest cFFR for this particular patient, under simulated hyperemia conditions.

FIGS. 21 and 22 show graphs of certain variables over time at some or all of these points (e.g., LM, LAD1, LAD2, LAD3, etc.) and/or at certain other locations on the model (e.g., in the aorta, etc.). FIG. 21 is a graph of the pressure (e.g., in millimeters of mercury or mmHg) over time in the aorta and at points LAD1, LAD2, and LAD3 indicated in FIG. 20. The top plot on the graph indicates the pressure in the aorta, the second plot from the top indicates the pressure at point LAD1, the third plot from the top indicates the pressure at point LAD2, and the bottom plot indicates the pressure at point LAD3. FIG. 22 is a graph of the flow (e.g., in cubic centimeters per second or cc/s) over time at points LM, LAD1, LAD2, and LAD3 indicated in FIG. 20. In addition, other graphs may be provided, such as a graph of shear stress over time at some or all of these points and/or at other points. The top plot on the graph indicates the flow at point LM, the second plot from the top indicates the flow at point LAD1, the third plot from the top indicates the flow at point LAD2, and the bottom plot indicates the flow at point LAD3. Graphs may also be provided that show the change in these variables, e.g., blood pressure, flow, velocity, or cFFR, along the length of a particular main coronary artery and/or the branches extending therefrom.

Optionally, the various graphs and other results described above may be finalized in a report (step 406). For example, the images and other information described above may be inserted into a document having a set template. The template may be preset and generic for multiple patients, and may be used for reporting the results of computational analyses to physicians and/or patients. The document or report may be automatically completed by the computer system after the computational analysis is completed.

Figure 23:
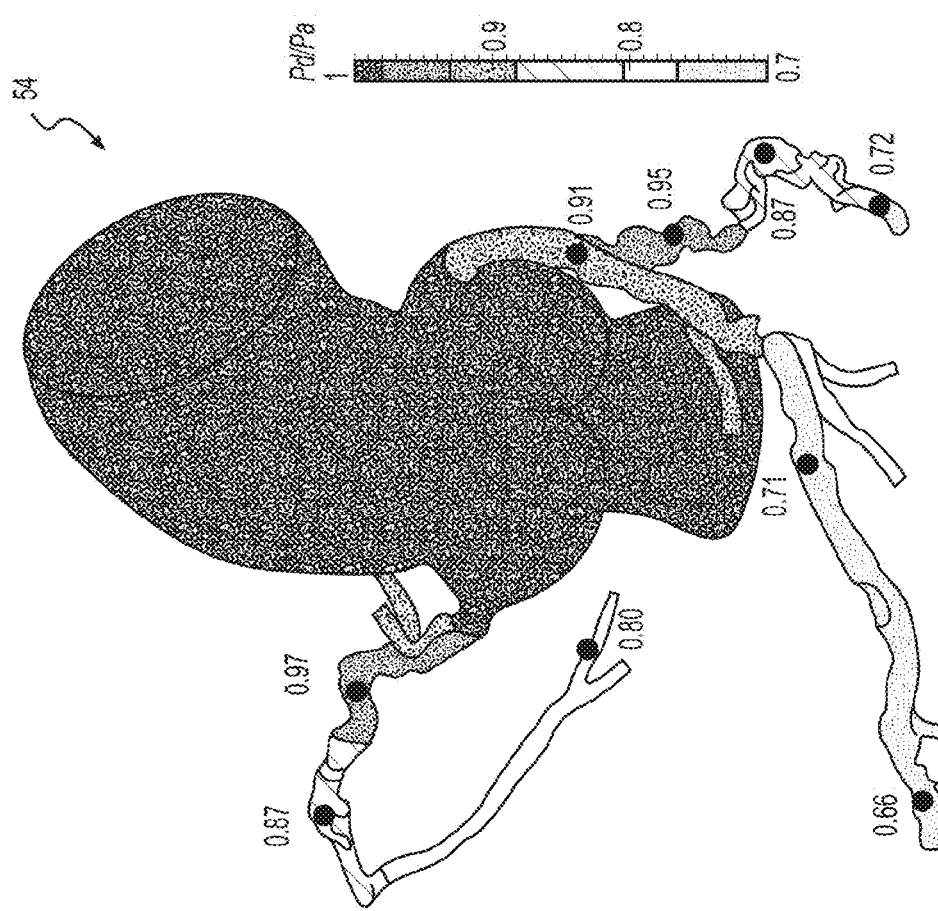
FIG. 23 is a finalized report, according to an exemplary embodiment.

For example, the finalized report may include the information shown in FIG. 23. FIG. 23 includes the cFFR model 54 of FIG. 1 and also includes summary information, such as the lowest cFFR values in each of the main coronary arteries and the branches that extend therefrom. For example, FIG. 23 indicates that the lowest cFFR value in the LAD artery is 0.66, the lowest cFFR value in the LCX artery is 0.72, the lowest cFFR value in the RCA artery is 0.80. Other summary information may include the patient's name, the patient's age, the patient's blood pressure (BP) (e.g., obtained in step 100), the patient's heart rate (HR) (e.g., obtained in step 100), etc. The finalized report may also include versions of the images and other information generated as described above that the physician or other user may access to determine further information. The images generated by the computer system may be formatted to allow the physician or other user to position a cursor over any point to determine the value of any of the variables described above, e.g., blood pressure, velocity, flow, cFFR, etc., at that point.

The finalized report may be transmitted to the physician and/or the patient. The finalized report may be transmitted using any known method of communication, e.g., a wireless or wired network, by mail, etc. Alternatively, the physician and/or patient may be notified that the finalized report is available for download or pick-up. Then, the physician and/or patient may log into the web-based service to download the finalized report via a secure communication line.

C. Verifying Results

Referring back to FIG. 3, the results of the computational analysis may be independently verified (step 408). For example, the user and/or computer system may be able to identify certain errors with the results of the computational analysis, e.g., the images and other information generated in step 406, that require any of the above described steps to be redone. If such errors are identified, then the results of the computational analysis may be determined to be unacceptable, and certain steps, e.g., steps 100, 200, 300, 400, substeps 102, 202-208, 240-260, 304-314, and 402-408, etc., may be repeated.

Accordingly, steps 402-408 shown in FIG. 3 and described above may be considered as substeps of step 400 of FIG. 2.

Another method for verifying the results of the computational analysis may include measuring any of the variables included in the results, e.g., blood pressure, velocity, flow, cFFR, etc., from the patient using another method. In an exemplary embodiment, the variables may be measured (e.g., invasively) and then compared to the results determined by the computational analysis. For example, FFR may be determined, e.g., using a pressure wire inserted into the patient as described above, at one or more points within the patient's anatomy represented by the solid model 320 and the mesh 380. The measured FFR at a location may be compared with the cFFR at the same location, and the comparison may be performed at multiple locations. Optionally, the computational analysis and/or boundary conditions may be adjusted based on the comparison.

Figure 24:
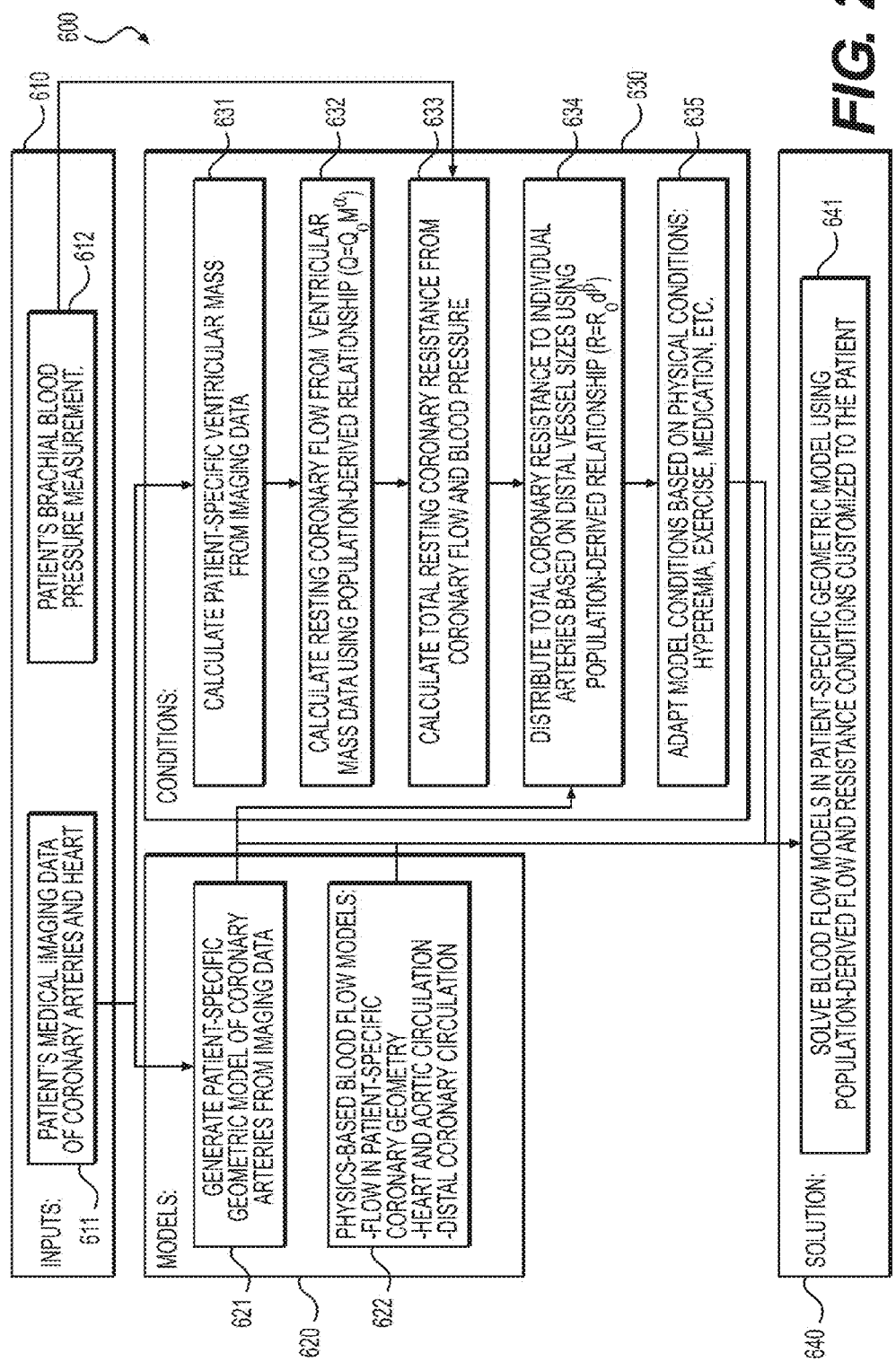
FIG. 24 is a flow chart of a method for providing various information relating to coronary blood flow in a specific patient, according to an exemplary embodiment.

D. Another Embodiment of a System and Method for Providing Coronary Blood Flow Information Another embodiment of a method 600 for providing various information relating to coronary blood flow in a specific patient is shown in FIG. 24. The method 600 may be implemented in the computer system described above, e.g., the computer system used to implement one or more of the steps described above and shown in FIG. 3. The method 600 may be performed using one or more inputs 610, and may include generating one or more models 620 based on the inputs 610, assigning one or more conditions 630 based on the inputs 610 and/or the models 620, and deriving one or more solutions 640 based on the models 620 and the conditions 630.

The inputs 610 may include medical imaging data 611 of the patient's aorta, coronary arteries (and the branches that extend therefrom), and heart, such as CCTA data (e.g., obtained in step 100 of FIG. 2). The inputs 610 may also include a measurement 612 of the patient's brachial blood pressure and/or other measurements (e.g., obtained in step 100 of FIG. 2). The measurements 612 may be obtained noninvasively. The inputs 610 may be used to generate the model(s) 620 and/or determine the condition(s) 630 described below.

As noted above, one or more models 620 may be generated based on the inputs 610. For example, the method 600 may include generating one or more patient-specific three-dimensional geometric models of the patient's anatomy (e.g., the aorta, coronary arteries, and branches that extend therefrom) based on the imaging data 611 (step 621). For example, the geometric model may be the solid model 320 of FIG. 8 generated in step 306 of FIG. 3, and/or the mesh 380 of FIGS. 17-19 generated in step 312 of FIG. 3.

Referring back to FIG. 24, the method 600 may also include generating one or more physics-based blood flow models (step 622). The blood flow models may include a model that relates to blood flow through the patient-specific geometric model generated in step 621, heart and aortic circulation, distal coronary circulation, etc. The blood flow models may relate to at least one blood flow characteristic associated with the patient's modeled anatomy, e.g., blood flow velocity, pressure, flow rate, FFR, etc. The blood flow models may be assigned as boundary conditions at the inflow and outflow boundaries 322, 324 of the three-dimensional geometric model. The blood flow model may include the reduced order models or other boundary conditions described above in connection with step 310 of FIG. 3, e.g., the lumped parameter heart model 340, the lumped parameter coronary model 350, the Windkessel model 360, etc.

As noted above, one or more conditions 630 may be determined based on the inputs 610 and/or the models 620. The conditions 630 include the parameters calculated for the boundary conditions determined in step 622 (and step 310 of FIG. 3). For example, the method 600 may include determining a condition by calculating a patient-specific ventricular or myocardial mass based on the imaging data 611 (e.g., as determined in step 240 of FIG. 3) (step 631).

The method 600 may include determining a condition by calculating, using the ventricular or myocardial mass calculated in step 631, a resting coronary flow based on the relationship $Q=Q_o M^\alpha$, where $\alpha$ is a preset scaling exponent, M is the ventricular or myocardial mass, and $Q_o$ is a preset constant (e.g., as described above in connection with determining the lumped parameter model in step 310 of FIG. 3) (step 632). Alternatively, the relationship may have the form $Q \propto Q_o M^\alpha$, as described above in connection with determining the lumped parameter model in step 310 of FIG. 3.

The method 600 may also include determining a condition by calculating, using the resulting coronary flow calculated in step 632 and the patient's measured blood pressure 612, a total resting coronary resistance (e.g., as described above in connection with determining the lumped parameter model in step 310 of FIG. 3) (step 633).

The method 600 may also include determining a condition by calculating, using the total resting coronary resistance calculated in step 633 and the models 620, individual resistances for the individual coronary arteries (and the branches that extend therefrom) (step 634). For example, as described above in connection with step 310 of FIG. 3, the total resting coronary resistance calculated in step 633 may be distributed to the individual coronary arteries and branches based on the sizes (e.g., determined from the geometric model generated in step 621) of the distal ends of the individual coronary arteries and branches, and based on the relationship $R=R_o d^\beta$, where R is the resistance to flow at a particular distal end, and $R_o$ is a preset constant, d is the size (e.g., diameter of that distal end), and $\beta$ is a preset power law exponent, as described above in connection with determining the lumped parameter model in step 310 of FIG. 3.

Referring back to FIG. 24, the method 600 may include adjusting the boundary conditions based on one or more physical conditions of the patient (step 635). For example, the parameters determined in steps 631-634 may be modified based on whether the solution 640 is intended to simulate rest, varying levels of hyperemia, varying levels of exercise or exertion, different medications, etc. Based on the inputs 610, the models 620, and the conditions 630, a computational analysis may be performed, e.g., as described above in connection with step 402 of FIG. 3, to determine the solution 640 that includes information about the patient's coronary blood flow under the physical conditions selected in step 635 (step 641). Examples of information that may be provided from the solution 640 will now be described.

The combined patient-specific anatomic (geometric) and physiologic (physics-based) model may be used to determine the effect of different medications or lifestyle changes (e.g., cessation of smoking, changes in diet, or increased physical activity) that alters heart rate, stroke volume, blood pressure, or coronary microcirculatory function on coronary artery blood flow. Such information may be used to optimize medical therapy or avert potentially dangerous consequences of medications. The combined model may also be used to determine the effect on coronary artery blood flow of alternate forms and/or varying levels of physical activity or risk of exposure to potential extrinsic force, e.g., when playing football, during space flight, when scuba diving, during airplane flights, etc. Such information may be used to identify the types and level of physical activity that may be safe and efficacious for a specific patient. The combined model may also be used to predict a potential benefit of percutaneous coronary interventions on coronary artery blood flow in order to select the optimal interventional strategy, and/or to predict a potential benefit of coronary artery bypass grafting on coronary artery blood flow in order to select the optimal surgical strategy.

The combined model may also be used to illustrate potential deleterious effects of an increase in the burden of arterial disease on coronary artery blood flow and to predict, using mechanistic or phenomenological disease progression models or empirical data, when advancing disease may result in a compromise of blood flow to the heart muscle. Such information may enable the determination of a "warranty period" in which a patient observed to be initially free from hemodynamically significant disease using noninvasive imaging may not be expected to require medical, interventional, or surgical therapy, or alternatively, the rate at which progression might occur if adverse factors are continued.

The combined model may also be used to illustrate potential beneficial effects on coronary artery blood flow resulting from a decrease in the burden of coronary artery disease and to predict, using mechanistic or phenomenological disease progression models or empirical data, when regression of disease may result in increased blood flow through the coronary arteries to the heart muscle. Such information may be used to guide medical management programs including, but not limited to, changes in diet, increased physical activity, prescription of statins or other medications, etc.

VI. Providing Patient-Specific Treatment Planning

As described above in connection with step 500 shown in FIG. 2, the exemplary method may include providing patient-specific treatment planning. In an exemplary embodiment, step 500 may include the following steps. Although FIG. 3 does not show the following steps, it is understood that these steps may be performed in conjunction with the steps shown in FIG. 3, e.g., after steps 406 or 408.

As described above, the cFFR model 54 shown in FIGS. 1 and 23 indicates the cFFR values throughout the patient's anatomy represented by the mesh 380 of FIGS. 17-19 in an untreated state and under simulated hyperemia conditions. Using this information, the physician may prescribe treatments to the patient, such as an increase in exercise, a change in diet, a prescription of medication, surgery on any portion of the modeled anatomy or other portions of the heart (e.g., coronary artery bypass grafting, insertion of one or more coronary stents, etc.), etc.

To determine which treatment(s) to prescribe, the computer system may be used to predict how the information determined from the computational analysis would change based on such treatment(s). For example, certain treatments, such as insertion of stent(s) or other surgeries, may result in a change in geometry of the modeled anatomy. Accordingly, in an exemplary embodiment, the solid model 320 generated in step 306 may be revised to indicate a widening of one or more lumens where a stent is inserted.

For example, the cFFR model 54 shown in FIGS. 1 and 23 indicates that the lowest cFFR value in the LAD artery is 0.66, the lowest cFFR value in the LCX artery is 0.72, the lowest cFFR value in the RCA artery is 0.80. Treatment may be proposed if a cFFR value is, for example, less than 0.75. Accordingly, the computer system may propose to the user revising the solid model 320 to indicate a widening of the LAD artery and the LCX artery to simulate inserting stents in these coronary arteries. The user may be prompted to choose the location and amount of widening (e.g., the length and diameter) corresponding to the location and size of the simulated stent. Alternatively, the location and amount of widening may be determined automatically by the computer system based on various factors, such as the location of the node(s) with cFFR values that are less than 0.75, a location of a significant narrowing of the vessels, sizes of conventional stents, etc.

Figure 25:
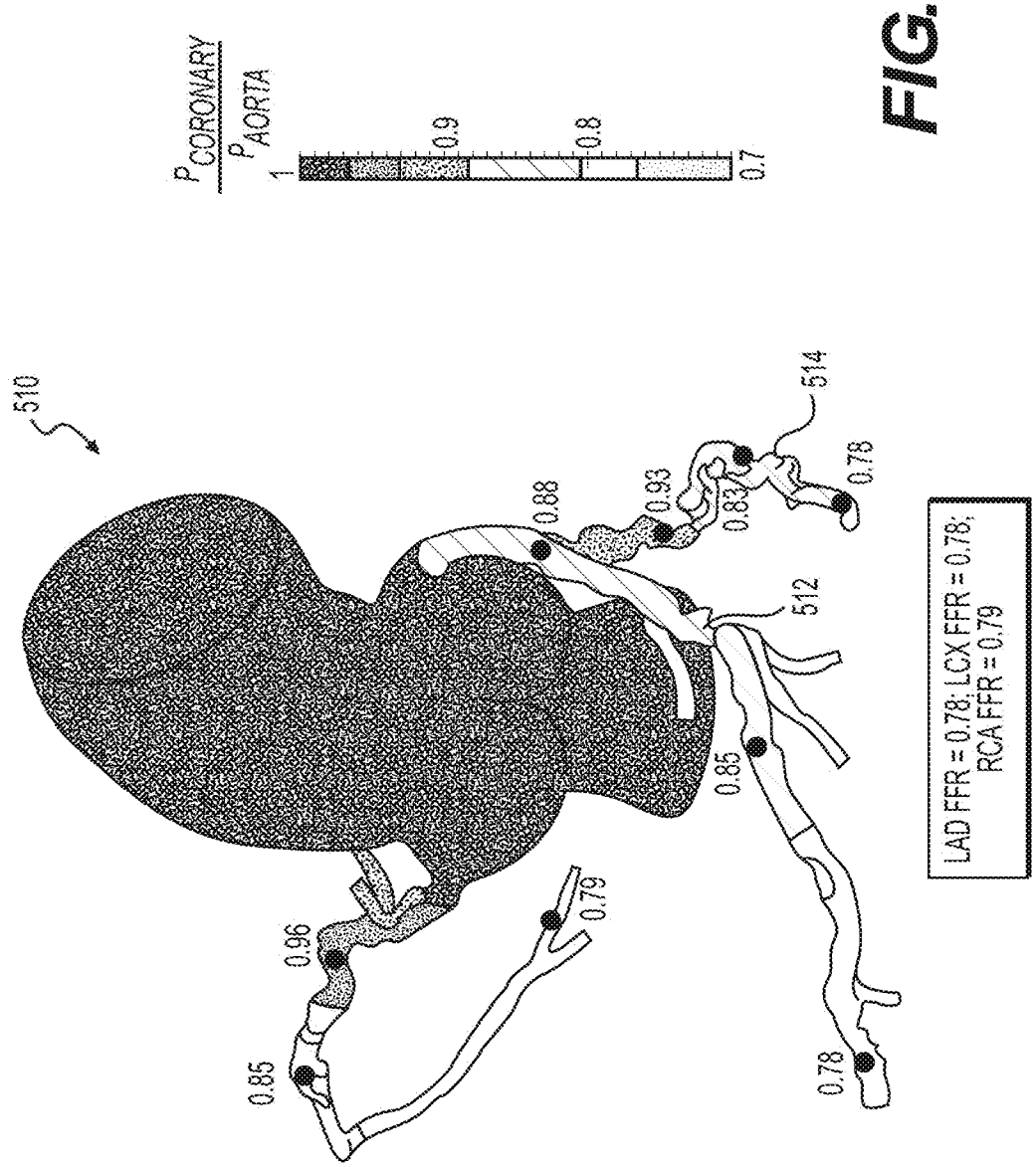
FIG. 25 shows a modified cFFR model determined based on a solid model created by widening a portion of the left anterior descending (LAD) artery and a portion of the LCX artery, according to an exemplary embodiment.

FIG. 25 shows an example of a modified cFFR model 510 determined based on a solid model created by widening a portion of the LAD artery at location 512 and a portion of the LCX artery at location 514. In an exemplary embodiment, any of the steps described above, e.g., steps 310-314 and 402-408, may be repeated using the modified solid model. In step 406, the finalized report may include the information relating to the untreated patient (e.g., without the stents), such as the information shown in FIG. 23, and information relating to the simulated treatment for the patient, such as the information shown in FIGS. 25 and 26.

FIG. 25 includes the modified cFFR model 510 and also includes summary information, such as the lowest cFFR values in the main coronary arteries and the branches that extend therefrom for the modified solid model associated with the proposed treatment. For example, FIG. 25 indicates that the lowest cFFR value in the LAD artery (and its downstream branches) is 0.78, the lowest cFFR value in the LCX artery (and its downstream branches) is 0.78, the lowest cFFR value in the RCA artery (and its downstream branches) is 0.79. Accordingly, a comparison of the cFFR model 54 of the untreated patient (without stents) and the cFFR model 510 for the proposed treatment (with stents inserted) indicates that the proposed treatment may increase the minimum cFFR in the LAD artery from 0.66 to 0.78 and would increase the minimum cFFR in the LCX artery from 0.72 to 0.76, while there would be a minimal decrease in the minimum cFFR in the RCA artery from 0.80 to 0.79.

Figure 26:
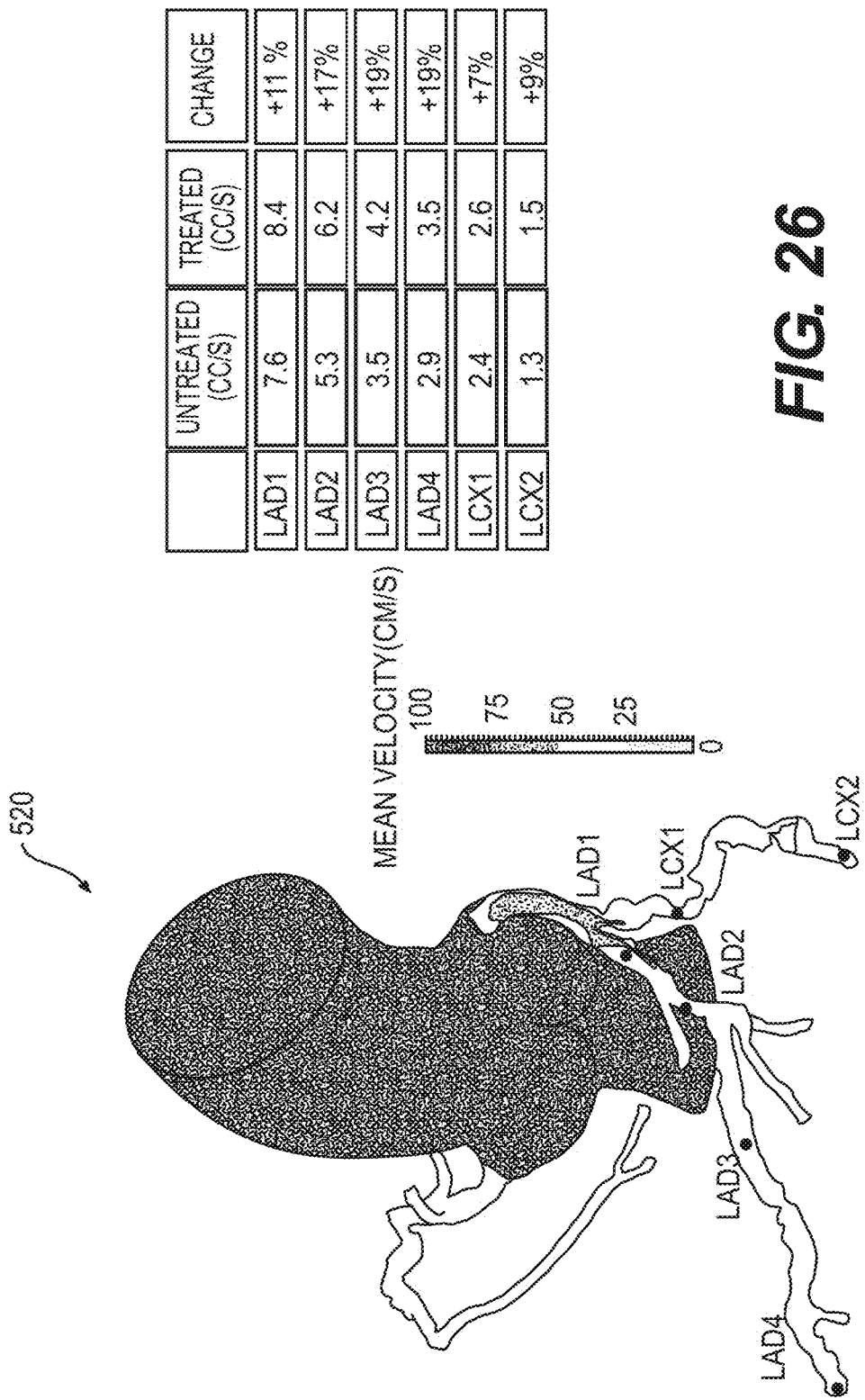
FIG. 26 shows an example of a modified simulated blood flow model after widening a portion of the LAD artery and a portion of the left circumflex (LCX) artery, according to an exemplary embodiment.

FIG. 26 shows an example of a modified simulated blood flow model 520 determined after widening portions of the LAD artery at location 512 and of the LCX artery at location 514 as described above. FIG. 26 also includes summary information, such as the blood flow values at various locations in the main coronary arteries and the branches that extend therefrom for the modified solid model associated with the proposed treatment. For example, FIG. 26 indicates blood flow values for four locations LAD1, LAD2, LAD3, and LAD4 in the LAD artery and for two locations LCX1 and LCX2 in the LCX artery for the untreated patient (without stents) and for the treated patient (with stents inserted). FIG. 26 also indicates a percentage change in blood flow values between the untreated and treated states. Accordingly, a comparison of the simulated blood flow model 52 of the untreated patient and the simulated blood flow model 520 for the proposed treatment indicates that the proposed treatment may increase the flow through the LAD artery and LCX artery at all of the locations LAD1-LAD4, LCX1, and LCX2 by 9% to 19%, depending on the location.

Other information may also be compared between the untreated and treated states, such as coronary artery blood pressure. Based on this information, the physician may discuss with the patient whether to proceed with the proposed treatment option.

Other treatment options may also involve modifying the solid model 320 in different ways. For example, coronary artery bypass grafting may involve creating new lumens or passageways in the solid model 320 and removing a lesion may also involve widening a lumen or passage. Other treatment options may not involve modifying the solid model 320. For example, an increase in exercise or exertion, a change in diet or other lifestyle change, a prescription of medication, etc., may involve changing the boundary conditions determined in step 310, e.g., due to vasoconstriction, dilation, decreased heart rate, etc. For example, the patient's heart rate, cardiac output, stroke volume, blood pressure, coronary microcirculation function, the configurations of the lumped parameter models, etc., may depend on the medication prescribed, the type and frequency of exercise adopted (or other exertion), the type of lifestyle change adopted (e.g., cessation of smoking, changes in diet, etc.), thereby affecting the boundary conditions determined in step 310 in different ways.

In an exemplary embodiment, modified boundary conditions may be determined experimentally using data from many patients, and similar treatment options may require modifying the boundary conditions in similar ways. Empirical models may be developed from a large population of patient-specific data, creating a library of boundary conditions or functions for calculating boundary conditions, corresponding to specific treatment options that may be applied to similar patients in future analyses.

After modifying the boundary conditions, the steps described above, e.g., steps 312, 314, and 402-408, may be repeated using the modified boundary conditions, and in step 406, the finalized report may include the information relating to the untreated patient, such as the information shown in FIG. 23, and information relating to the simulated treatment for the patient, such as the information shown in FIGS. 25 and 26.

Alternatively, the physician, the patient, or other user may be provided with a user interface that allows interaction with a three-dimensional model (e.g., the solid model 320 of FIG. 8). The model 320 may be divided into user-selectable segments that may be edited by the user to reflect one or more treatment options. For example, the user may select a segment with a stenosis (or occlusion, e.g., an acute occlusion) and adjust the segment to remove the stenosis, the user may add a segment to the model 320 to serve as a bypass, etc. The user may also be prompted to specify other treatment options and/or physiologic parameters that may alter the boundary conditions determined above, e.g., a change in a cardiac output, a heart rate, a stroke volume, a blood pressure, an exercise or exertion level, a hyperemia level, medications, etc. In an alternate embodiment, the computer system may determine or suggest a treatment option.

The user interface may allow interaction with the three-dimensional model 320 to allow the user to simulate a stenosis (or occlusion, e.g., an acute occlusion). For example, the user may select a segment for including the stenosis, and the computer system may be used to predict how the information determined from the computational analysis would change based on the addition of the stenosis. Thus, the methods described herein may be used to predict the effect of occluding an artery.

The user interface may also allow interaction with the three-dimensional model 320 to simulate a damaged artery or removal of an artery, which may occur, for example, in certain surgical procedures, such as when removing cancerous tumors. The model may also be modified to simulate the effect of preventing blood flow through certain arteries in order to predict the potential for collateral pathways for supplying adequate blood flow for the patient.

A. Using Reduced Order Models to Compare Different Treatment Options

Figure 27:
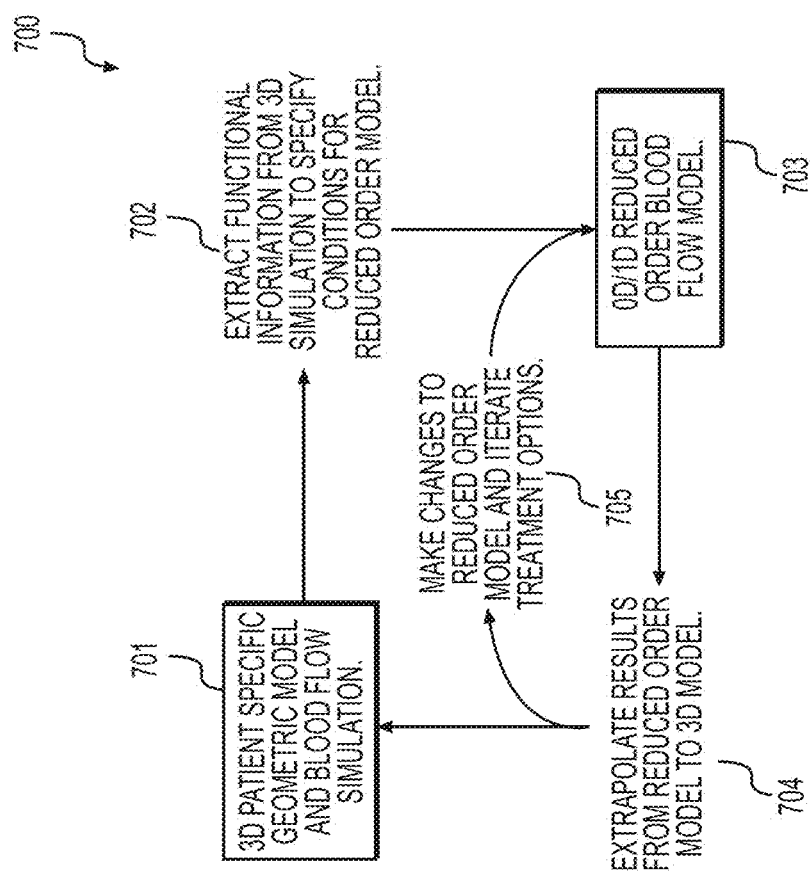
FIG. 27 is a flow chart of a method for simulating various treatment options using a reduced order model, according to an exemplary embodiment.

In an exemplary embodiment, the computer system may allow the user to simulate various treatment options more quickly by replacing the three-dimensional solid model 320 or mesh 380 with a reduced order model. FIG. 27 shows a schematic diagram relating to a method 700 for simulating various treatment options using a reduced order model, according to an exemplary embodiment. The method 700 may be implemented in the computer system described above.

One or more patient-specific simulated blood flow models representing blood flow or other parameters may be output from the computational analysis described above (step 701). For example, the simulated blood flow models may include the simulated blood pressure model 50 of FIG. 1, the simulated blood flow model 52 of FIG. 1, the cFFR model 54 of FIG. 1, etc., provided using the methods described above and shown in FIGS. 2 and 3. As described above, the simulated blood flow model may include a three-dimensional geometrical model of the patient's anatomy.

Functional information may be extracted from the simulated blood flow models in order to specify conditions for a reduced order model (step 702). For example, the functional information may include the blood pressure, flow, or velocity information determined using the computational analysis described above.

A reduced order (e.g., zero-dimensional or one-dimensional) model may be provided to replace the three-dimensional solid model 320 used to generate the patient specific simulated blood flow models generated in step 701, and the reduced order model may be used to determine information about the coronary blood flow in the patient (step 703). For example, the reduced order model may be a lumped parameter model generated as described above in connection with step 310 of FIG. 3. Thus, the lumped parameter model is a simplified model of the patient's anatomy that may be used to determine information about the coronary blood flow in the patient without having to solve the more complex system of equations associated with the mesh 380 of FIGS. 17-19.

Information determined from solving the reduced order model in step 703 may then be mapped or extrapolated to a three-dimensional solid model (e.g., the solid model 320) of the patient's anatomy (step 704), and the user may make changes to the reduced order model as desired to simulate various treatment options and/or changes to the physiologic parameters for the patient, which may be selected by the user (step 705). The selectable physiologic parameters may include cardiac output, exercise or exertion level, level of hyperemia, types of medications, etc. The selectable treatment options may include removing a stenosis, adding a bypass, etc.

Then, the reduced order model may be modified based on the treatment options and/or physiologic parameters selected by the user, and the modified reduced order model may be used to determine information about the coronary blood flow in the patient associated with the selected treatment option and/or physiologic parameter (step 703). Information determined from solving the reduced order model in step 703 may then be mapped or extrapolated to the three-dimensional solid model 320 of the patient's anatomy to predict the effects of the selected treatment option and/or physiologic parameter on the coronary blood flow in the patient's anatomy (step 704).

Steps 703-705 may be repeated for various different treatment options and/or physiologic parameters to compare the predicted effects of various treatment options to each other and to the information about the coronary blood flow in the untreated patient. As a result, predicted results for various treatment options and/or physiologic parameters may be evaluated against each other and against information about the untreated patient without having to rerun the more complex analysis using the three-dimensional mesh 380. Instead, a reduced order model may be used, which may allow the user to analyze and compare different treatment options and/or physiologic parameters more easily and quickly.

Figure 28:
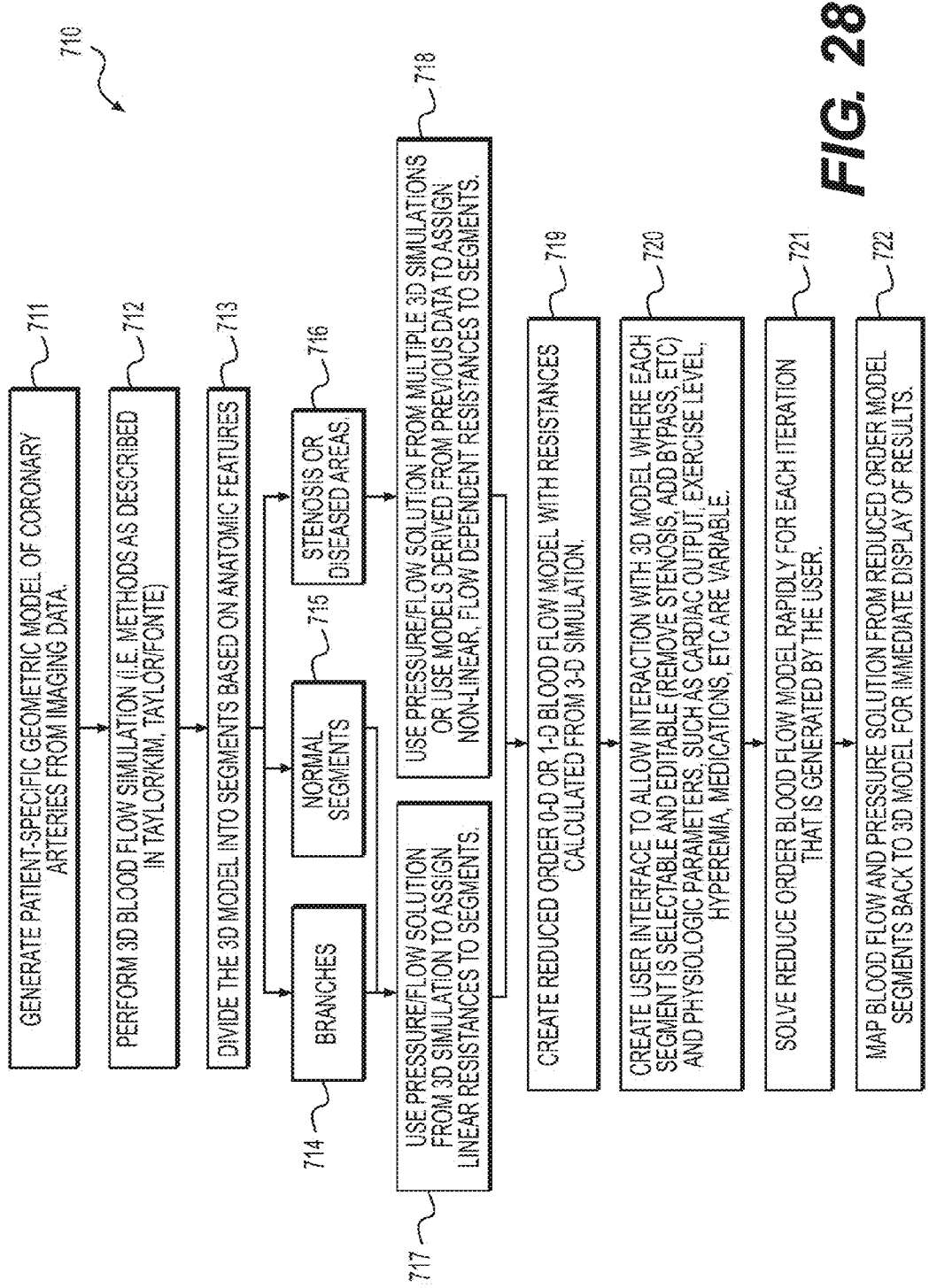
FIG. 28 is a flow chart of a method for simulating various treatment options using a reduced order model, according to another exemplary embodiment.

FIG. 28 shows further aspects of the exemplary method for simulating various treatment options using a reduced order model, according to an exemplary embodiment. The method 700 may be implemented in the computer system described above.

As described above in connection with step 306 of FIG. 3, a patient-specific geometric model may be generated based on imaging data for the patient (step 711). For example, the imaging data may include the CCTA data obtained in step 100 of FIG. 2, and the geometric model may be the solid model 320 of FIG. 8 generated in step 306 of FIG. 3, and/or the mesh 380 of FIGS. 17-19 generated in step 312 of FIG. 3.

Using the patient-specific three-dimensional geometric model, the computational analysis may be performed, e.g., as described above in connection with step 402 of FIG. 3, to determine information about the patient's coronary blood flow (step 712). The computational analysis may output one or more three-dimensional patient-specific simulated blood flow models representing blood flow or other parameters, e.g., the simulated blood pressure model 50 of FIG. 1, the simulated blood flow model 52 of FIG. 1, the cFFR model 54 of FIG. 1, etc.

The simulated blood flow model may be segmented (e.g., as described above in connection with FIG. 14) based on the anatomical features of the model (step 713). For example, branches extending from the main coronary arteries may be provided in separate segments (step 714), portions with stenosis or diseased areas may be provided in separate segments (step 716), and portions between the branches and the portions with stenosis or diseased areas may be provided in separate segments (step 715). Varying degrees of resolution may be provided in segmenting the simulated blood flow model such that each vessel may include a plurality of short, discrete segments or longer segments, e.g., including the entire vessel. Also, various techniques may be provided for segmenting the simulated blood flow model, including generating centerlines and sectioning based on the generated centerlines, or detecting branch points and sectioning based on the detected branch points. The diseased portions and stenoses may be identified, e.g., by measuring the cross-sectional area along the length of the centerline and calculating locally minimum cross-sectional areas. Steps 711-716 may be considered as substeps of step 701 of FIG. 27.

The segments may be replaced by components of a lumped parameter model, such as resistors, capacitors, inductors, etc., as described above in connection with FIG. 15. The individual values for the resistance, capacitance, inductance, and other variables associated with other electrical components used in the lumped parameter model may be derived from the simulated blood flow models provided in step 712. For example, for branches and portions between the branches and the portions with stenosis or diseased areas, information derived from the simulated blood flow model may be used to assign linear resistances to the corresponding segments (step 717). For portions with complex geometry, such as a stenosis or diseased area, resistance may vary with flow rate. Thus, multiple computational analyses may be used to obtain simulated blood flow models for various flow and pressure conditions to derive patient-specific, vessel-specific, and lesion-specific resistance functions for these complex geometries, as described above in connection with FIG. 15. Accordingly, for portions with stenosis or diseased areas, information derived from these multiple computational analyses or models derived from previous data may be used to assign non-linear, flow-dependent resistances to corresponding segments (step 718). Steps 717 and 718 may be considered as substeps of step 702 of FIG. 27.

Using the resistances determined in steps 717 and 718, a reduced order (e.g., zero-dimensional or one-dimensional) model may be generated (step 719). For example, the reduced order model may be a lumped parameter model generated as described above in connection with step 310 of FIG. 3. Thus, the lumped parameter model is a simplified model of the patient's anatomy that may be used to determine information about the coronary blood flow in the patient without having to solve the more complex system of equations associated with the mesh 380 of FIGS. 17-19.

A user interface may be provided that allows the user to interact with the reduced order model created in step 719 (step 720). For example, the user may select and edit different segments of the reduced order model to simulate different treatment options and/or may edit various physiologic parameters. For example, intervention, such as insertion of a stent to repair of a diseased region, may be modeled by decreasing the resistance of the segment where the stent is to be inserted. Forming a bypass may be modeled by adding a segment having a low resistance parallel to a diseased segment.

The modified reduced order model may be solved to determine information about the coronary blood flow in the patient under the treatment and/or change in physiologic parameters selected in step 720 (step 721). The solution values for flow and pressure in each segment determined in step 721 may then be compared to the three-dimensional solution determined in step 712, and any difference may be minimized by adjusting the resistance functions of the segments (e.g., as determined in steps 717 and 718) and resolving the reduced order model (e.g., step 721) until the solutions match. As a result, the reduced order model may be created and then solved with a simplified set of equations that allows for relatively rapid computation (e.g., compared to a full three-dimensional model) and may be used to solve for flow rate and pressure that may closely approximate the results of a full three-dimensional computational solution. The reduced order model allows for relatively rapid iterations to model various different treatment options.

Information determined from solving the reduced order model in step 721 may then be mapped or extrapolated to a three-dimensional solid model of the patient's anatomy (e.g., the solid model 320) (step 722). Steps 719-722 may be similar to steps 703-705 of FIG. 27 and may be repeated as desired by the user to simulate different combinations of treatment options and/or physiologic parameters.

Alternatively, rather than calculating the resistance along segments from the three-dimensional model (e.g., as described above for steps 717 and 718), flow and pressure at intervals along the centerline may be prescribed into a lumped parameter or one-dimensional model. The effective resistances or loss coefficients may be solved for under the constraints of the boundary conditions and prescribed flow and pressure.

Also, the flow rates and pressure gradients across individual segments may be used to compute an epicardial coronary resistance using the solution derived from the reduced-order model (e.g., as described above for step 721). The epicardial coronary resistance may be calculated as an equivalent resistance of the epicardial coronary arteries (the portions of the coronary arteries and the branches that extend therefrom included in the patient-specific model reconstructed from medical imaging data). This may have clinical significance in explaining why patients with diffuse atherosclerosis in the coronary arteries may exhibit symptoms of ischemia (restriction in blood supply). Also, the flow per unit of myocardial tissue volume (or mass) and/or the flow per unit of cardiac work under conditions of simulated pharmacologically-induced hyperemia or varying exercise intensity may be calculated using data from the reduced-order models.

As a result, the accuracy of three-dimensional blood flow modeling may be combined with the computational simplicity and relative speed inherent in one-dimensional and lumped parameter modeling technologies. Three-dimensional computational methods may be used to numerically derive patient-specific one-dimensional or lumped parameter models that embed numerically-derived empirical models for pressure losses over normal segments, stenoses, junctions, and other anatomical features. Improved diagnosis for patients with cardiovascular disease may be provided, and planning of medical, interventional, and surgical treatments may be performed faster.

Also, the accuracy of three-dimensional computational fluid dynamics technologies may be combined with the computational simplicity and performance capabilities of lumped parameter and one-dimensional models of blood flow. A three-dimensional geometric and physiologic model may be decomposed automatically into a reduced-order one-dimensional or lumped parameter model. The three-dimensional model may be used to compute the linear or nonlinear hemodynamic effects of blood flow through normal segments, stenoses, and/or branches, and to set the parameters of empirical models. The one-dimensional or lumped parameter models may more efficiently and rapidly solve for blood flow and pressure in a patient-specific model, and display the results of the lumped parameter or one-dimensional solutions.

The reduced order patient-specific anatomic and physiologic model may be used to determine the effect of different medications or lifestyle changes (e.g., cessation of smoking, changes in diet, or increased physical activity) that alters heart rate, stroke volume, blood pressure, or coronary microcirculatory function on coronary artery blood flow. Such information may be used to optimize medical therapy or avert potentially dangerous consequences of medications. The reduced order model may also be used to determine the effect on coronary artery blood flow of alternate forms and/or varying levels of physical activity or risk of exposure to potential extrinsic force, e.g., when playing football, during space flight, when scuba diving, during airplane flights, etc. Such information may be used to identify the types and level of physical activity that may be safe and efficacious for a specific patient. The reduced order model may also be used to predict a potential benefit of percutaneous coronary interventions on coronary artery blood flow in order to select the optimal interventional strategy, and/or to predict a potential benefit of coronary artery bypass grafting on coronary artery blood flow in order to select the optimal surgical strategy.

The reduced order model may also be used to illustrate potential deleterious effects of an increase in the burden of arterial disease on coronary artery blood flow and to predict, using mechanistic or phenomenological disease progression models or empirical data, when advancing disease may result in a compromise of blood flow to the heart muscle. Such information may enable the determination of a "warranty period" in which a patient observed to be initially free from hemodynamically significant disease using noninvasive imaging may not be expected to require medical, interventional, or surgical therapy, or alternatively, the rate at which progression might occur if adverse factors are continued.

The reduced order model may also be used to illustrate potential beneficial effects on coronary artery blood flow resulting from a decrease in the burden of coronary artery disease and to predict, using mechanistic or phenomenological disease progression models or empirical data, when regression of disease may result in increased blood flow through the coronary arteries to the heart muscle. Such information may be used to guide medical management programs including, but not limited to, changes in diet, increased physical activity, prescription of statins or other medications, etc.

The reduced order model may also be incorporated into an angiography system to allow for live computation of treatment options while a physician examines a patient in a cardiac catheterization lab. The model may be registered to the same orientation as the angiography display, allowing side-by-side or overlapping results of a live angiographic view of the coronary arteries with simulated blood flow solutions. The physician may plan and alter treatment plans as observations are made during procedures, allowing for relatively rapid feedback before medical decisions are made. The physician may take pressure, FFR, or blood flow measurements invasively, and the measurements may be utilized to further refine the model before predictive simulations are performed.

The reduced order model may also be incorporated into a medical imaging system or workstation. If derived from a library of previous patient-specific simulation results, then the reduced order models may be used in conjunction with geometric segmentation algorithms to relatively rapidly solve for blood flow information after completing an imaging scan.

The reduced order model may also be used to model the effectiveness of new medical therapies or the cost/benefit of treatment options on large populations of patients. A database of multiple patient-specific lumped parameter models (e.g., hundreds, thousands, or more) may provide models to solve in relatively short amounts of time. Relatively quick iteration and optimization may be provided for drug, therapy, or clinical trial simulation or design. Adapting the models to represent treatments, patient responses to drugs, or surgical interventions may allow estimates of effectiveness to be obtained without the need to perform possibly costly and potentially risky large-scale clinical trials.

VII. Other Results

A. Assessing Myocardial Perfusion

Other results may be calculated. For example, the computational analysis may provide results that quantify myocardial perfusion (blood flow through the myocardium). Quantifying myocardial perfusion may assist in identifying areas of reduced myocardial blood flow, such as due to ischemia (a restriction in a blood supply), scarring, or other heart problems.

Figure 29:
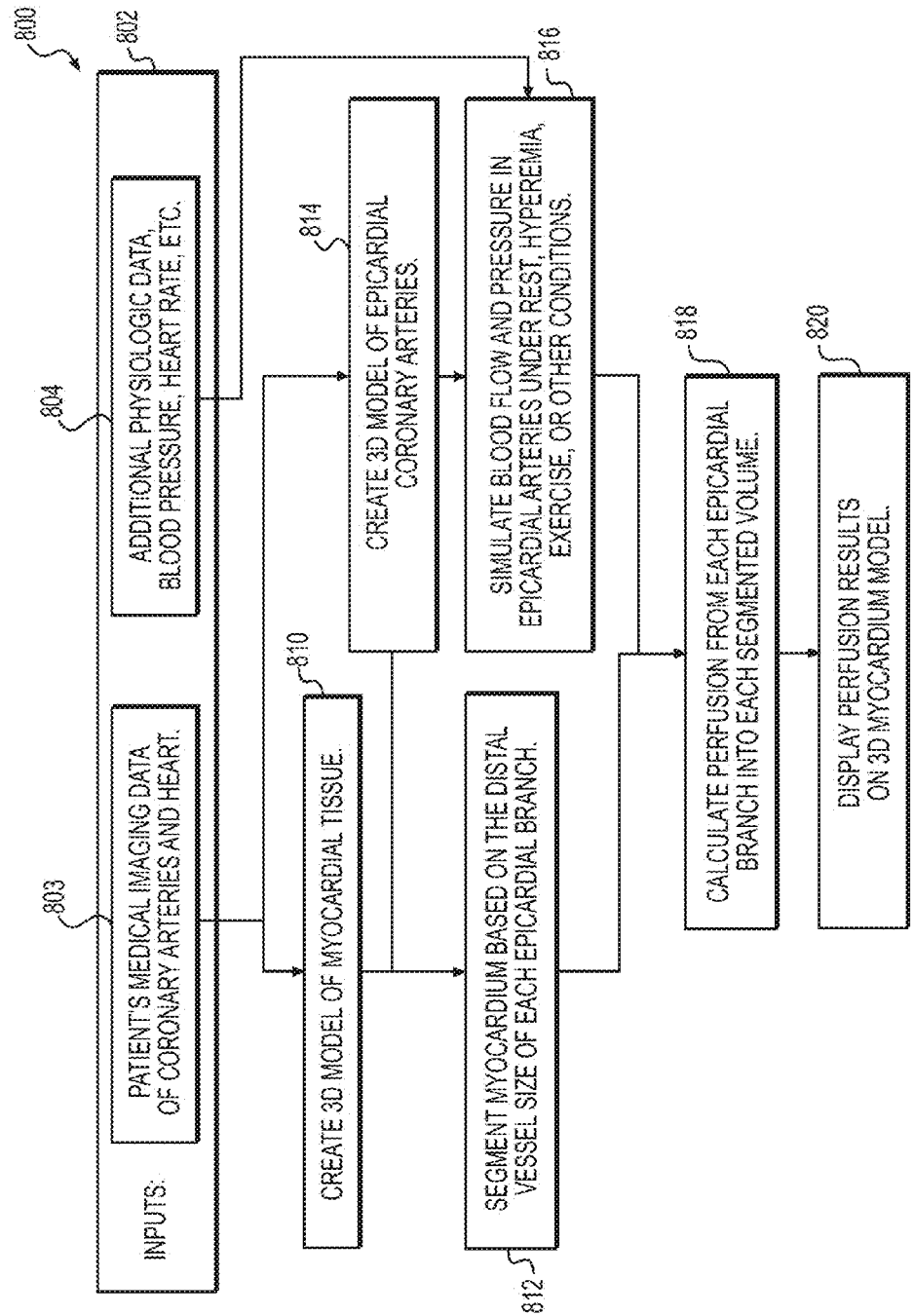
FIG. 29 is a flow chart of a method for providing various information relating to myocardial perfusion in a specific patient, according to an exemplary embodiment.

FIG. 29 shows a schematic diagram relating to a method 800 for providing various information relating to myocardial perfusion in a specific patient, according to an exemplary embodiment. The method 800 may be implemented in the computer system described above, e.g., the computer system used to implement one or more of the steps described above and shown in FIG. 3.

The method 800 may be performed using one or more inputs 802. The inputs 802 may include medical imaging data 803 of the patient's aorta, coronary arteries (and the branches that extend therefrom), and heart, such as CCTA data (e.g., obtained in step 100 of FIG. 2). The inputs 802 may also include additional physiological data 804 measured from the patient, such as the patient's brachial blood pressure, heart rate, and/or other measurements (e.g., obtained in step 100 of FIG. 2). The additional physiological data 804 may be obtained noninvasively. The inputs 802 may be used to perform the steps described below.

Figure 31:
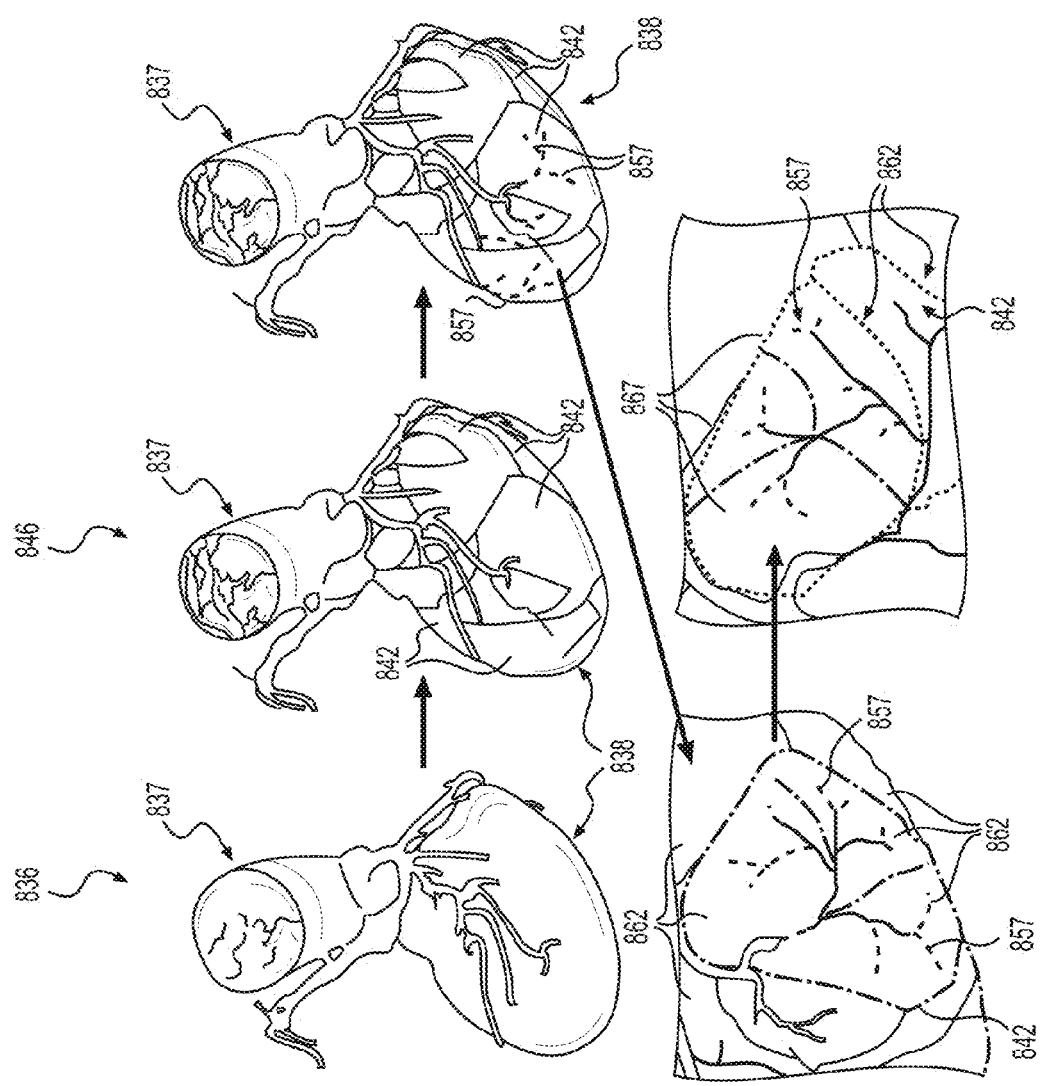
FIG. 31 shows a patient-specific model providing various information relating to myocardial perfusion, according to an exemplary embodiment.

A three-dimensional geometric model of the patient's myocardial tissue may be created based on the imaging data 803 (step 810) and the geometric model may be divided into segments or volumes (step 812). For example, FIG. 31 shows a three-dimensional geometric model 846 including a three-dimensional geometric model 838 of the patient's myocardial tissue divided into segments 842. The sizes and locations of the individual segments 842 may be determined based on the locations of the outflow boundaries 324 (FIG. 8) of the coronary arteries (and the branches extending therefrom), the sizes of the blood vessels in or connected to the respective segment 842 (e.g., the neighboring blood vessels), etc. The division of the geometric myocardial model 838 into segments 842 may be performed using various known methods, such as a fast marching method, a generalized fast marching method, a level set method, a diffusion equation, equations governing flow through a porous media, etc.

The three-dimensional geometric model may also include a portion of the patient's aorta and coronary arteries (and the branches that extend therefrom), which may be modeled based on the imaging data 803 (step 814). For example, the three-dimensional geometric model 846 of FIG. 31 includes a three-dimensional geometric model 837 of the patient's aorta and coronary arteries (and the branches that extend therefrom) and the three-dimensional geometric model 838 of the patient's myocardial tissue created in step 810.

Referring back to FIG. 29, a computational analysis may be performed, e.g., as described above in connection with step 402 of FIG. 3, to determine a solution that includes information about the patient's coronary blood flow under a physical condition determined by the user (step 816). For example, the physical condition may include rest, a selected level of hyperemia, a selected level of exercise or exertion, or other conditions. The solution may provide information, such as blood flow and pressure, at various locations in the anatomy of the patient modeled in step 814 and under the specified physical condition. The computational analysis may be performed using boundary conditions at the outflow boundaries 324 (FIG. 8) derived from lumped parameter or one-dimensional models. The one-dimensional models may be generated to fill the segments 842 as described below in connection with FIG. 30.

Based on the blood flow information determined in step 816, the perfusion of blood flow into the respective segments 842 of the myocardium created in step 812 may be calculated (step 818). For example, the perfusion may be calculated by dividing the flow from each outlet of the outflow boundaries 324 (FIG. 8) by the volume of the segmented myocardium to which the outlet perfuses.

The perfusion for the respective segments of the myocardium determined in step 818 may be displayed on the geometric model of the myocardium generated in step 810 or 812 (e.g., the three-dimensional geometric model 838 of the patient's myocardial tissue shown in FIG. 31) (step 820). For example, FIG. 31 shows that the segments 842 of the myocardium of the geometric model 838 may be illustrated with a different shade or color to indicate the perfusion of blood flow into the respective segments 842.

Figure 30:
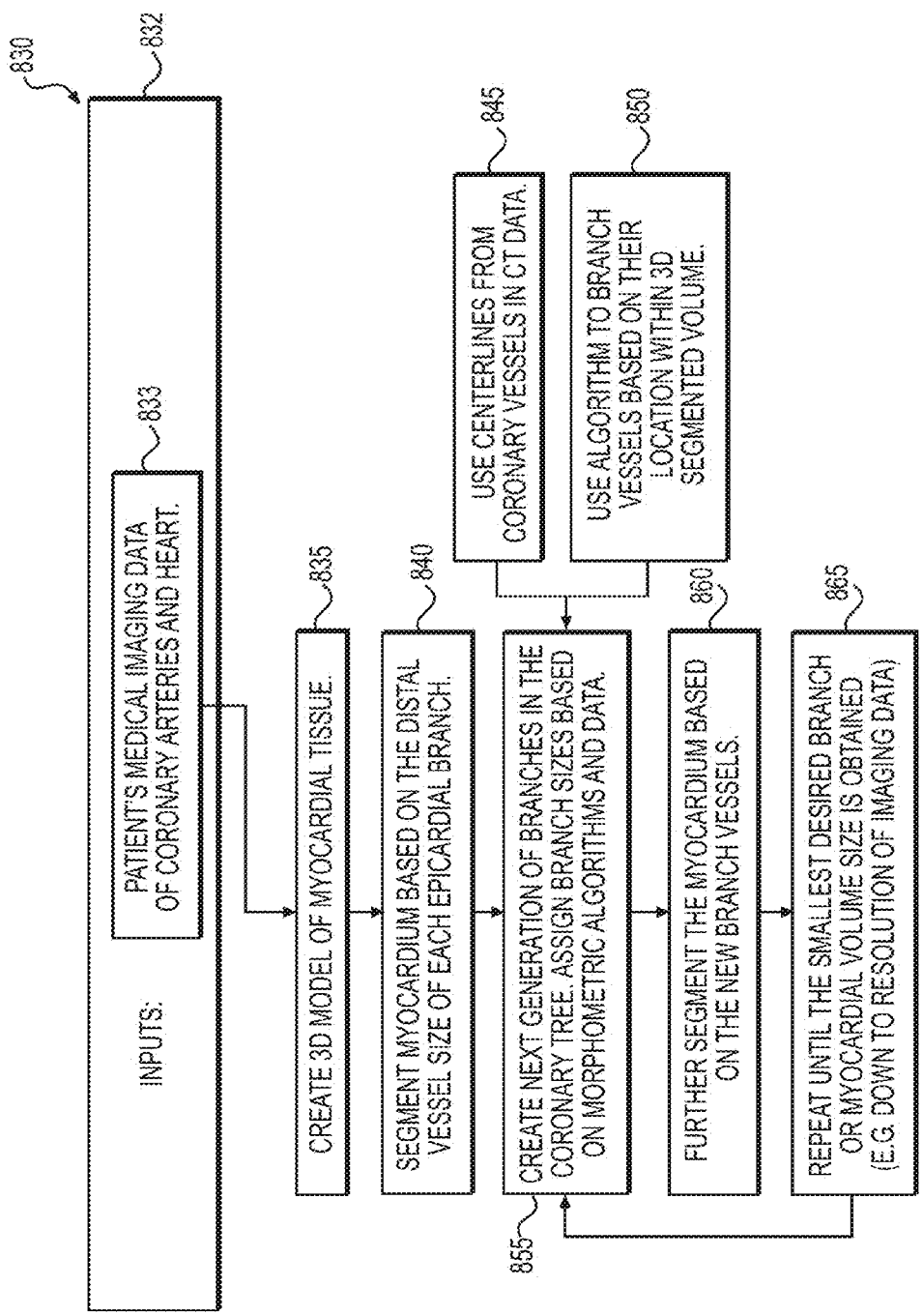
FIG. 30 is a flow chart of a method for providing various information relating to myocardial perfusion in a specific patient, according to another exemplary embodiment.

FIG. 30 shows another schematic diagram relating to a method 820 for providing various information relating to myocardial perfusion in a specific patient, according to an exemplary embodiment. The method 820 may be implemented in the computer system described above, e.g., the computer system used to implement one or more of the steps described above and shown in FIG. 3.

The method 820 may be performed using one or more inputs 832, which may include medical imaging data 833 of the patient's aorta, coronary arteries (and the branches that extend therefrom), and heart, such as CCTA data (e.g., obtained in step 100 of FIG. 2). The inputs 832 may be used to perform the steps described below.

A three-dimensional geometric model of the patient's myocardial tissue may be created based on the imaging data 833 (step 835). The model may also include a portion of the patient's aorta and coronary arteries (and the branches that extend therefrom), which may also be created based on the imaging data 803. For example, as described above, FIG. 31 shows a three-dimensional geometric model 836 including the geometric model 837 of the patient's aorta and coronary arteries (and the branches that extend therefrom) and the geometric model 838 of the patient's myocardial tissue. Step 835 may include steps 810 and 814 of FIG. 29 described above.

Referring back to FIG. 30, the geometric myocardial model 838 may be divided into volumes or segments 842 (step 840). Step 840 may include step 812 of FIG. 29 described above. As described above, FIG. 31 shows the three-dimensional geometric model 846 including the geometric model 838 of the patient's myocardial tissue divided into the segments 842.

Referring back to FIG. 30, the geometric model 846 may be modified to include a next generation of branches 857 in the coronary tree (step 855). The location and size of the branches 857 (shown in dashed lines in FIG. 31) may be determined based on centerlines for the coronary arteries (and the branches that extend therefrom). The centerlines may be determined, e.g., based on the imaging data 833 (step 845). An algorithm may also be used to determine the location and size of the branches 857 based on morphometric models (models used to predict vessel location and size downstream of the known outlets at the outflow boundaries 324 (FIG. 8)) and/or physiologic branching laws related to vessel size (step 850). The morphometric model may be augmented to the downstream ends of the coronary arteries (and the branches that extend therefrom) included in the geometric model 837, and provided on the epicardial surface (the outer layer of heart tissue) or contained within the geometric model 838 of the myocardial wall.

The myocardium may be further segmented based on the branches 857 created in step 855 (step 860). For example, FIG. 31 shows that segments 842 may be divided into subvolumes or subsegments 862.

Additional branches 857 may be created in the subsegments 862, and the subsegments 862 may be further segmented into smaller segments 867 (step 865). The steps of creating branches and sub-segmenting the volumes may be repeated until a desired resolution of volume size and/or branch size is obtained. The model 846, which has been augmented to include new branches 857 in steps 855 and 865, may then be used to compute coronary blood flow and myocardial perfusion into the subsegments, such as the subsegments 867 generated in step 865.

Accordingly, the augmented model may be used to perform the computational analysis described above. The results of the computational analysis may provide information relating to the blood flow from the patient-specific coronary artery model, e.g., the model 837 of FIG. 31, into the generated morphometric model (including the branches 857 generated in steps 855 and 865), which may extend into each of the perfusion subsegments 867 generated in step 865. The computational analysis may be performed using a static myocardial perfusion volume or a dynamic model incorporating data from coupled cardiac mechanics models.

Figure 32:
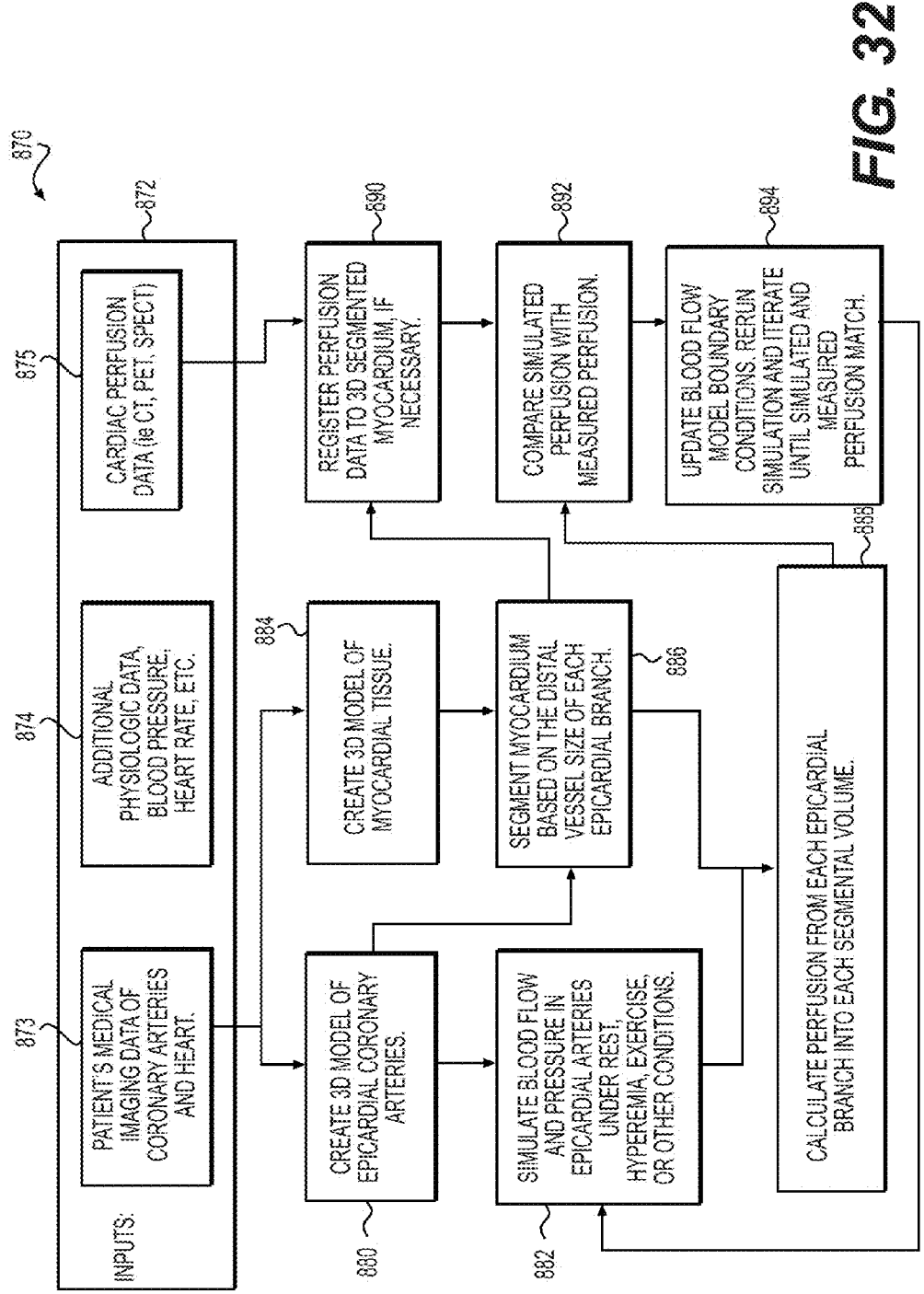
FIG. 32 is a flow chart of a method for providing various information relating to myocardial perfusion in a specific patient, according to a further exemplary embodiment.

FIG. 32 shows another schematic diagram relating to a method 870 for providing various information relating to myocardial perfusion in a specific patient, according to an exemplary embodiment. The method 870 may be implemented in the computer system described above, e.g., the computer system used to implement one or more of the steps described above and shown in FIG. 3.

The method 870 may be performed using one or more inputs 872. The inputs 872 may include medical imaging data 873 of the patient's aorta, coronary arteries (and the branches that extend therefrom), and heart, such as CCTA data (e.g., obtained in step 100 of FIG. 2). The inputs 872 may also include additional physiological data 874 measured from the patient, such as the patient's brachial blood pressure, heart rate, and/or other measurements (e.g., obtained in step 100 of FIG. 2). The additional physiological data 874 may be obtained noninvasively. The inputs 872 may further include cardiac perfusion data 875 measured from the patient (e.g., using CT, PET, SPECT, etc.). The inputs 872 may be used to perform the steps described below.

A three-dimensional geometric model of the patient's aorta and coronary arteries (and the branches that extend therefrom) may be created based on the imaging data 873 (step 880). For example, FIG. 31 shows the three-dimensional geometric model 837 of the patient's aorta and coronary arteries (and the branches that extend therefrom). Step 880 may be similar to step 814 of FIG. 29 described above.

A computational analysis may be performed, e.g., as described above in connection with step 402 of FIG. 3, to determine a solution that includes information about the patient's coronary blood flow under a physical condition determined by the user (step 882). For example, the physical condition may include rest, a selected level of hyperemia, a selected level of exercise or exertion, or other conditions. The solution may provide information, such as blood flow and pressure, at various locations in the anatomy of the patient modeled in step 880 and under the specified physical condition. Step 882 may be similar to step 816 of FIG. 29 described above.

Also, a three-dimensional geometric model of the patient's myocardial tissue may be created based on the imaging data 873 (step 884). For example, as described above, FIG. 31 shows the three-dimensional geometric model 836 including the three-dimensional geometric model 838 of the patient's myocardial tissue (e.g., as created in step 884) and the three-dimensional geometric model 837 of the patient's aorta and coronary arteries (and the branches that extend therefrom) (e.g., as created in step 880). Step 884 may be similar to step 810 of FIG. 29 described above.

The geometric model may be divided into segments or subvolumes (step 886). For example, FIG. 31 shows the geometric model 846 including the model 838 of the patient's myocardial tissue divided into segments 842. Step 886 may be similar to step 812 of FIG. 29 described above.

Based on the blood flow information determined in step 882, the perfusion of blood flow into the respective segments 842 of the myocardium created in step 886 may be calculated (step 888). Step 888 may be similar to step 818 of FIG. 29 described above.

The calculated perfusion for the respective segments of the myocardium may be displayed on the geometric model of the myocardium generated in step 884 or 886 (e.g., the three-dimensional geometric model 838 of the patient's myocardial tissue shown in FIG. 31) (step 890). For example, FIG. 31 shows that the segments 842 of the myocardium of the geometric model 838 may be illustrated with a different shade or color to indicate the perfusion of blood flow into the respective segments 842. Step 890 may be similar to step 820 of FIG. 29 described above.

The simulated perfusion data mapped onto the three-dimensional geometric model of the myocardium in step 890 may be compared with the measured cardiac perfusion data 875 (step 892). The comparison may be performed, e.g., on a voxel-based representation of the myocardium or a different discrete representation of the myocardium, e.g. a finite element mesh. The comparison may indicate the differences in the simulated and measured perfusion data using various colors and/or shades on the three-dimensional representation of the myocardium.

The boundary conditions at the outlets of the three-dimensional geometric model created in step 880 may be adjusted to decrease the error between the simulated and measured perfusion data (step 894). For example, in order to reduce the error, the boundary conditions may be adjusted so that the prescribed resistance to flow of the vessels feeding a region (e.g., the segment 842, 862, or 867) where the simulated perfusion is lower than the measured perfusion may be reduced. Other parameters of the boundary conditions may be adjusted. Alternatively, the branching structure of the model may be modified. For example, the geometric model created in step 880 may be augmented as described above in connection with FIGS. 30 and 31 to create the morphometric model. The parameters of the boundary conditions and/or morphometric models may be adjusted empirically or systematically using a parameter estimation or data assimilation method, such as the method described in U.S. Patent Application Publication No. 2010/0017171, which is entitled "Method for Tuning Patient-Specific Cardiovascular Simulations," or other methods.

Steps 882, 888, 890, 892, 894, and/or other steps of FIG. 32 may be repeated, e.g., until the error between the simulated and measured perfusion data is below a predetermined threshold. As a result, the computational analysis may be performed using a model that relates anatomical information, coronary blood flow information, and myocardial perfusion information. Such a model may be useful for diagnostic purposes and for predicting the benefits of medical, interventional, or surgical therapies.

As a result, coronary artery blood flow and myocardial perfusion under resting and/or stress conditions may be simulated in a patient-specific geometric model constructed from three-dimensional medical imaging data. Measured myocardial perfusion data may be used in combination with simulated myocardial perfusion results to adjust the boundary conditions until the simulated myocardial perfusion results match the measured myocardial perfusion data within a given tolerance (e.g., as described above in connection with FIG. 32). More accurate patient-specific coronary artery blood flow computations may be provided, and cardiologists may be enabled to predict coronary artery blood flow and myocardial perfusion under circumstances where measured data may be unavailable, such as when simulating the patient under maximum exercise or exertion, simulated treatments, or other conditions.

The patient-specific three-dimensional model of the left and/or right ventricle myocardium may be divided into perfusion segments or subvolumes. Also, a patient-specific three-dimensional geometric model of the coronary arteries determined from medical imaging data may be combined with a morphometric model of a portion of the remaining coronary arterial tree on the epicardial surface or contained in the left and/or right ventricle myocardial wall represented by the perfusion subvolumes to form an augmented model. The percentage of the total myocardial volume downstream of a given, e.g. diseased, location in the augmented model may be calculated. The percentage of the total myocardial blood flow at a given, e.g., diseased, location in the augmented model may also be calculated. The augmented model may be used to compute coronary blood flow and myocardial perfusion. The coronary blood flow model may also be modified until the simulated perfusion matches a measured perfusion data within a prescribed tolerance.

B. Assessing Plaque Vulnerability

The computational analysis may also provide results that quantify patient-specific biomechanical forces acting on plaque that may build up in the patient's aorta and coronary arteries (and the branches that extend therefrom), e.g., coronary atherosclerotic plaque. The biomechanical forces may be caused by pulsatile pressure, flow, and heart motion.

Figure 33:
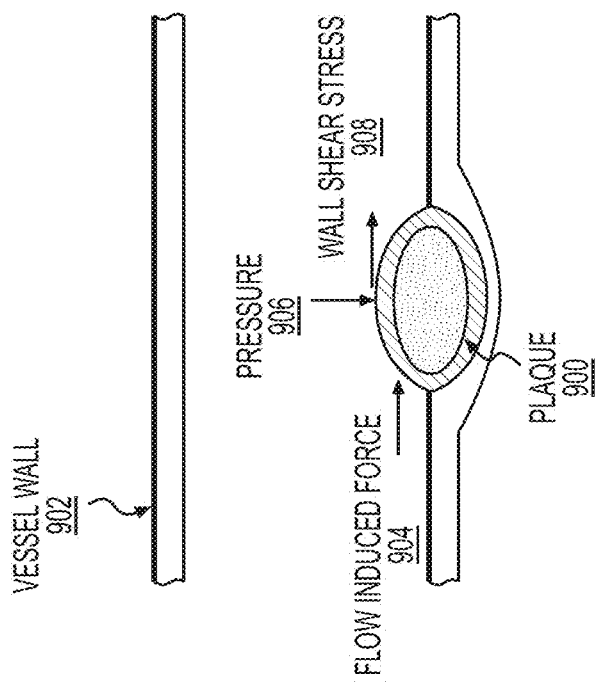
FIG. 33 is a cross-sectional view of plaque built up along a blood vessel wall.

FIG. 33 shows an example of plaque 900 built up along a blood vessel wall 902, such as a wall of one of the main coronary arteries or one of the branches that extends therefrom. The difference in pressure and/or surface area between the upstream and downstream ends of the plaque may produce a force 904 acting on the plaque 900 at least along the direction of the blood flow, e.g., caused by the blood flowing through the vessel. Another force 906 may act on a surface of the plaque 900 at least along the direction toward and perpendicular to the vessel wall 902. The force 906 may be caused by the blood pressure of the blood flowing through the vessel. Yet another force 908 may act on the surface of the plaque 900 at least along the direction of the blood flow, and may be due to hemodynamic forces during rest, exercise, etc.

The results may also assess the risk of plaque rupture (e.g., when plaque accumulated on a vessel wall becomes unstable and breaks off or breaks open) and the myocardial volume that may be affected by such rupture. The results may be assessed under various simulated physiological conditions, such as resting, exercising, etc. The plaque rupture risk may be defined as a ratio of simulated plaque stress to a plaque strength estimated using material composition data derived from CCTA or MRI (e.g., determined in step 100 of FIG. 2).

Figure 34:
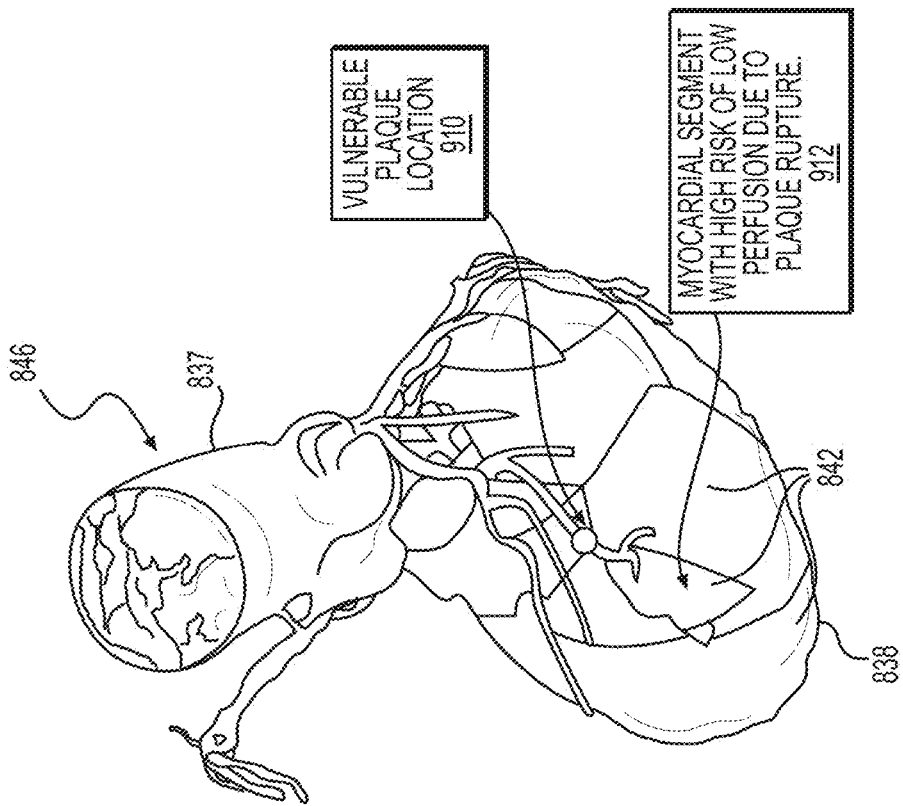
FIG. 34 shows a patient-specific model providing various information relating to plaque vulnerability, according to an exemplary embodiment.

For example, FIG. 34 shows an example of results that the computational analysis may output. The results may include the three-dimensional geometric model 846 of FIG. 31, which may include the three-dimensional geometric model 837 of the patient's aorta and coronary arteries (and the branches that extend therefrom) and the three-dimensional geometric model 838 of the patient's myocardial tissue divided into segments 842. The results may also indicate a location 910 in one of the coronary arteries (of the branches that extend therefrom) where plaque may be determined to be vulnerable, and the location 910 may be identified based on the assessment of the risk of plaque rupture as will be described below in further detail and/or based on input from a user. Also, as shown in FIG. 34, a myocardial segment 912 (of the plurality of segments 842) may be identified as having a high probability of low perfusion due to the rupture of the plaque identified at location 910.

Figure 35:
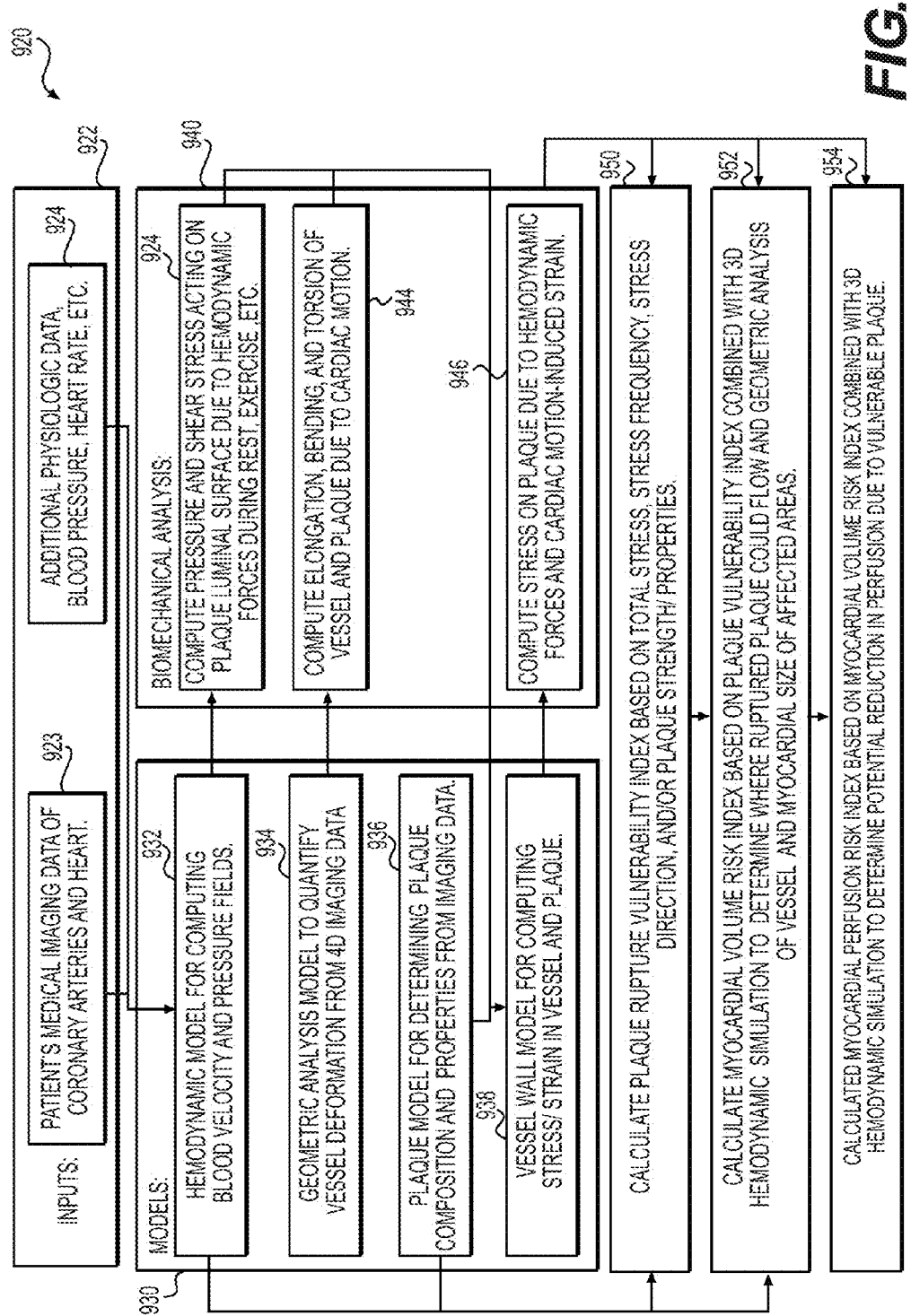
FIG. 35 is a flow chart of a method for providing various information relating to assessing plaque vulnerability, myocardial volume risk, and myocardial perfusion risk in a specific patient, according to an exemplary embodiment.
Figure 36:
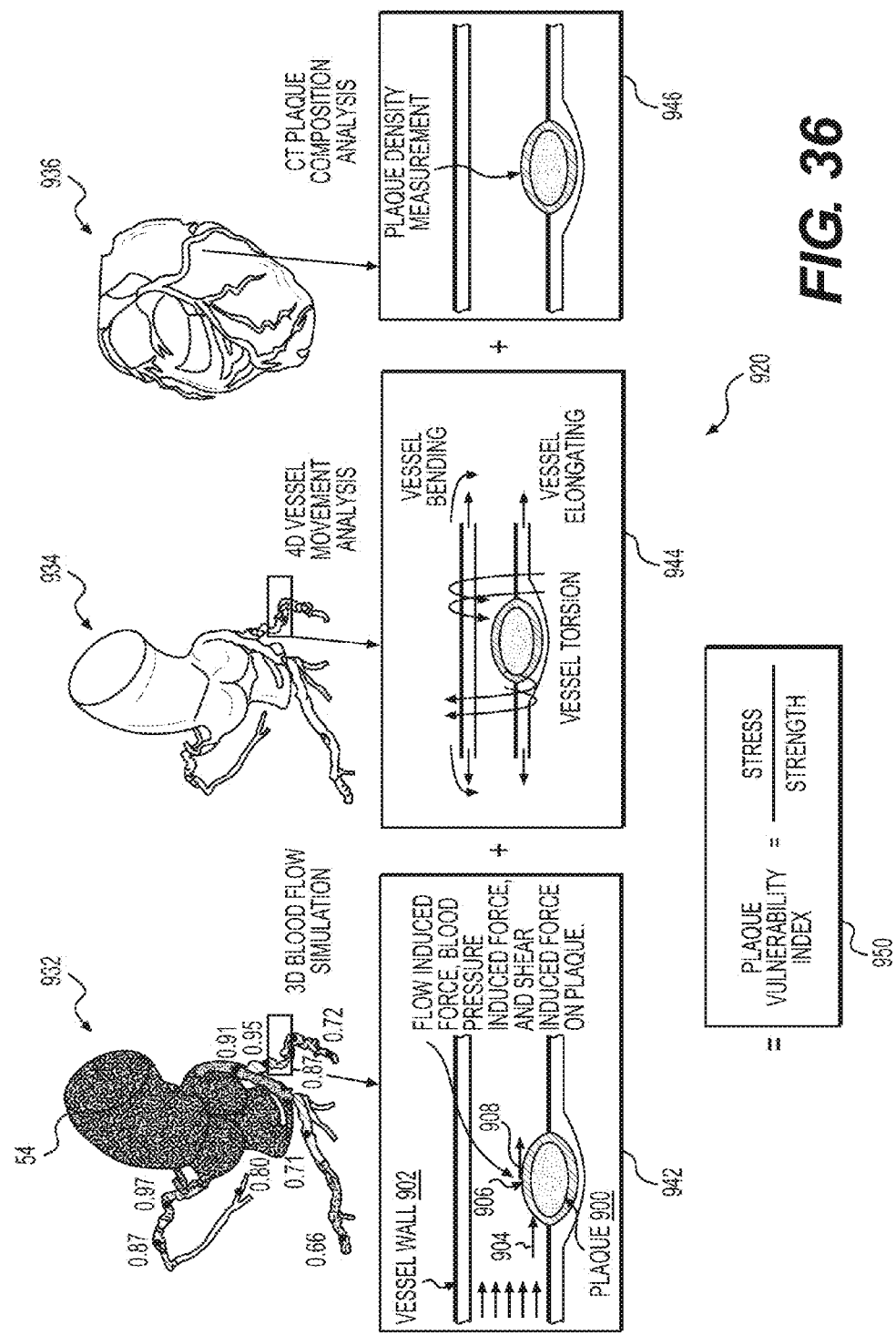
FIG. 36 is a schematic diagram showing information obtained from the method of FIG. 35, according to an exemplary embodiment.

FIGS. 35 and 36 are schematic diagrams showing aspects of a method 920 for providing various information relating to assessing plaque vulnerability, myocardial volume risk, and myocardial perfusion risk in a specific patient, according to an exemplary embodiment. The method 920 may be implemented in the computer system described above, e.g., the computer system used to implement one or more of the steps described above and shown in FIG. 3. The method 920 may be performed using one or more inputs 922, and may include generating one or more models 930 based on the inputs 922, performing one or more biomechanical analyses 940 based on the one or more of the models 930, and providing various results based on the models 930 and the biomechanical analyses 940.

The inputs 922 may include medical imaging data 923 of the patient's aorta, coronary arteries (and the branches that extend therefrom), and heart, such as CCTA data (e.g., obtained in step 100 of FIG. 2). The inputs 922 may also include additional physiological data 924 measured from the patient, such as the patient's brachial blood pressure, heart rate, and/or other measurements (e.g., obtained in step 100 of FIG. 2). The additional physiological data 924 may be obtained noninvasively. The inputs 922 may be used to generate the models 930 and/or perform the biomechanical analyses 940 described below.

As noted above, one or more models 930 may be generated based on the inputs 922. For example, the method 920 may include generating a hemodynamic model 932 including computed blood flow and pressure information at various locations throughout a three-dimensional geometric model of the patient's anatomy. The model of the patient's anatomy may be created using the medical imaging data 923, e.g., the solid model 320 of FIG. 8 generated in step 306 of FIG. 3, and/or the mesh 380 of FIGS. 17-19 generated in step 312 of FIG. 3, and, in an exemplary embodiment, the hemodynamic model 932 may be the simulated blood pressure model 50 (FIG. 1), the simulated blood flow model 52 (FIG. 1), the cFFR model 54 (FIG. 1), or other simulation produced after performing a computational analysis, e.g., as described above in connection with step 402 of FIG. 3. Solid mechanics models, including fluid structure interaction models, may be solved with the computational analysis with known numerical methods. Properties for the plaque and vessels may be modeled as linear or nonlinear, isotropic or anisotropic. The solution may provide stress and strain of the plaque and the interface between the plaque and the vessel. In the exemplary embodiment shown in FIG. 36, the hemodynamic model 932 is the cFFR model 54.

The method 920 may include performing a biomechanical analysis 940 using the hemodynamic model 932 by computing a pressure 906 (FIG. 33) and shear stress 908 (FIG. 33) acting on a plaque luminal surface due to hemodynamic forces at various physiological states, such as rest, varying levels of exercise or exertion, etc. (step 942). The pressure 906 and shear stress 908 may be calculated based on information from the hemodynamic model 932, e.g., blood pressure and flow.

Optionally, the method 920 may also include generating a geometric analysis model 934 for quantifying vessel deformation from four-dimensional imaging data, e.g., imaging data obtained at multiple phases of the cardiac cycle, such as the systolic and diastolic phases. The imaging data may be obtained using various known imaging methods. The geometric analysis model 934 may include information regarding vessel position, deformation, orientation, and size, e.g., due to cardiac motion, at the different phases of the cardiac cycle. For example, various types of deformation of the patient's aorta, coronary arteries (and the branches that extend therefrom), and the plaque, such as longitudinal lengthening (elongation) or shortening, twisting (torsion), radial expansion or compression, and bending, may be simulated by the geometric analysis model 934.

The method 920 may include performing a biomechanical analysis 940 using the geometric analysis model 934 by computing various deformation characteristics, such as longitudinal lengthening (elongation) or shortening, twisting (torsion), radial expansion or compression, and bending, etc., of the patient's aorta, coronary arteries (and the branches that extend therefrom), and the plaque due to cardiac-induced pulsatile pressure (step 944). These deformation characteristics may be calculated based on information from the geometric analysis model 934, e.g., a change in vessel position, orientation, and size, over multiple phases of the cardiac cycle.

The calculation of the deformation characteristics may be simplified by determining centerlines or surface meshes of the modeled geometry (e.g., the geometry of the patient's aorta, coronary arteries (and the branches that extend therefrom), the plaque, etc.). To determine a change in the modeled geometry between different phases, branch ostia, calcified lesions, and soft plaque may be used as landmarks. In the regions that have no landmarks, cross-sectional area profiles along a length of the modeled geometry may be used to identify corresponding locations between the two image frames (to "register" the two image frames). Deformable registration algorithms based on raw image data may be used to extract three-dimensional deformation fields. The calculated three-dimensional deformation field may then be projected to a curvilinear axis aligned with the modeled geometry (e.g., the vessel length) to compute tangential and normal components of the deformation field. The resulting difference in modeled geometry (e.g., vessel length), angle of branch separation, and curvature between systole and diastole may be used to determine the strain experienced by a vessel.

The method 920 may also include generating a plaque model 936 for determining plaque composition and properties from the medical imaging data 923. For example, the plaque model 936 may include information regarding density and other material properties of the plaque.

The method 920 may also include generating a vessel wall model 938 for computing information about the plaque, the vessel walls, and/or the interface between the plaque and the vessel walls. For example, the vessel wall model 938 may include information regarding stress and strain, which may be calculated based on the plaque composition and properties included in the plaque model 936, the pressure 906 and shear stress 908 calculated in step 942, and/or the deformation characteristics calculated in step 944.

The method 920 may include performing a biomechanical analysis 940 using the vessel wall model 938 by computing stress (e.g., acute or cumulative stress) on the plaque due to hemodynamic forces and cardiac motion-induced strain (step 946). For example, the flow-induced force 904 (FIG. 33) acting on the plaque may be computed. The stress or force on the plaque due to hemodynamic forces and cardiac motion-induced strain may be calculated based on information from the vessel wall model 938, e.g., stress and strain on the plaque.

The method 920 may include determining further information based on one or more of the models 930 and one or more of the biomechanical analyses 940 described above.

A plaque rupture vulnerability index may be calculated (step 950). The plaque rupture vulnerability index may be calculated, e.g., based on total hemodynamic stress, stress frequency, stress direction, and/or plaque strength or other properties. For example, a region surrounding a plaque of interest may be isolated from the three-dimensional model 930 of the plaque, such as the plaque model 936. The strength of the plaque may be determined from the material properties provided in the plaque model 936. A hemodynamic and tissue stress on the plaque of interest, due to pulsatile pressure, flow, and heart motion, may be calculated under simulated baseline and exercise (or exertion) conditions by using the hemodynamic stresses and motion-induced strains previously computed in step 946. The vulnerability of the plaque may be assessed based on the ratio of plaque stress to plaque strength.

A myocardial volume risk index (MVRI) may also be calculated (step 952). The MVRI may be defined as a percentage of the total myocardial volume affected by a plaque rupture and occlusion (closure or obstruction) of a vessel at a given location in the arterial tree. The MVRI may be calculated based on the portion of the myocardium supplied by the vessels downstream of the given plaque, which may take into account the size of the plaque with respect to the size of the downstream vessels and the probability that the plaque may flow into different vessels based on the three-dimensional hemodynamic solution.

The myocardium may be modeled and divided into segments 842 supplied by each vessel in the hemodynamic simulation (e.g., as described in connection with steps 835 and 840 of FIG. 30). The geometric model may be modified to include a next generation of branches 857 in the coronary tree (e.g., as described in connection with step 855 of FIG. 30), and the myocardium may be further segmented (e.g., as described in connection with step 860 of FIG. 30). Additional branches 857 may be created in the subsegments 862, and the subsegments 862 may be further segmented into smaller segments 867 (e.g., as described in connection with step 865 of FIG. 30). Physiologic relationships, as previously described, may be used to relate the size of a vessel to a proportional amount of myocardium supplied.

Potential paths for a ruptured plaque to follow may be determined. The hemodynamic solution may be used to determine a percent chance that a plaque fragment or embolus may flow into different downstream vessels.

The size of the ruptured plaque may be compared with the size of the downstream vessels to determine where the plaque may eventually create an impediment to flow. This information may be combined with the vulnerability index to provide a probability map of the volume of the myocardium that may potentially be affected by the ruptured plaque. The MVRI may be assigned to each potential affected segment. FIG. 34 shows an example of a segment 912 where the vulnerable plaque at location 910 in a distal vessel has a high probability of affecting a small area of the myocardium.

A myocardial perfusion risk index (MPRI) may also be calculated (step 954). The MPRI may be defined as a percentage of the total myocardial blood flow affected by a plaque rupture and occlusion of a vessel at a given location in the arterial tree. For example, a rupture of plaque in a distal portion of the LAD artery would yield a lower MVRI and a lower MPRI than a rupture of plaque in a proximal portion of the LAD artery. These indices may differ, however, if a portion of the myocardial volume affected by a vulnerable plaque in a feeding vessel is not viable (e.g., due to scar tissue that may form subsequent to myocardial infarction). Thus, the MPRI indicates a potential loss of perfusion to the myocardium segments, rather than the volume affected as indicated by the MVRI. The perfusion rate to each segment 842, 862, or 867 of FIG. 31 may be calculated, and the loss of perfusion may be calculated based on the vulnerability index, the hemodynamic solution, and the sizes of the plaque and vessels.

As a result, plaque stress due to pulsatile blood pressure, pulsatile blood flow, pulsatile blood shear stress, and/or pulsatile cardiac motion may be calculated, and plaque strength may be estimated based on medical imaging data, and indices relating to plaque vulnerability, myocardial volume risk, and myocardial perfusion risk may be quantified.

VIII. Other Applications

The embodiments described above are associated with assessing information about coronary blood flow in a patient. Alternatively, the embodiments may also be adapted to blood flow in other areas of the body, such as, but not limited to, the carotid, peripheral, abdominal, renal, femoral, popliteal, and cerebral arteries.

A. Modeling Intracranial and Extracranial Blood Flow

Embodiments relating to the cerebral arteries will now be described. Numerous diseases may influence or be affected by blood flow and pressure in the extracranial or intracranial arteries. Atherosclerotic disease in the extracranial, e.g. carotid and vertebral, arteries may restrict blood flow to the brain. A severe manifestation of atherosclerotic disease may lead to a transient ischemic attack or an ischemic stroke. Aneurysmal disease in the intracranial or extracranial arteries may pose a risk of embolization leading to ischemic stroke or aneurysm rupture leading to hemorrhagic stroke. Other conditions such as head trauma, hypertension, head and neck cancer, arteriovenous malformations, orthostatic intolerance, etc., may also affect cerebral blood flow. Furthermore, reductions in cerebral blood flow may induce symptoms such as syncope or impact chronic neurologic disorders such as dementia subsequent to Alzheimer's or Parkinson's disease.

Patients with known or suspected extracranial or intracranial arterial disease may typically receive one or more of the following noninvasive diagnostic tests: US, MRI, CT, PET. These tests, however, may not be able to efficiently provide anatomic and physiologic data for extracranial and intracranial arteries for most patients.

Figure 37:
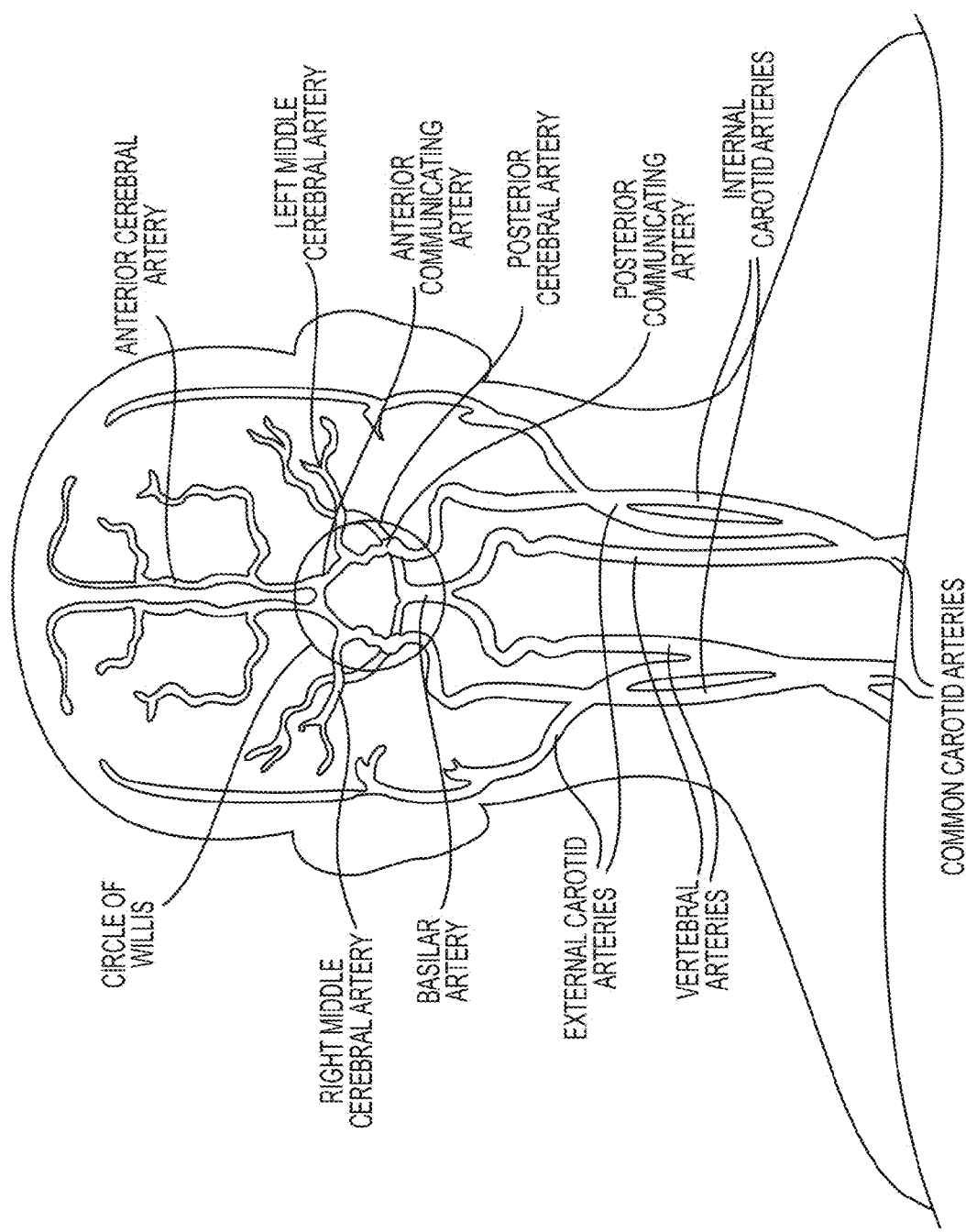
FIG. 37 is a diagram of cerebral arteries.

FIG. 37 is a diagram of cerebral arteries, including intracranial (within the cranium) and extracranial (outside the cranium) arteries. The methods for determining information regarding patient-specific intracranial and extracranial blood flow may be generally similar to the methods for determining information regarding patient-specific coronary blood flow as described above.

Figure 38:
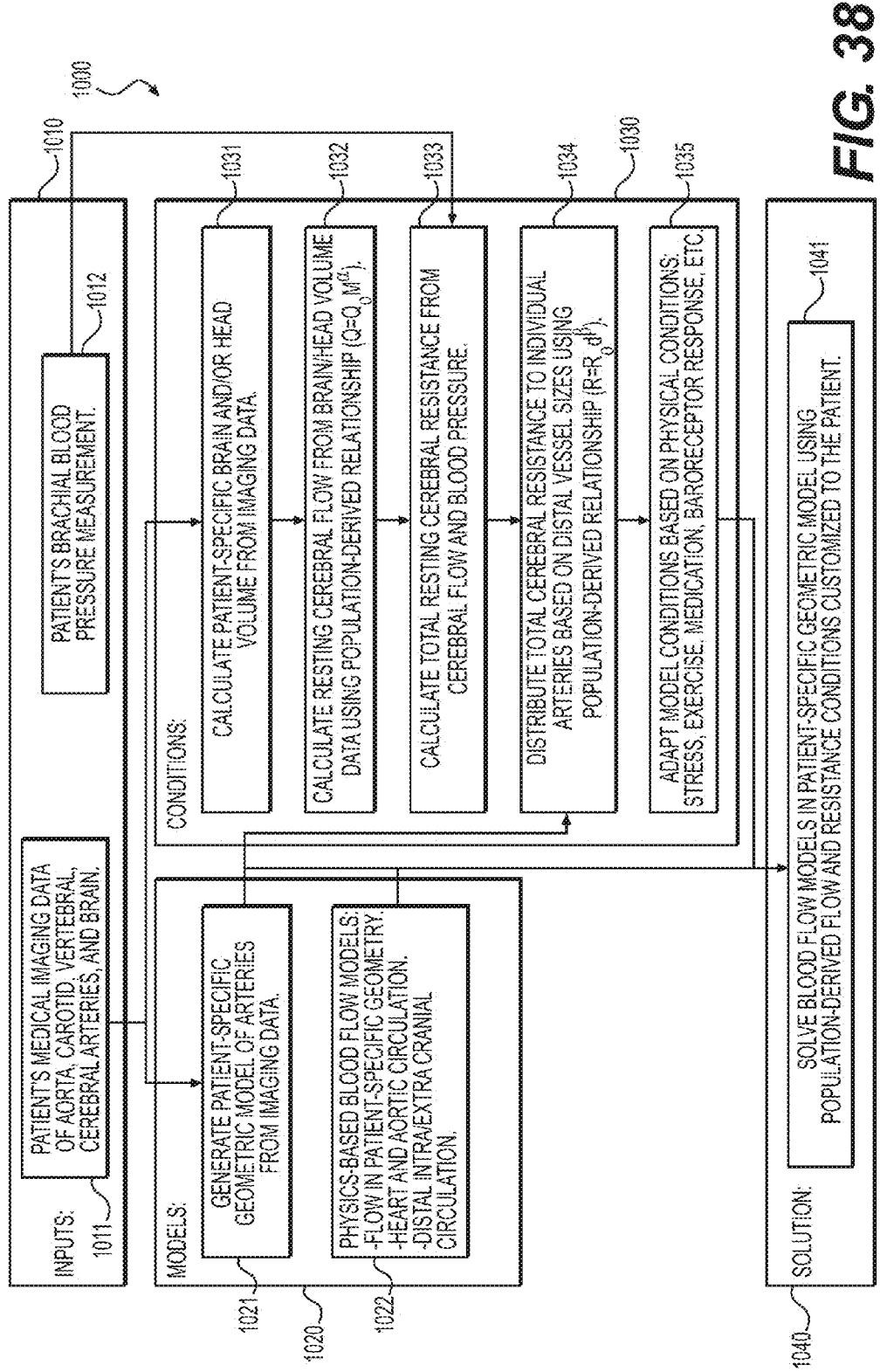
FIG. 38 is a flow chart of a method for providing various information relating to intracranial and extracranial blood flow in a specific patient, according to an exemplary embodiment.

FIG. 38 is a schematic diagram showing aspects of a method 1000 for providing various information relating to intracranial and extracranial blood flow in a specific patient. The method 1000 may be implemented in a computer system, e.g., similar to the computer system used to implement one or more of the steps described above and shown in FIG. 3. The method 1000 may be performed using one or more inputs 1010, and may include generating one or more models 1020 based on the inputs 1010, assigning one or more conditions 1030 based on the inputs 1010 and/or the models 1020, and deriving one or more solutions 1040 based on the models 1020 and the conditions 1030.

The inputs 1010 may include medical imaging data 1011 of the patient's intracranial and extracranial arteries, e.g., the patient's aorta, carotid arteries (shown in FIG. 37), vertebral arteries (shown in FIG. 37), and brain, such as CCTA data (e.g., obtained in a similar manner as described above in connection with step 100 of FIG. 2). The inputs 1010 may also include a measurement 1012 of the patient's brachial blood pressure, carotid blood pressure (e.g., using tonometry), and/or other measurements (e.g., obtained in a similar manner as described above in connection with step 100 of FIG. 2). The measurements 1012 may be obtained noninvasively. The inputs 1010 may be used to generate the model(s) 1020 and/or determine the condition(s) 1030 described below.

As noted above, one or more models 1020 may be generated based on the inputs 1010. For example, the method 1000 may include generating one or more patient-specific three-dimensional geometric models of the patient's intracranial and extracranial arteries based on the imaging data 1011 (step 1021). The three-dimensional geometric model 1021 may be generated using similar methods as described above for generating the solid model 320 of FIG. 8 and the mesh 380 of FIGS. 17-19. For example, similar steps as steps 306 and 312 of FIG. 3 may be used to generate a three-dimensional solid model and mesh representing the patient's intracranial and extracranial arteries.

Referring back to FIG. 38, the method 1000 may also include generating one or more physics-based blood flow models (step 1022). For example, the blood flow model may be a model that represents the flow through the patient-specific geometric model generated in step 1021, heart and aortic circulation, distal intracranial and extracranial circulation, etc. The blood flow model may include reduced order models as described above in connection with step 310 of FIG. 3, e.g., the lumped parameter models or distributed (one-dimensional wave propagation) models, etc., at the inflow boundaries and/or outflow boundaries of the three-dimensional geometric model 1021. Alternatively, the inflow boundaries and/or outflow boundaries may be assigned respective prescribed values or field for velocity, flow rate, pressure, or other characteristic, etc. As another alternative the inflow boundary may be coupled to a heart model, e.g., including the aortic arch. The parameters for the inflow and/or outflow boundaries may be adjusted to match measured or selected physiological conditions including, but limited to, cardiac output and blood pressure.

As noted above, one or more conditions 1030 may be determined based on the inputs 1010 and/or the models 1020. The conditions 1030 include the parameters calculated for the boundary conditions determined in step 1022 (and step 310 of FIG. 3). For example, the method 1000 may include determining a condition by calculating a patient-specific brain or head volume based on the imaging data 1011 (e.g., obtained in a similar manner as described above in connection with step 240 of FIG. 3) (step 1031).

The method 1000 may include determining a condition by calculating, using the brain or head volume calculated in step 1031, a resting cerebral blood flow Q based on the relationship $Q = Q_o M^\alpha$, where $\alpha$ is a preset scaling exponent, M is the brain mass determined from the brain or head volume, and $Q_o$ is a preset constant (e.g., similar to the physiological relationship described above in connection with determining the lumped parameter model in step 310 of FIG. 3) (step 1032). Alternatively, the relationship may have the form $Q \propto Q_o M^\alpha$, as described above in connection with determining the lumped parameter model in step 310 of FIG. 3.

The method 1000 may also include determining a condition by calculating, using the resulting coronary flow calculated in step 1032 and the patient's measured blood pressure 1012, a total resting cerebral resistance (e.g., similar to the methods described above in connection with determining the lumped parameter model in step 310 of FIG. 3) (step 1033). For example, the total cerebral blood flow Q at the outflow boundaries of the three-dimensional geometric model 1021 under baseline (resting) conditions determined in step 1032 and the measured blood pressure 1012 may be used to determine a total resistance R at the outflow boundaries based on a preset, experimentally-derived equation. Resistance, capacitance, inductance, and other variables associated with various electrical components used in lumped parameter models may be incorporated into the boundary conditions (e.g., as described above in connection with determining the lumped parameter model in step 310 of FIG. 3).

The method 1000 may also include determining a condition by calculating, using the total resting cerebral resistance calculated in step 1033 and the models 1020, individual resistances for the individual intracranial and extracranial arteries (step 1034). For example, similar to the methods described above in connection with step 310 of FIG. 3, the total resting cerebral resistance R calculated in step 1033 may be distributed to the individual intracranial and extracranial arteries based on the sizes (e.g., determined from the geometric model generated in step 1021) of the distal ends of the individual intracranial and extracranial arteries, and based on the relationship $R=R_o d^\beta$, where R is the resistance to flow at a particular distal end, and $R_o$ is a preset constant, d is the size (e.g., diameter of that distal end), and $\beta$ is a preset power law exponent, as described above in connection with determining the lumped parameter model in step 310 of FIG. 3.

Referring back to FIG. 38, the method 1000 may include adjusting the boundary conditions based on one or more physical conditions of the patient (step 1035). For example, the parameters determined in steps 1031-1034 may be modified based on whether the solution 1040 is intended to simulate rest, varying levels of stress, varying levels of baroreceptor response or other autonomic feedback control, varying levels of hyperemia, varying levels of exercise, exertion, hypertension, or hypotension, different medications, postural change, and/or other conditions. The parameters (e.g., the parameters relating to the boundary conditions at the outflow boundaries) may also be adjusted based on a vasodilatory capacity of the intracranial and extracranial arteries (the ability of the blood vessels to widen), e.g., due to microvascular dysfunction or endothelial health.

Based on the inputs 1010, the models 1020, and the conditions 1030, a computational analysis may be performed, e.g., as described above in connection with step 402 of FIG. 3, to determine the solution 1040 that includes information about the patient's coronary blood flow under the physical conditions selected in step 1035 (step 1041). Examples of information that may be provided from the solution 1040 may be similar to the examples provided above in connection with FIGS. 1 and 21-24, e.g., a simulated blood pressure model, a simulated blood flow model, etc. The results may also be used to determine, e.g., flow rate, total brain flow, vessel wall shear stress, traction or shear force acting on vessel walls or atherosclerotic plaque or aneurysm, particle/blood residence time, vessel wall movement, blood shear rate, etc. These results may also be used to analyze where emboli leaving from a specific region in the vascular system may most likely travel due to blood circulation.

The computer system may allow the user to simulate various changes in geometry. For example, the models 1020, e.g., the patient-specific geometric model generated in step 1021 may be modified to predict the effect of occluding an artery (e.g., an acute occlusion). In some surgical procedures, such as when removing cancerous tumors, one or more extracranial arteries may be damaged or removed. Thus, the patient-specific geometric model generated in step 1021 may also be modified to simulate the effect of preventing blood flow to one or more of the extracranial arteries in order to predict the potential for collateral pathways for supplying adequate blood flow for the patient.

The computer system may allow the user to simulate the results of various treatment options, such as interventional or surgical repair, e.g., of an acute occlusion. The simulations may be performed more quickly by replacing the three-dimensional solid model or mesh representing the intracranial and extracranial arteries, as described above, with reduced order models, as described above in connection with FIGS. 27 and 28. As a result, the reduced order models, such as one-dimensional or lumped parameter models, may more efficiently and rapidly solve for blood flow and pressure in a patient-specific model and display the results of solutions.

A response to vasodilatory stimuli by a specific patient may be predicted based on hemodynamic information for the patient at rest or based on population-based data for different disease states. For example, in a baseline (resting) simulation is run (e.g., as described above in step 1041) with flow distribution assigned based on power laws and brain mass (e.g., as described above in connection with step 1032). The resistance values (e.g., determined in steps 1033 and 1034) may be adjusted to allow adequate perfusion. Alternatively, data from patient populations with such factors as diabetes, medications, and past cardiac events are used to assign different resistances. The adjustment in resistance under resting conditions, alone or in combination with hemodynamic information (e.g., wall shear stress or a relationship of flow and vessel size), may be used to determine a remaining capacity for distal cerebral vessels to dilate. Patients requiring resistance reductions to meet resting flow requirements or patients with a high flow to vessel size ratio may have a diminished capacity to further dilate their vessels under physiologic stress.

Flow rates and pressure gradients across individual segments of the cerebral arteries (e.g., as determined in step 1041) may be used to compute a cerebral arterial resistance. The cerebral arterial resistance may be calculated as an equivalent resistance of the portions of the extracranial and intracranial arteries included in the patient-specific geometric model generated from medical imaging data (e.g., generated in step 1021). The cerebral arterial resistance may have clinical significance in explaining why patients with diffuse atherosclerosis in extracranial and/or intracranial arteries may exhibit symptoms of syncope (temporary loss of consciousness or posture, e.g., fainting) or ischemia (restriction in blood supply).

Also, the flow per unit of brain tissue volume (or mass) under baseline or altered physiologic conditions may be calculated, e.g., based on the flow information determined in step 1041 and the brain tissue volume or mass calculated in step 1031. This calculation may be useful in understanding the impact of reductions in blood flow on chronic neurological disorders. This calculation may also be useful in selecting or refining medical therapies, e.g., dosage of antihypertensives. Additional results may include quantifying the effects of trauma, concussion, external physiologic stresses, excess G-forces, weightlessness, space flight, deep sea decompression (e.g., the bends), etc.

The combined patient-specific anatomic (geometric) and physiologic (physics-based) model may be used to determine the effect of different medications or lifestyle changes (e.g., cessation of smoking, changes in diet, or increased physical activity) that alters heart rate, stroke volume, blood pressure, or cerebral microcirculatory function on cerebral artery blood flow. The combined model may also be used to determine the effect on cerebral artery blood flow of alternate forms and/or varying levels of physical activity or risk of exposure to potential extrinsic force, e.g., when playing football, during space flight, when scuba diving, during airplane flights, etc. Such information may be used to identify the types and level of physical activity that may be safe and efficacious for a specific patient. The combined model may also be used to predict a potential benefit of percutaneous interventions on cerebral artery blood flow in order to select the optimal interventional strategy, and/or to predict a potential benefit of carotid endarterectomy or external-carotid-to-internal-carotid bypass grafting on cerebral artery blood flow in order to select the optimal surgical strategy.

The combined model may also be used to illustrate potential deleterious effects of an increase in the burden of arterial disease on cerebral artery blood flow and to predict, using mechanistic or phenomenological disease progression models or empirical data, when advancing disease may result in a compromise of blood flow to the brain. Such information may enable the determination of a "warranty period" in which a patient observed to be initially free from hemodynamically significant disease using noninvasive imaging may not be expected to require medical, interventional, or surgical therapy, or alternatively, the rate at which progression might occur if adverse factors are continued.

The combined model may also be used to illustrate potential beneficial effects on cerebral artery blood flow resulting from a decrease in the burden of disease and to predict, using mechanistic or phenomenological disease progression models or empirical data, when regression of disease may result in increased blood flow to the brain. Such information may be used to guide medical management programs including, but not limited to, changes in diet, increased physical activity, prescription of statins or other medications, etc.

The combined model may also be used to predict the effect of occluding an artery. In some surgical procedures, such as the removal of cancerous tumors, some extracranial arteries may be damaged or removed. Simulating the effect of preventing blood flow to one of the extracranial arteries may allow prediction of the potential for collateral pathways to supply adequate blood flow for a specific patient.

i. Assessing Cerebral Perfusion

Other results may be calculated. For example, the computational analysis may provide results that quantify cerebral perfusion (blood flow through the cerebrum). Quantifying cerebral perfusion may assist in identifying areas of reduced cerebral blood flow.

Figure 39:
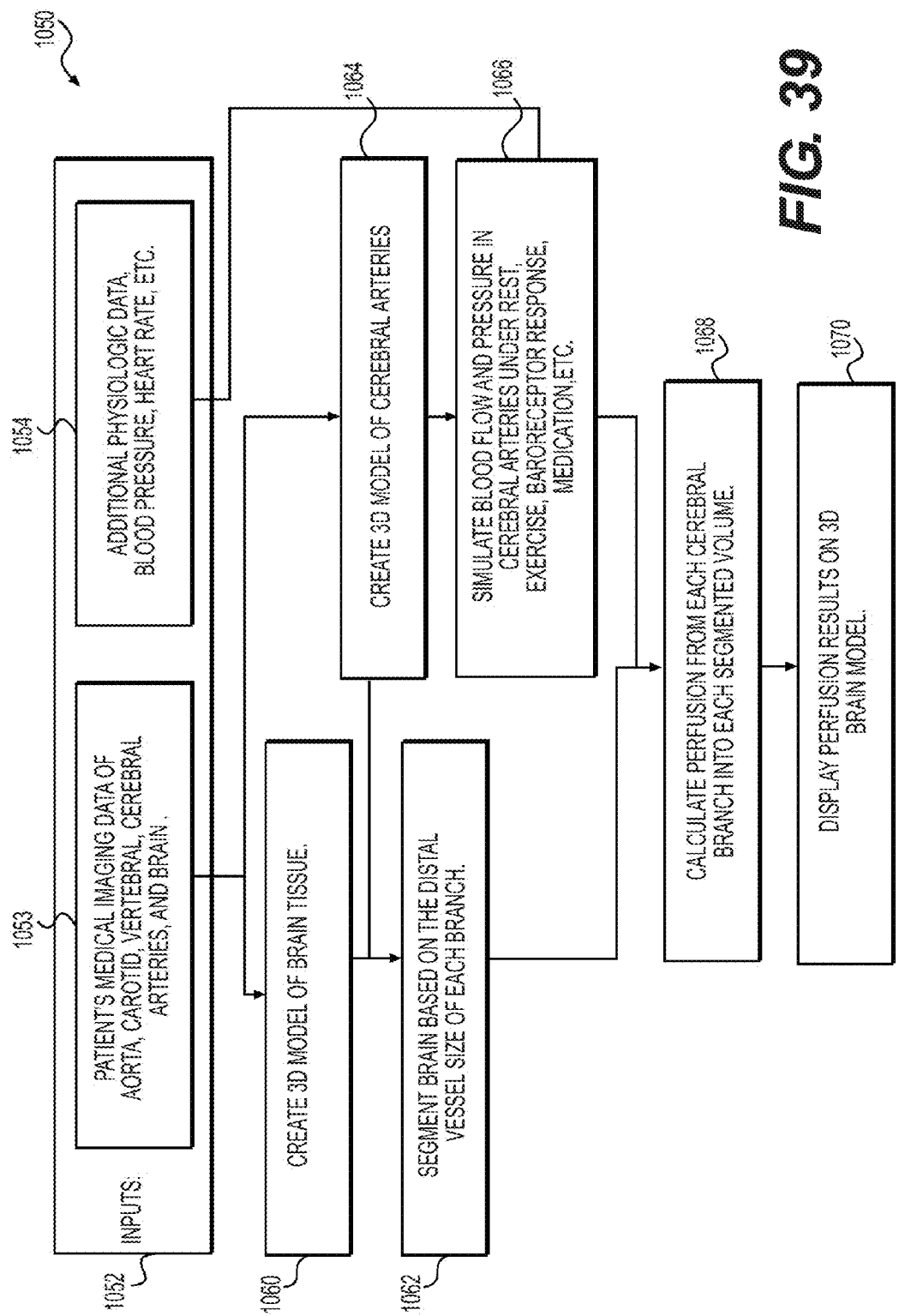
FIG. 39 is a flow chart of a method for providing various information relating to cerebral perfusion in a specific patient, according to an exemplary embodiment.

FIG. 39 shows a schematic diagram relating to a method 1050 for providing various information relating to cerebral perfusion in a specific patient, according to an exemplary embodiment. The method 1050 may be implemented in the computer system described above, e.g., similar to the computer system used to implement one or more of the steps described above and shown in FIG. 3.

The method 1050 may be performed using one or more inputs 1052. The inputs 1052 may include medical imaging data 1053 of the patient's intracranial and extracranial arteries, e.g., the patient's aorta, carotid arteries (shown in FIG. 37), vertebral arteries (shown in FIG. 37), and brain, such as CCTA data (e.g., obtained in a similar manner as described above in connection with step 100 of FIG. 2). The inputs 1052 may also include additional physiological data 1054 measured from the patient, such as the patient's brachial blood pressure, heart rate, and/or other measurements (e.g., obtained in a similar manner as described above in connection with step 100 of FIG. 2). The additional physiological data 1054 may be obtained noninvasively. The inputs 1052 may be used to perform the steps described below.

A three-dimensional geometric model of the patient's brain tissue may be created based on the imaging data 1053 (step 1060) and the geometric model may be divided into segments or volumes (step 1062) (e.g., in a similar manner as described above in connection with FIGS. 29-32). The sizes and locations of the individual segments may be determined based on the locations of the outflow boundaries of the intracranial and extracranial arteries, the sizes of the blood vessels in or connected to the respective segments (e.g., the neighboring blood vessels), etc. The division of the geometric model into segments may be performed using various known methods, such as a fast marching method, a generalized fast marching method, a level set method, a diffusion equation, equations governing flow through a porous media, etc.

The three-dimensional geometric model may also include a portion of the patient's intracranial and extracranial arteries, which may be modeled based on the imaging data 1053 (step 1064). For example, in steps 1062 and 1064, a three-dimensional geometric model may be created that includes the brain tissue and the intracranial and extracranial arteries.

A computational analysis may be performed, e.g., as described above in connection with step 402 of FIG. 3, to determine a solution that includes information about the patient's cerebral blood flow under a physical condition determined by the user (step 1066). For example, the physical condition may include rest, varying levels of stress, varying levels of baroreceptor response or other autonomic feedback control, varying levels of hyperemia, varying levels of exercise or exertion, different medications, postural change, and/or other conditions. The solution may provide information, such as blood flow and pressure, at various locations in the anatomy of the patient modeled in step 1064 and under the specified physical condition. The computational analysis may be performed using boundary conditions at the outflow boundaries derived from lumped parameter or one-dimensional models. The one-dimensional models may be generated to fill the segments of the brain tissue as described below in connection with FIG. 40.

Based on the blood flow information determined in step 1066, the perfusion of blood flow into the respective segments of the brain created in step 1062 may be calculated (step 1068). For example, the perfusion may be calculated by dividing the flow from each outlet of the outflow boundaries by the volume of the segmented brain to which the outlet perfuses.

The perfusion for the respective segments of the brain determined in step 1068 may be displayed on the geometric model of the brain generated in step 1060 or 1062 (step 1070). For example, the segments of the brain shown in the geometric model created in step 1060 may be illustrated with a different shade or color to indicate the perfusion of blood flow into the respective segments.

Figure 40:
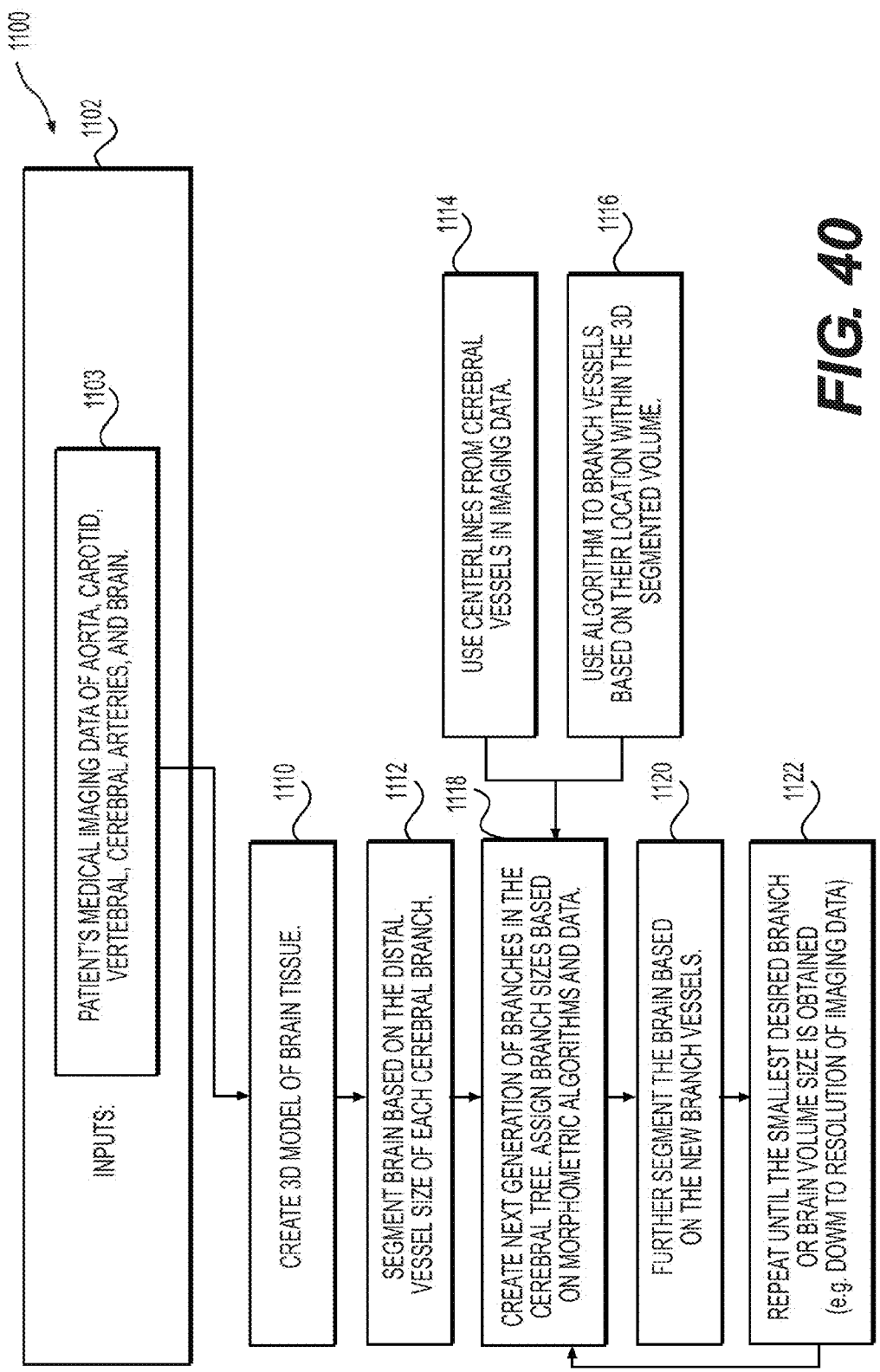
FIG. 40 is a flow chart of a method for providing various information relating to cerebral perfusion in a specific patient, according to another exemplary embodiment.

FIG. 40 shows another schematic diagram relating to a method 1100 for providing various information relating to cerebral perfusion in a specific patient, according to an exemplary embodiment. The method 1100 may be implemented in the computer system described above, e.g., similar to the computer system used to implement one or more of the steps described above and shown in FIG. 3.

The method 1100 may be performed using one or more inputs 1102, which may include medical imaging data 1103 of the patient's aorta, carotid arteries (shown in FIG. 37), vertebral arteries (shown in FIG. 37), and brain, such as CCTA data (e.g., obtained in a similar manner as described above in connection with step 100 of FIG. 2). The inputs 1102 may be used to perform the steps described below.

A three-dimensional geometric model of the patient's brain tissue may be created based on the imaging data 1103 (step 1110). The model may also include a portion of the patient's aorta, carotid arteries (shown in FIG. 37), and vertebral arteries (shown in FIG. 37), which may also be created based on the imaging data 1103. For example, as described above, a three-dimensional geometric model may be created that includes the brain tissue and the intracranial and extracranial arteries. Step 1110 may include steps 1060 and 1064 of FIG. 39 described above.

The geometric brain tissue model created in step 1110 may be divided into volumes or segments (step 1112). Step 1112 may include step 1062 of FIG. 39 described above. The geometric brain tissue model may also be further modified to include a next generation of branches in the cerebral tree (step 1118) (e.g., in a similar manner as described above in connection with FIGS. 29-32). The location and size of the branches may be determined based on centerlines for the intracranial and extracranial arteries. The centerlines may be determined, e.g., based on the imaging data 1103 (step 1114). An algorithm may also be used to determine the location and size of the branches based on morphometric models (models used to predict vessel location and size downstream of the known outlets at the outflow boundaries) and/or physiologic branching laws related to vessel size (step 1116). The morphometric model may be augmented to the downstream ends of the intracranial and extracranial arteries included in the geometric model, and provided on the outer layer of brain tissue or contained within the geometric model of the brain tissue.

The brain may be further segmented based on the branches created in step 1118 (step 1120) (e.g., in a similar manner as described above in connection with FIGS. 29-32). Additional branches may be created in the subsegments, and the subsegments may be further segmented into smaller segments (step 1122) (e.g., in a similar manner as described above in connection with FIGS. 29-32). The steps of creating branches and sub-segmenting the volumes may be repeated until a desired resolution of volume size and/or branch size is obtained. The geometric model, which has been augmented to include new branches in steps 1118 and 1122, may then be used to compute cerebral blood flow and cerebral perfusion into the subsegments, such as the subsegments generated in step 1122.

Accordingly, the augmented model may be used to perform the computational analysis described above. The results of the computational analysis may provide information relating to the blood flow from the patient-specific cerebral artery model, into the generated morphometric model (including the branches generated in steps 1118 and 1122), which may extend into each of the perfusion subsegments generated in step 1122.

Figure 41:
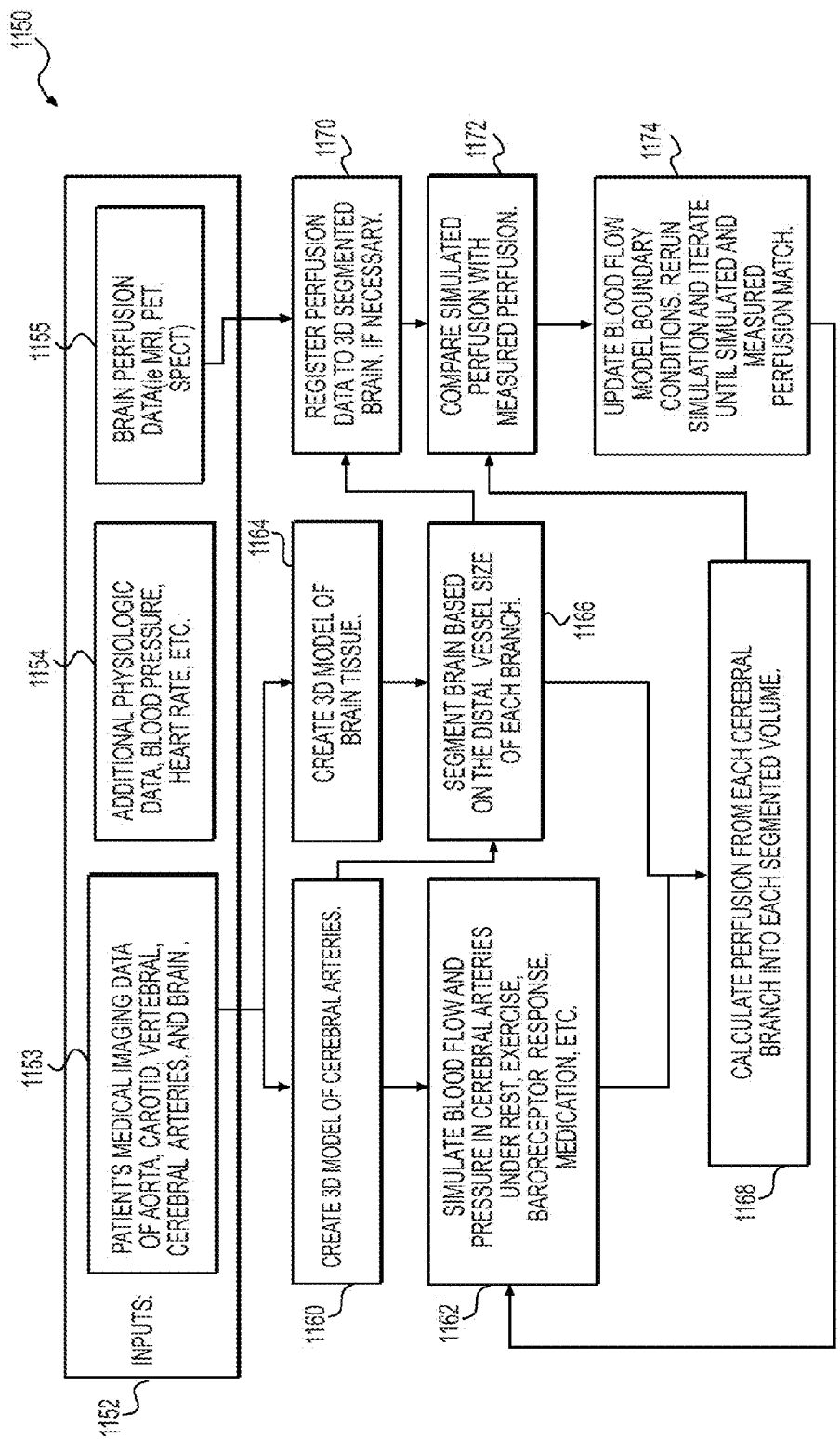
FIG. 41 is a flow chart of a method for providing various information relating to cerebral perfusion in a specific patient, according to a further exemplary embodiment.

FIG. 41 shows another schematic diagram relating to a method 1150 for providing various information relating to cerebral perfusion in a specific patient, according to an exemplary embodiment. The method 1150 may be implemented in the computer system described above, e.g., the computer system used to implement one or more of the steps described above and shown in FIG. 3.

The method 1150 may be performed using one or more inputs 1152. The inputs 1152 may include medical imaging data 1153 of the patient's aorta, carotid arteries (shown in FIG. 37), vertebral arteries (shown in FIG. 37), and brain, such as CCTA data (e.g., obtained in a similar manner as described above in connection with step 100 of FIG. 2). The inputs 1152 may also include additional physiological data 1154 measured from the patient, such as the patient's brachial blood pressure, heart rate, and/or other measurements (e.g., obtained in step 100 of FIG. 2). The additional physiological data 1154 may be obtained noninvasively. The inputs 1152 may further include brain perfusion data 1155 measured from the patient (e.g., using CT, PET, SPECT, MRI, etc.). The inputs 1152 may be used to perform the steps described below.

A three-dimensional geometric model of the patient's intracranial and extracranial arteries may be created based on the imaging data 1153 (step 1160). Step 1160 may be similar to step 1064 of FIG. 39 described above.

A computational analysis may be performed, e.g., as described above in connection with step 402 of FIG. 3, to determine a solution that includes information about the patient's cerebral blood flow under a physical condition determined by the user (step 1162). For example, the physical condition may include rest, varying levels of stress, varying levels of baroreceptor response or other autonomic feedback control, varying levels of hyperemia, varying levels of exercise or exertion, different medications, postural change, and/or other conditions. The solution may provide information, such as blood flow and pressure, at various locations in the anatomy of the patient modeled in step 1160 and under the specified physical condition. Step 1162 may be similar to step 1066 of FIG. 39 described above.

Also, a three-dimensional geometric model of the patient's brain tissue may be created based on the imaging data 1153 (step 1164). For example, in steps 1160 and 1164, a three-dimensional geometric model may be created that includes the brain tissue and the intracranial and extracranial arteries. Step 1164 may be similar to step 1060 of FIG. 39 described above.

The geometric model may be divided into segments or subvolumes (step 1166). Step 1166 may be similar to step 1062 of FIG. 39 described above.

Based on the blood flow information determined in step 1162, the perfusion of blood flow into the respective segments of the brain tissue created in step 1166 may be calculated (step 1168). Step 1168 may be similar to step 1068 of FIG. 39 described above.

The calculated perfusion for the respective segments of the brain tissue may be displayed on the geometric model of the brain tissue generated in step 1164 or 1166 (step 1170). Step 1170 may be similar to step 1070 of FIG. 39 described above.

The simulated perfusion data mapped onto the three-dimensional geometric model of the brain tissue in step 1170 may be compared with the measured cerebral perfusion data 1155 (step 1172). The comparison may indicate the differences in the simulated and measured perfusion data using various colors and/or shades on the three-dimensional representation of the brain tissue.

The boundary conditions at the outlets of the three-dimensional geometric model created in step 1160 may be adjusted to decrease the error between the simulated and measured perfusion data (step 1174). For example, in order to reduce the error, the boundary conditions may be adjusted so that the prescribed resistance to flow of the vessels feeding a region (e.g., the segments created in step 1166) where the simulated perfusion is lower than the measured perfusion may be reduced. Other parameters of the boundary conditions may be adjusted. Alternatively, the branching structure of the model may be modified. For example, the geometric model created in step 1160 may be augmented as described above in connection with FIG. 40 to create the morphometric model. The parameters of the boundary conditions and/or morphometric models may be adjusted empirically or systematically using a parameter estimation or data assimilation method, such as the method described in U.S. Patent Application Publication No. 2010/0017171, which is entitled "Method for Tuning Patient-Specific Cardiovascular Simulations," or other methods.

Steps 1162, 1168, 1170, 1172, 1174, and/or other steps of FIG. 41 may be repeated, e.g., until the error between the simulated and measured perfusion data is below a predetermined threshold. As a result, the computational analysis may be performed using a model that relates anatomical information, cerebral blood flow information, and cerebral perfusion information. Such a model may be useful for diagnostic purposes and for predicting the benefits of medical, interventional, or surgical therapies.

As a result, extracranial and intracranial arterial blood flow and cerebral perfusion under baseline conditions or altered physiologic states may be computed. Cerebral perfusion data may be used in combination with simulated cerebral perfusion results to adjust the boundary conditions of the intracranial artery blood flow computations until the simulated cerebral perfusion results match the measured cerebral perfusion data within a given tolerance. Thus, more accurate patient-specific extracranial and intracranial arterial blood flow computations may be provided and physicians may predict cerebral artery blood flow and cerebral perfusion when measured data may be unavailable, e.g., certain physical conditions such as exercise, exertion, postural changes, or simulated treatments. The patient-specific three-dimensional model of the brain may be divided into perfusion segments or subvolumes, and it may be determined whether a patient is receiving adequate minimum perfusion to various regions of the brain.

A patient-specific three-dimensional geometric model of the intracranial arteries may be generated from medical imaging data and combined with a morphometric model of a portion of the remaining intracranial arterial tree represented by perfusion segments or subvolumes (e.g., as described above in connection with FIG. 40) to form an augmented model. The percentage of the total brain volume (or mass) downstream of a given, e.g. diseased, location in the augmented model may be calculated. Also, the percentage of the total cerebral blood flow at a given, e.g. diseased, location in the augmented model may be calculated. In addition, deficits noted in functional imaging studies (e.g., functional magnetic resonance imaging (fMRI)), perfusion CT or MRI, may then be traced to disease in the feeding vessels, anatomic variants, impaired autoregulatory mechanisms, hypotension, or other conditions, which may be useful for patients with ischemic stroke, syncope, orthostatic intolerance, trauma, or chronic neurologic disorders.

ii. Assessing Plaque Vulnerability

The computational analysis may also provide results that quantify patient-specific biomechanical forces acting on plaque that may build up in the patient's intracranial and extracranial arteries, e.g., carotid atherosclerotic plaque. The biomechanical forces may be caused by pulsatile pressure, flow, and neck motion.

Figure 42:
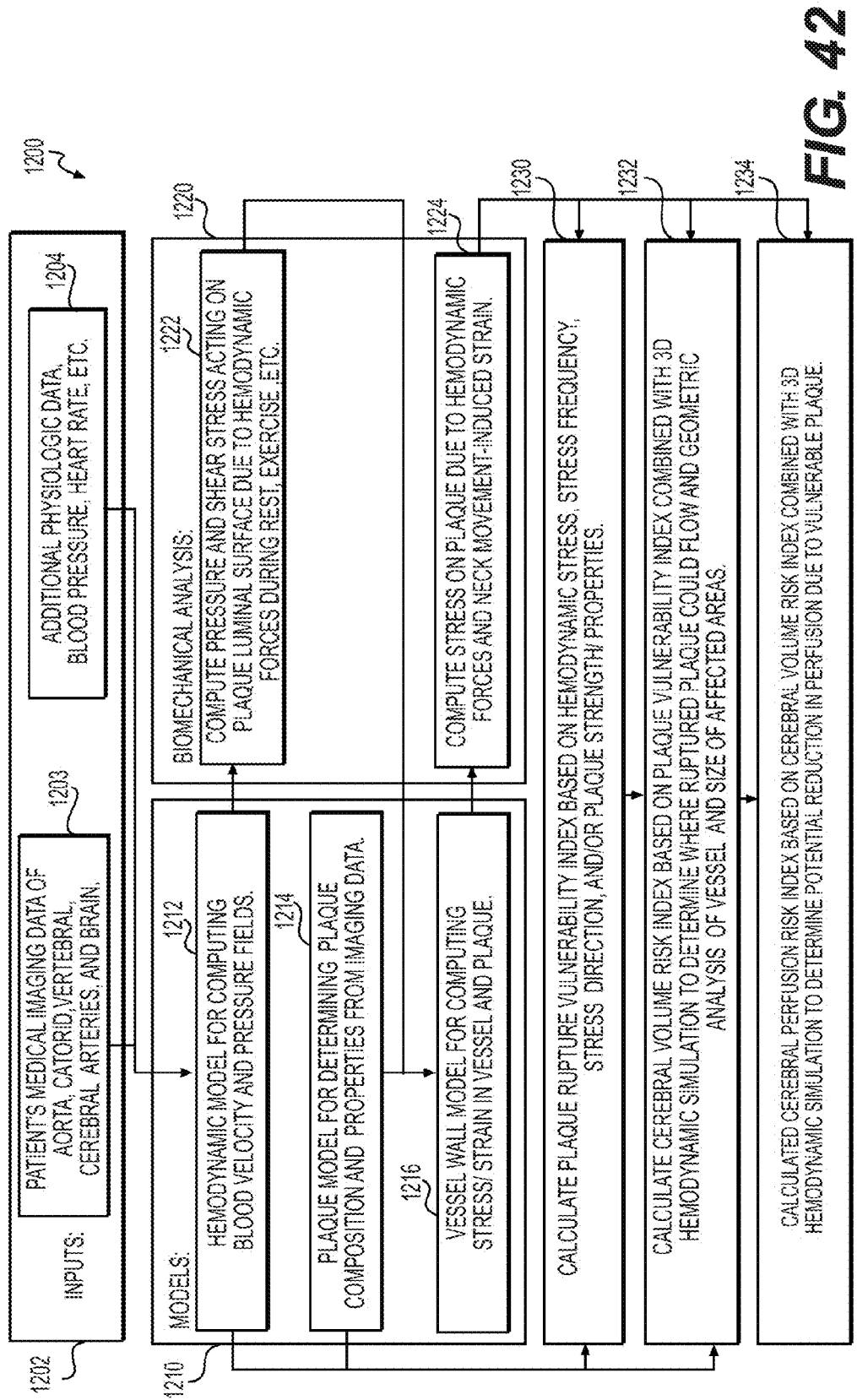
FIG. 42 is a flow chart of a method for providing various information relating to assessing plaque vulnerability, cerebral volume risk, and cerebral perfusion risk in a specific patient, according to an exemplary embodiment.

FIG. 42 is a schematic diagram showing aspects of a method 1200 for providing various information relating to assessing plaque vulnerability, cerebral volume risk, and cerebral perfusion risk in a specific patient, according to an exemplary embodiment. The method 1200 may be implemented in the computer system described above, e.g., similar to the computer system used to implement one or more of the steps described above and shown in FIG. 3. The method 1200 may be performed using one or more inputs 1202, and may include generating one or more models 1210 based on the inputs 1202, performing one or more biomechanical analyses 1220 based on the one or more of the models 1210, and providing various results based on the models 1210 and the biomechanical analyses 1220.

The inputs 1202 may include medical imaging data 1203 of the patient's intracranial and extracranial arteries, e.g., the patient's aorta, carotid arteries (shown in FIG. 37), vertebral arteries (shown in FIG. 37), and brain, such as CCTA data (e.g., obtained in a similar manner as described above in connection with step 100 of FIG. 2). The inputs 1202 may also include additional physiological data 1204 measured from the patient, such as the patient's brachial blood pressure, heart rate, and/or other measurements (e.g., obtained in a similar manner as described above in connection with step 100 of FIG. 2). The additional physiological data 1204 may be obtained noninvasively. The inputs 1202 may be used to generate the models 1210 and/or perform the biomechanical analyses 1220 described below.

As noted above, one or more models 1210 may be generated based on the inputs 1202. For example, the method 1200 may include generating a hemodynamic model 1212 including computed blood flow and pressure information at various locations throughout a three-dimensional geometric model of the patient's anatomy. The model of the patient's anatomy may be created using the medical imaging data 1203, and, in an exemplary embodiment, the hemodynamic model 1212 may be a simulated blood pressure model, the simulated blood flow model, or other simulation produced after performing a computational analysis, e.g., as described above in connection with step 402 of FIG. 3. Solid mechanics models, including fluid structure interaction models, may be solved with the computational analysis with known numerical methods. Properties for the plaque and vessels may be modeled as linear or nonlinear, isotropic or anisotropic. The solution may provide stress and strain of the plaque and the interface between the plaque and the vessel. The steps for generating the hemodynamic model 1212 may be similar to the steps for generating the hemodynamic model 932 of FIG. 35 described above.

The method 1200 may include performing a biomechanical analysis 1220 using the hemodynamic model 1212 by computing a pressure and shear stress acting on a plaque luminal surface due to hemodynamic forces at various physiological states, such as rest, varying levels of exercise or exertion, etc. (step 1222). The pressure and shear stress may be calculated based on information from the hemodynamic model 1212, e.g., blood pressure and flow. Step 1222 may be similar to step 942 of FIG. 35 described above.

Optionally, the method 1200 may also include generating a geometric analysis model for quantifying vessel deformation from four-dimensional imaging data, e.g., imaging data obtained at multiple phases of the cardiac cycle, such as the systolic and diastolic phases, in a similar manner as described above for the geometric analysis model 934 of FIG. 35. The method 1200 may also include performing a biomechanical analysis 1220 using the geometric analysis model by computing various deformation characteristics, such as longitudinal lengthening (elongation) or shortening, twisting (torsion), radial expansion or compression, and bending, etc., of the patient's intracranial and extracranial arteries and the plaque due to cardiac-induced pulsatile pressure, in a similar manner as described above for step 944 of FIG. 35.

The method 1200 may also include generating a plaque model 1214 for determining plaque composition and properties from the medical imaging data 1203. For example, the plaque model 1214 may include information regarding density and other material properties of the plaque.

The method 1200 may also include generating a vessel wall model 1216 for computing information about the plaque, the vessel walls, and/or the interface between the plaque and the vessel walls. For example, the vessel wall model 1216 may include information regarding stress and strain, which may be calculated based on the plaque composition and properties included in the plaque model 1214 and the pressure and shear stress calculated in step 1220. Optionally, stress and strain may also be calculated using calculated deformation characteristics, as described above. The steps for generating the plaque model 1214 and/or the vessel wall model 1216 may be similar to the steps for generating the plaque model 936 and/or the vessel wall model 938 of FIG. 35 described above.

The method 1200 may include performing a biomechanical analysis 1220 using the vessel wall model 1216 by computing stress (e.g., acute or cumulative stress) on the plaque due to hemodynamic forces and neck movement-induced strain (step 1224). For example, the flow-induced force 904 (FIG. 33) acting on the plaque may be computed. The stress or force on the plaque due to hemodynamic forces and neck movement-induced strain may be calculated based on information from the vessel wall model 1216, e.g., stress and strain on the plaque. Step 1224 may be similar to step 946 of FIG. 35 described above.

The method 1200 may include determining further information based on one or more of the models 1210 and one or more of the biomechanical analyses 1220 described above.

A plaque rupture vulnerability index may be calculated (step 1230). The plaque rupture vulnerability index may be calculated, e.g., based on hemodynamic stress, stress frequency, stress direction, and/or plaque strength or other properties. For example, a region surrounding a plaque of interest may be isolated from the three-dimensional model 1210 of the plaque, such as the plaque model 1214. The strength of the plaque may be determined from the material properties provided in the plaque model 1214. A hemodynamic and tissue stress on the plaque of interest, due to pulsatile pressure, flow, and neck motion, may be calculated under simulated baseline and exercise (or exertion) conditions by using the hemodynamic stresses and motion-induced strains previously computed in step 1224. The vulnerability of the plaque may be assessed based on the ratio of plaque stress to plaque strength. Step 1230 may be similar to step 950 of FIG. 35 described above. For example, the plaque rupture vulnerability index may be calculated for a plaque located in an extracranial artery for stroke assessment.

A cerebral volume risk index (CVRI) may also be calculated (step 1232). The CVRI may be defined as a percentage of the total brain volume affected by a plaque rupture or embolization and occlusion (closure or obstruction) of a vessel at a given location in the arterial tree. The CVRI may be calculated based on the portion of the brain supplied by the vessels downstream of the given plaque, which may take into account the size of the plaque with respect to the size of the downstream vessels and the probability that the plaque may flow into different vessels based on the three-dimensional hemodynamic solution. The CVRI may be assessed in diseased states, or before or after an intervention. Step 1232 may be similar to step 952 of FIG. 35 described above.

The brain tissue may be modeled and divided into segments supplied by each vessel in the hemodynamic simulation (e.g., as described in connection with steps 1110 and 1112 of FIG. 40). The geometric model may be modified to include a next generation of branches in the cerebral tree (e.g., as described in connection with step 1118 of FIG. 40), and the brain tissue may be further segmented (e.g., as described in connection with step 1120 of FIG. 40). Additional branches may be created in the subsegments, and the subsegments may be further segmented into smaller segments (e.g., as described in connection with step 1122 of FIG. 40). Physiologic relationships, as previously described, may be used to relate the size of a vessel to a proportional amount of brain tissue supplied.

Potential paths for a ruptured plaque to follow may be determined. The hemodynamic solution may be used to determine a percent chance that a plaque fragment or embolus may flow into different downstream vessels.

The size of the ruptured plaque may be compared with the size of the downstream vessels to determine where the plaque may eventually create an impediment to flow. This information may be combined with the vulnerability index to provide a probability map of the volume of the brain tissue that may potentially be affected by the ruptured plaque. The CVRI may be assigned to each potential affected segment.

A cerebral perfusion risk index (CPRI) may also be calculated (step 1234). The CPRI may be defined as a percentage of the total cerebral blood flow affected by a plaque rupture and occlusion of a vessel at a given location in the arterial tree. The CPRI indicates a potential loss of perfusion to the brain tissue segments, rather than the volume affected as indicated by the CVRI. For example, the effect of a rupture or embolization of a carotid artery plaque may vary depending on the geometry of the patient's circle of Willis (shown in FIG. 37) and may yield different CVRI and CPRI values due to these differences in anatomy. The perfusion rate to each segment of the brain tissue may be calculated, and the loss of perfusion may be calculated based on the vulnerability index, the hemodynamic solution, and the sizes of the plaque and vessels. The CPRI may be assessed in diseased states, or before or after an intervention. Step 1234 may be similar to step 954 of FIG. 35 described above.

As a result, biomechanical forces acting on carotid atherosclerotic plaques resulting from pulsatile pressure, pulsatile blood flow, and/or optionally neck motion may be assessed. The total stress that the plaque experiences resulting from the pulsatile pressure, pulsatile blood flow, and/or optionally neck motion may be quantified. The solution may take into account multiple sources of patient-specific hemodynamic stress acting on the plaque or on the interface between the plaque and the vessel wall. Also, plaque strength may be estimated based on medical imaging data, and indices relating to plaque vulnerability, cerebral volume risk, and cerebral perfusion risk may be quantified.

By determining anatomic and physiologic data for extracranial and intracranial arteries as described below, changes in blood flow at the arterial or organ level for a specific patient at various physical conditions may be predicted. Further, other information may be provided, such as a risk of transient ischemic attack, ischemic stroke, or aneurysm rupture, forces acting on atherosclerotic plaques or aneurysms, a predicted impact of medical interventional or surgical therapies on intracranial or extracranial blood flow, pressure, wall stress, or brain perfusion. Blood flow, pressure, and wall stress in the intracranial or extracranial arteries, and total and regional brain perfusion may be quantified and the functional significance of disease may be determined.

In addition to quantifying blood flow in the three-dimensional geometric model constructed from imaging data (e.g., as described above in step 1212), the model may be modified to simulate the effect of progression or regression of disease or medical, percutaneous, or surgical interventions. In an exemplary embodiment, the progression of atherosclerosis may be modeled by iterating the solution over time, e.g., by solving for shear stress or particle residence time and adapting the geometric model to progress atherosclerotic plaque development based on hemodynamic factors and/or patient-specific biochemical measurements. Furthermore, the effect of changes in blood flow, heart rate, blood pressure, and other physiologic variables on extracranial and/or intracranial artery blood flow or cerebral perfusion may be modeled through changes in the boundary conditions and used to calculate the cumulative effects of these variables over time.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

It will be apparent to those skilled in the art that various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A computer-implemented method for determining a hemodynamic pressure quantity, the method comprising:
   acquiring angiography data from a patient at a first physiological state of the patient, the first physiological state comprising a state of hyperemia, a state of rest, or a state of exercise, the angiography data comprising x-ray angiography data, magnetic resonance angiography data, and/or computed tomographic angiography data;
   determining, by a processor, a first flow in a blood vessel of the patient based on the angiography data, wherein the first flow corresponds to the first physiological state of the patient;
   determining, by the processor, a second flow in a blood vessel based on scaling the first flow by a numerical factor from the first physiological state to a second physiological state, the second physiological state comprising a state of hyperemia, a state of rest, or a state of exercise, wherein the second flow corresponds to the second physiological state of the patient that is different from the first physiological state of the patient;
   determining, by the processor, the hemodynamic pressure quantity based on the second flow; and
   reporting the hemodynamic pressure quantity.

2. The computer-implemented method of claim 1 wherein the hemodynamic pressure quantity comprises fractional flow reserve.

3. The computer-implemented method of claim 1 wherein at least a portion of the angiography data is acquired when the patient is at rest.

4. The computer-implemented method of claim 1 wherein at least a portion of the angiography data is acquired when the patient is in a state of hyperemia.

5. The computer-implemented method of claim 1 wherein the second flow comprises hyperemic flow.

6. The computer-implemented method of claim 1 wherein the blood vessel comprises a stenosis.

7. The computer-implemented method of claim 1 further comprising determining both the flow and a change in pressure.

8. The computer-implemented method of claim 1 wherein the angiography data is acquired only when the patient is at rest.

9. The computer-implemented method of claim 1 wherein the first physiological state comprises a rest state and wherein the second physiological state comprises a hyperemic state.

10. The computer-implemented method of claim 1 wherein acquiring angiography data from a patient is based on a contrast agent in the blood vessel.

11. The computer-implemented method of claim 1 further comprising modeling at least a portion of the blood vessel based on the angiography data.

12. The computer-implemented method of claim 1 wherein the first flow comprises a rest-state flow.

13. The computer-implemented method of claim 12 wherein determining the second flow comprises determining a hyperemic flow, wherein the hyperemic flow is derived from the rest-state flow.

14. A system for determining a hemodynamic pressure quantity, the system comprising:
    a processor;
    a non-transitory memory coupled to the processor;
    first logic stored in the memory and executable by the processor to cause the processor to acquire angiography data from a patient at a first physiological state of the patient, the first physiological state comprising a state of hyperemia, a state of rest, or a state of exercise, the angiography data comprising x-ray angiography data, magnetic resonance angiography data, and/or computed tomographic angiography data;
    second logic stored in the memory and executable by the processor to cause the processor to determine a flow as a scaled flow based on the angiography data, wherein the flow corresponds to a second physiological state of the patient that is different from the first physiological state of the patient, the second physiological state comprising a state of hyperemia, a state of rest, or a state of exercise;
    third logic stored in the memory and executable by the processor to cause the processor to determine a change in pressure in a blood vessel of the patient based on the angiography data;
    fourth logic stored in the memory and executable by the processor to cause the processor to determine the hemodynamic pressure quantity based on the flow and/or the change in pressure; and a display configured to output the hemodynamic pressure quantity.

15. The system of claim 14 wherein the hemodynamic pressure quantity comprises fractional flow reserve.

16. The system of claim 14 further comprising fifth logic stored in the memory and executable by the processor to cause the processor to monitor a contrast agent in the blood vessel.

17. The system of claim 14 further comprising fifth logic stored in the memory and executable by the processor to cause the processor to model at least a portion of the blood vessel based on the angiography data.

18. A non-transitory computer readable storage medium having stored therein data representing instructions executable by a programmed processor for determining a hemodynamic pressure quantity, the storage medium comprising instructions for:

acquiring angiography data from a patient at a first physiological state of the patient, the first physiological state comprising a state of hyperemia, a state of rest, or a state of exercise, the angiography data comprising x-ray angiography data, magnetic resonance angiography data, and/or computed tomographic angiography data;

determining a flow based on the angiography data, wherein the flow corresponds to a second physiological state of the patient that is different from the first physiological state of the patient, the second physiological state comprising a state of hyperemia, a state of rest, or a state of exercise, the flow being derived by scaling another flow determined for the first physiological state;

determining a change in pressure in a blood vessel of the patient based on the angiography data;

determining the hemodynamic pressure quantity based on the flow and/or the change in pressure; and outputting the hemodynamic pressure quantity.

* * * * *